(12) United States Patent
Uemoto et al.

(10) Patent No.: US 9,714,213 B2
(45) Date of Patent: Jul. 25, 2017

(54) 4-AMINOMETHYLBENZOIC ACID DERIVATIVE

(71) Applicant: TOA EIYO LTD., Chuo-ku (JP)

(72) Inventors: Kazuhiro Uemoto, Kawaguchi (JP); Yoshimichi Sato, Itabashi-ku (JP); Naoki Okada, Ageo (JP); Emiko Iimori, Ota-ku (JP); Masayuki Kageyama, Kawaguchi (JP)

(73) Assignee: TOA EIYO LTD., Chuo-ku (JP)

( * ) Notice: Subject to any disclaimer, the term of this patent is extended or adjusted under 35 U.S.C. 154(b) by 0 days.

(21) Appl. No.: 15/029,452

(22) PCT Filed: Oct. 14, 2014

(86) PCT No.: PCT/JP2014/077301
§ 371 (c)(1),
(2) Date: Apr. 14, 2016

(87) PCT Pub. No.: WO2015/056663
PCT Pub. Date: Apr. 23, 2015

(65) Prior Publication Data
US 2016/0264514 A1    Sep. 15, 2016

(30) Foreign Application Priority Data
Oct. 15, 2013 (JP) ................. 2013-214391

(51) Int. Cl.
A61K 31/197 (2006.01)
A61K 31/275 (2006.01)
(Continued)

(52) U.S. Cl.
CPC .......... *C07C 229/38* (2013.01); *A61K 31/197* (2013.01); *A61K 31/275* (2013.01); *A61K 31/381* (2013.01); *A61K 31/426* (2013.01); *C07C 229/46* (2013.01); *C07C 255/54* (2013.01); *C07C 255/59* (2013.01);
(Continued)

(58) Field of Classification Search
CPC .. A61K 31/197; A61K 31/275; A61K 31/381; A61K 31/426; C07C 2101/02; C07C 229/38; C07C 229/46; C07C 255/54; C07C 255/59; C07D 277/24;
(Continued)

(56) References Cited

U.S. PATENT DOCUMENTS 7,087,644 B1    8/2006  Alonso-Alija et al.
2004/0082658 A1   4/2004  Harter et al.
(Continued)

FOREIGN PATENT DOCUMENTS

CN    103038232 A    4/2013
JP    2004-525117 A  8/2004
(Continued)

OTHER PUBLICATIONS

Harald H.H.W. Schmidt, et al., NO-and Haem-Independent Soluble Guanylate Cyclase Activators, Handbook of Experiment Pharmacology, vol. 191, pp. 309-339, (2009).
Johannes-Peter Stasch, et al., NO-Independent, Haem-Dependent Soluble Guanylate Cyclase Stimulators, Handbook of Experiment Pharmacology, vol. 191, pp. 277-308, (2009).
John D. Parker, "Nitrate tolerance, oxidative stress, and mitochondrial function: another worrisome chapter on the effects of organic nitrates", The Journal of Clinical Investigation, vol. 113, No. 3, pp. 352-354, (Feb. 2004).
Johannes-Peter Stasch, et al., "Targeting the heme-oxidized nitric oxide receptor for selective vasodilatation of diseased blood vessels", The Journal of Clinical Investigation, vol. 116, No. 9, pp. 2552-2561, (Sep. 2006).
(Continued)

*Primary Examiner* — Valerie Rodriguez-Garcia
(74) *Attorney, Agent, or Firm* — Oblon, McClelland, Maier & Neustadt, L.L.P.

(57) ABSTRACT
A compound represented by general formula (1)

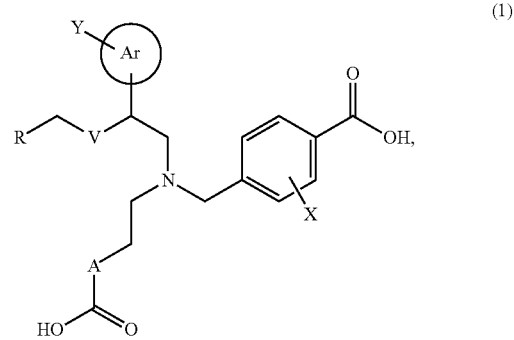

a pharmaceutically acceptable salt thereof or a solvate thereof; wherein Ar represents an aryl group, or a 5- or 6-membered heteroaryl group containing a nitrogen atom, an oxygen atom or a sulfur atom; Y represents, for example, a hydrogen atom or a $C_1$-$C_6$ alkyl group; A represents a $C_1$-$C_3$ alkylene chain which may be substituted with two $C_1$-$C_2$ alkyl groups; X represents a hydrogen atom or a halogen atom; V represents an oxygen atom or a methylene chain; and R represents a group selected from the formulae below:

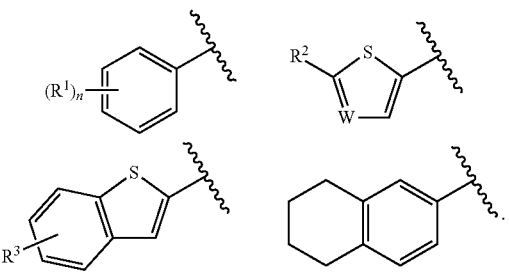

9 Claims, No Drawings

(51) Int. Cl.
  *A61K 31/381*  (2006.01)
  *A61K 31/426*  (2006.01)
  *C07C 229/46*  (2006.01)
  *C07C 229/38*  (2006.01)
  *C07C 255/59*  (2006.01)
  *C07C 255/54*  (2006.01)
  *C07D 277/24*  (2006.01)
  *C07D 333/16*  (2006.01)
  *C07D 333/20*  (2006.01)
  *C07D 333/28*  (2006.01)
  *C07D 333/56*  (2006.01)
  *C07D 333/32*  (2006.01)

(52) U.S. Cl.
  CPC ......... *C07D 277/24* (2013.01); *C07D 333/16* (2013.01); *C07D 333/20* (2013.01); *C07D 333/28* (2013.01); *C07D 333/32* (2013.01); *C07D 333/56* (2013.01); *C07C 2101/02* (2013.01)

(58) Field of Classification Search
  CPC .. C07D 333/16; C07D 333/20; C07D 333/28; C07D 333/32
  See application file for complete search history.

(56) References Cited

U.S. PATENT DOCUMENTS

| | | |
|---|---|---|
| 2004/0082798 A1 | 4/2004 | Alonso-Alija et al. |
| 2004/0092593 A1* | 5/2004 | Harter ............... C07C 229/38 514/566 |
| 2004/0176446 A1 | 9/2004 | Alonso-Alija et al. |
| 2006/0052397 A1 | 3/2006 | Alonso-Alija et al. |
| 2006/0094769 A1 | 5/2006 | Alonso-Alija et al. |
| 2006/0111444 A1 | 5/2006 | Harter et al. |
| 2009/0203906 A1 | 8/2009 | Alonso-Alija et al. |
| 2009/0209556 A1 | 8/2009 | Bittner et al. |
| 2010/0317854 A1 | 12/2010 | Alonso-Alija et al. |
| 2011/0028493 A1 | 2/2011 | Matsunaga et al. |
| 2011/0118282 A1 | 5/2011 | Bittner et al. |
| 2014/0038956 A1 | 2/2014 | Hirth-Dietrich et al. |

FOREIGN PATENT DOCUMENTS

| | | |
|---|---|---|
| JP | 2004-529111 A | 9/2004 |
| JP | 2004-529897 A | 9/2004 |
| JP | 2004-529898 A | 9/2004 |
| JP | 2013-526598 A | 6/2013 |
| WO | 01/19780 A2 | 3/2001 |
| WO | 03/095451 A1 | 11/2003 |
| WO | 2009/032249 A1 | 3/2009 |
| WO | 2009/071504 A1 | 6/2009 |
| WO | 2009/123316 A1 | 10/2009 |
| WO | 2011/147810 A1 | 12/2011 |

OTHER PUBLICATIONS

R.T. Schermuly, et al., "Expression and function of soluble guanylate cyclase in pulmonary arterial hypertension", European Respiratory Journal, vol. 32, No. 4, pp. 881-891, (2008).

Jennifer C. Irvine, et al., "The Soluble Guanylyl Cyclase Activator Bay 58-2667 Selectively Limits Cardiomyocyte Hypertrophy", PLOS ONE, vol. 7, No. 11, pp. 1-11, (Nov. 2012).

International Search Report Issued Jan. 13, 2015 in PCT/JP14/077301 Filed Oct. 14, 2014.

Combined Office Action and Search Report issued Feb. 4, 2017 in Chinese Patent Application No. 201480056587.6 (with English translation of categories of cited documents).

* cited by examiner

4-AMINOMETHYLBENZOIC ACID DERIVATIVE

FIELD OF THE INVENTION

The present invention relates to a 4-aminomethylbenzoic acid derivative having heme-independent activation effect for soluble guanylate cyclase (sGC), and a pharmaceutical agent containing the same.

BACKGROUND OF THE INVENTION

Soluble guanylate cyclase (sGC) is an enzyme producing cyclic guanosine monophosphate (cGMP) from guanosine triphosphate (GTP), and consists of a dimer of α subunit and β subunit. The β subunit is bonded to heme, and usually has an inactive structure, where the iron coordinated in the heme and the 105th histidine residue interact with each other. Nitrogen monoxide (NO) is known as a major sGC stimulating factor in vivo, and interacts with the heme iron present in the β subunit of sGC, and dissociate the interaction of the heme iron and the histidine residue of the β subunit whereby to transfer sGC to an activated form. cGMP produced by the activated sGC subsequently activates, for example, protein kinase or ion channel, and plays various roles such as relaxation of vascular smooth muscles, suppression of platelet activation, suppression of cell growth and neurotransmission of smell. Under pathological conditions, decline of sGC activity and decomposition of sGC occur, which leads to suppression of cGMPs, contraction of vascular smooth muscle, activation of platelet or cell growth, and eventually may be a cause for hypertension, pulmonary hypertension, heart failure, endothelial dysfunction, atherosclerosis, a peripheral vascular disease, angina pectoris, thrombosis, myocardial infarction, erectile dysfunction or renal dysfunction (Non Patent Documents 1 and 2).

A nitrate agent such as nitroglycerin is widely used clinically in order to activate sGC. They supply exogenous NO whereby to cause activation of sGC, and express pharmacological actions. However, the nitrate agents are known to have a tolerance in addition to side effects, which is a serious defect of this pharmaceutical agent. Suggested is that the phenomenon of tolerance to nitrate agent is due to a mechanism which is unassociated with sGC such as decline of the activity of mitochondria aldehyde dehydrogenase that is involved in release of NO (Non Patent Document 3). Thus, a compound directly activating sGC regardless of the release of NO can avoid the tolerance. In addition, under aging or pathological conditions such as, hypertension, diabetes and hyperlipidemia, it is suggested that oxidation of heme iron and decomposition of heme increase due to oxidative stress, and NO cannot interact with heme, and sufficient activation of sGC cannot be expected (Non Patent Document 4). As another sGC stimulating agent than NO, a direct sGC stimulating agent represented by Riociguat (Patent Document 1) is known, which is dependent on heme. It is shown that although these compounds activate sGC independently from NO, these compounds cannot sufficiently exhibit sGC activation ability under the oxidation condition of heme iron (Non Patent Document 5). Accordingly, it is considered that a compound having direct sGC activation effect without dependence on the oxidation state of heme differently from NO or Riociguat, is effective for treating or preventing various diseases such as hypertension, pulmonary hypertension, heart failure, endothelial dysfunction, atherosclerosis, a peripheral vascular disease, angina pectoris, thrombosis, myocardial infarction, erectile dysfunction and renal dysfunction.

As the compound having direct sGC activation effect without dependence on the oxidation state of heme, disclosed are Cinaciguat and related derivatives in Patent Document 2, pyrazole and triazole derivatives in Patent Document 3, 2,6-disubstituted pyridine derivatives in Patent Document 4, and heterocycle derivatives in Patent Document 5.

CITATION LIST

Patent Documents

Patent Document 1: WO 2003/095451 A
Patent Document 2: WO 2001/019780 A
Patent Document 3: WO 2009/032249 A
Patent Document 4: WO 2009/071504 A
Patent Document 5: WO 2009/123316 A

Non Patent Documents

Non Patent Document 1: Handbook of Experimental Pharmacology, Germany, Springer-Verlag, 2009, Vol. 191, p. 309-339
Non Patent Document 2: Handbook of Experimental Pharmacology, Germany, Springer-Verlag, 2009, Vol. 191, p. 277-308
Non Patent Document 3: The Journal of Clinical Investigation, US, American Society for Clinical Investigation, 2004, Vol. 113, 352-354
Non Patent Document 4: The Journal of Clinical Investigation, US, American Society for Clinical Investigation, 2006, Vol. 116, p. 2552-2561
Non Patent Document 5: European Respiratory Journal, Switzerland, European Respiratory Society, 2008, Vol. 32, p. 881-891

SUMMARY OF THE INVENTION

Problems to be Solved by the Invention

The object of the present invention is to provide a novel compound, which has a heme-independent activation effect with respect to soluble guanylate cyclase, and is useful as a pharmaceutical product.

Means for Solving the Problem

Thereupon, the present inventors synthesized various compounds, and performed screening toward an index of soluble guanylate cyclase activation effect. As such, the present inventors found that a compound having 4-aminomethylbenzoic acid as a basic structure is highly heme-independent, and has excellent soluble guanylate cyclase activation effect, and is useful as a pharmaceutical agent, whereby to complete the present invention.

Specifically, the present invention provides a compound represented by general formula (1):

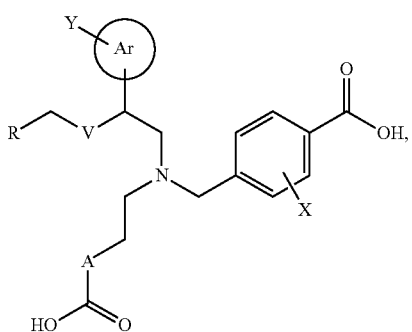

(1)

a pharmaceutically acceptable salt thereof or a solvate thereof;

wherein Ar represents an aryl group, or a 5- or 6-membered heteroaryl group containing a nitrogen atom, an oxygen atom or a sulfur atom;

Y represents a hydrogen atom, a $C_1$-$C_6$ alkyl group, a halo $C_1$-$C_4$ alkyl group, a cyano group, or a halogen atom;

A represents a $C_1$-$C_3$ alkylene chain which may be substituted with two $C_1$-$C_2$ alkyl groups, wherein the two $C_1$-$C_2$ alkyl groups may be substituted on the same carbon atom of the $C_1$-$C_3$ alkylene chain, and further the two $C_1$-$C_2$ alkyl groups may be taken together to form a $C_3$-$C_5$ saturated hydrocarbon ring containing one carbon atom of the $C_1$-$C_3$ alkylene chain;

X represents a hydrogen atom or a halogen atom;

V represents an oxygen atom or a methylene chain;

R represents a group selected from the formulae below

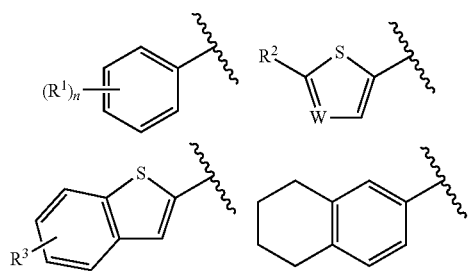

wherein $R^1$, $R^2$ and $R^3$ each independently represent a hydrogen atom, a halogen atom, a $C_1$-$C_6$ alkyl group which may have a substituent group, a $C_1$-$C_6$ alkoxy group, a $C_3$-$C_6$ cycloalkyl group, a $C_3$-$C_6$ cycloalkoxy group, a halo $C_1$-$C_4$ alkyl group, an aryl group which may have a substituent group on the aromatic ring, an aryloxy group which may have a substituent group on the aromatic ring, a benzyl group which may have a substituent group on the benzene ring, a phenethyl group which may have a substituent group on the benzene ring, or a benzyloxy group which may have a substituent group on the benzene ring, W represents =CH— or a nitrogen atom, n represents an integer of 1 to 3, and when n is 2 or more, n pieces of $R^1$ may be different from each other.

The present invention provides a pharmaceutical agent containing the compound represented by the general formula (1), a pharmaceutically acceptable salt thereof or a solvate thereof.

The present invention provides a pharmaceutical composition containing the compound represented by the general formula (1), a pharmaceutically acceptable salt thereof or a solvate thereof, and a pharmaceutically acceptable carrier.

In addition, the present invention provides a compound represented by the general formula (1), a pharmaceutically acceptable salt thereof or a solvate thereof for use as a pharmaceutical agent, preferably for use in preventing or treating a disease involving soluble guanylate cyclase such as heart failure, hypertension, pulmonary hypertension and an ischemic heart disease.

In addition, the present invention provides use of a compound represented by the general formula (1), a pharmaceutically acceptable salt thereof or a solvate thereof for manufacturing a pharmaceutical agent, and preferably an agent for preventing or treating a disease involving soluble guanylate cyclase such as heart failure, hypertension, pulmonary hypertension and an ischemic heart disease.

In addition, the present invention provides a method of preventing or treating a disease involving soluble guanylate cyclase such as heart failure, hypertension, pulmonary hypertension and an ischemic heart disease, the method including administering an effective amount of a compound represented by the general formula (1), a pharmaceutically acceptable salt thereof or a solvate thereof.

Advantageous Effects of the Invention

The compound of the present invention is highly heme-independent property, and has excellent soluble guanylate cyclase activation effect, and is useful as an agent for preventing or treating various diseases involving soluble guanylate cyclase. Examples of the disease that can be prevented or treated by soluble guanylate cyclase activation effect include heart failure, hypertension, pulmonary hypertension or an ischemic heart disease.

DETAILED DESCRIPTION OF THE INVENTION

The "aryl group" herein represents a $C_6$-$C_{10}$ aryl group, specifically a $C_{6-10}$ monocyclic or polycyclic aromatic hydrocarbon group. Specifically, examples of the aryl group include a phenyl group, a 1-naphthyl group and a 2-naphthyl group.

The "5- or 6-membered heteroaryl group containing a nitrogen atom, an oxygen atom or a sulfur atom" herein represents a $C_{4-5}$ monocyclic heteroaryl group containing 1 or 2 of nitrogen atoms, oxygen atoms or sulfur atoms. Specifically, examples of the 5- or 6-membered heteroaryl group containing a nitrogen atom, an oxygen atom or a sulfur atom include a furyl group, a thienyl group, a pyrazolyl group, a thiazolyl group, an isothiazolyl group, an oxazolyl group, an isoxazolyl group, an imidazolyl group, a pyrrolyl group, a pyridyl group, a pyridazinyl group, a pyrimidyl group and a pyrazinyl group.

Examples of the "halogen atom" herein include a fluorine atom, a chlorine atom, a bromine atom and an iodine atom.

The "$C_1$-$C_6$ alkyl group" herein represents a $C_{1-6}$ linear alkyl group or a $C_{3-6}$ branched chained alkyl group. Examples of the $C_1$-$C_6$ alkyl group include a methyl group, an ethyl group, a n-propyl group, a n-butyl group, an isopropyl group, an isobutyl group, a sec-butyl group, a tert-butyl group, a n-pentyl group, a n-hexyl group, a 2,2-dimethylpropyl group, a 3-methylbutyl group, a 3-ethylbutyl group and a 3,3-dimethylbutyl group.

The "$C_1$-$C_6$ alkoxy group" herein represents a group obtained by substituting one hydrogen atom with an oxygen atom in a $C_1$-$C_6$ alkyl group. Specifically, the $C_1$-$C_6$ alkoxy group is a $C_{1-6}$ linear alkoxy group or a $C_{3-6}$ branched chained alkoxy group, and examples of the $C_1$-$C_6$ alkoxy group include a methoxy group, an ethoxy group, a n-propoxy group, an isopropoxy group, a n-butoxy group, an isobutoxy group, a tert-butoxy group, a n-pentyloxy group and a n-hexyloxy group.

The "$C_{3-6}$ cycloalkyl group" herein represents a $C_{3-6}$ cyclic alkyl group. Specifically, examples of the $C_{3}$-$C_{6}$ cycloalkyl group include a cyclopropyl group, a cyclobutyl group, a cyclopentyl group and a cyclohexyl group.

The "$C_{3}$-$C_{6}$ cycloalkoxy group" herein represents a group obtained by substituting one hydrogen atom with an oxygen atom in the "$C_{3}$-$C_{6}$ cycloalkyl group". Specifically, examples of the $C_{3}$-$C_{6}$ cycloalkoxy group include a cyclopropoxy group, a cyclobutoxy group, a cyclopentyloxy group and a cyclohexyloxy group.

The "halo $C_1$-$C_4$ alkyl group" herein represents a group obtained by substituting one or more hydrogen atoms with a halogen atom in a $C_1$-$C_4$ alkyl group that is a $C_{1-4}$ linear or a $C_{3-4}$ branched chained alkyl group. Examples of the halo $C_1$-$C_4$ alkyl group include a chloromethyl group, a dichloromethyl group, a trichloromethyl group, a fluoromethyl group, a difluoromethyl group, a trifluoromethyl group, a bromomethyl group, a dibromomethyl group, a tribromomethyl group, a 2-chloroethyl group, a 2,2-dichloroethyl group, a 2,2,2-trichloroethyl group, a 2-fluoroethyl group, a 2,2-difluoroethyl group, a 2,2,2-trifluoroethyl group, a 1,1,2,2-tetrafluoroethyl group, a pentafluoroethyl group, a 2-bromoethyl group, a 2,2,2-tribromoethyl group, a 3,3,3-trichloropropyl group, a 3,3,3-trifluoropropyl group, a 3,3,3-tribromopropyl group, a 4,4,4-trichlorobutyl group and a 4,4,4-trifluorobutyl group.

The "aryloxy group" herein represents a group obtained by substituting one hydrogen atom with an oxygen atom in the "$C_6$-$C_{10}$ aryl group". Specifically, examples of the aryloxy group include a phenoxy group, a 1-naphthoxy group and a 2-naphthoxy group.

The "$C_1$-$C_3$ alkylene chain" herein represents a $C_{1-3}$ linear alkylene group. Specifically, examples of the $C_1$-$C_3$ alkylene chain include —$CH_2$—, —$(CH_2)_2$— and —$(CH_2)_3$—.

The "which may have a substituent group" herein represents that the subject is unsubstituted or has one or more, and preferably 1 or 2, more preferably one substituent, which is the same or different, at a substitutable position. Examples of the substituent include, a halogen atom, a $C_1$-$C_6$ alkyl group, a $C_1$-$C_6$ alkoxy group, a $C_3$-$C_6$ cycloalkyl group, a $C_3$-$C_6$ cycloalkoxy group, a $C_6$-$C_{10}$ aryl group, a $C_6$-$C_{10}$ aryloxy group, a benzyl group, a phenethyl group and a benzyloxy group. The definition of each substituent is as defined above, and it may further have a substituent.

The halogen atom represented by $R^1$, $R^2$ and $R^3$ is preferably a fluorine atom or a chlorine atom.

Examples of the substituent in the case where the $C_1$-$C_6$ alkyl group which may have a substituent group represented by $R^1$, $R^2$ and $R^3$ has a substituent include a $C_1$-$C_6$ alkoxy group, a $C_3$-$C_6$ cycloalkyl group and a $C_3$-$C_6$ cycloalkoxy group. Among them, the substituent is preferably a $C_3$-$C_6$ cycloalkyl group, and particularly preferably a cyclopentyl group or a cyclohexyl group. The $C_1$-$C_6$ alkyl group which may have a substituent group is preferably a methyl group, an ethyl group, a n-propyl group, an isopropyl group, a n-butyl group, a tert-butyl group, a 3,3-dimethylbutyl group, a 2-cyclopentylethyl group or a 2-cyclohexylethyl group. Among them, the $C_1$-$C_6$ alkyl group is more preferably a tert-butyl group, a 3,3-dimethylbutyl group, a 2-cyclopentylethyl group or a 2-cyclohexylethyl group.

The $C_3$-$C_6$ cycloalkyl group represented by $R^1$, $R^2$ and $R^3$ is preferably a cyclopropyl group, a cyclobutyl group, a cyclopentyl group or a cyclohexyl group, and particularly preferably a cyclopropyl group among them.

The halo $C_1$-$C_4$ alkyl group represented by $R^1$, $R^2$ and $R^3$ is preferably a $C_1$-$C_4$ alkyl group substituted with one or more fluorine atoms, and more preferably a $C_1$-$C_4$ alkyl group substituted with 1 to 5 fluorine atoms among them. Specifically, examples of the halo $C_1$-$C_4$ alkyl group include a trifluoromethyl group, a 2,2,2-trifluoroethyl group, a 1,1,2,2-tetrafluoroethyl group and a pentafluoroethyl group, and particularly preferably a trifluoromethyl group among them.

The aromatic ring in the $C_6$-$C_{10}$ aryl group which may have a substituent group on the aromatic ring or the $C_6$-$C_{10}$ aryloxy group which may have a substituent group on the aromatic ring represented by $R^1$, $R^2$ and $R^3$ is preferably a benzene ring. In the case where the aromatic ring has a substituent, the substituent is preferably a halogen atom, a $C_1$-$C_6$ alkyl group or a cyano group. The $C_6$-$C_{10}$ aryl group which may have a substituent group on the aromatic ring or the $C_6$-$C_{10}$ aryloxy group which may have a substituent group on the aromatic ring is preferably absent or has 1 to 2 substituents. Examples of the $C_6$-$C_{10}$ aryl group which may have a substituent group on the aromatic ring or a $C_6$-$C_{10}$ aryloxy group which may have a substituent group on the aromatic ring include specifically a phenyl group, a 4-fluorophenyl group, a 4-chlorophenyl group, a 4 methylphenyl group, a 4-tert-butylphenyl group, a 4-cyanophenyl group, a phenoxy group, a 4-fluorophenoxy group, a 4-chlorophenoxy group, a 4-methyl phenoxy group, a 4-tert-butyl phenoxy group and a 4-cyanophenoxy group. Among them, the $C_6$-$C_{10}$ aryl group which may have a substituent group on the aromatic ring or a $C_6$-$C_{10}$ aryloxy group which may have a substituent group on the aromatic ring is preferably a phenyl group, a 4-tert-butylphenyl group, a 4-chlorophenoxy group, a 4-methyl phenoxy group or a 4-cyanophenoxy group.

The benzyl group which may have a substituent group on the benzene ring, the phenethyl group which may have a substituent group on the benzene ring or the benzyloxy group which may have a substituent group on the benzene ring represented by $R^1$, $R^2$ and $R^3$ (hereinafter, the benzyl group, the phenethyl group and the benzyloxy group are collectively referred to as the benzyl group or the like) is preferably absent or has one or two substituents in the benzene ring, and particularly preferably has one substituent at the para position among them. The substituent is preferably a halogen atom or a halo $C_1$-$C_4$ alkyl group, and more preferably a chlorine atom or a trifluoromethyl group among them. The benzyl group or the like is preferably a phenethyl group or a benzyloxy group. Examples of the benzyl group or the like which may have a substituent group on the benzene ring include specifically a phenethyl group, a benzyloxy group, a (4-fluoro)phenethyl group, a (4-chloro)phenethyl group and a (4-trifluoromethyl)phenethyl group. Among them, the benzyl group or the like which may have a substituent group on the benzene ring is preferably a phenethyl group, a benzyloxy group, a (4-chloro)phenethyl group or a (4-trifluoromethyl)phenethyl group.

Examples of the $C_6$-$C_{10}$ aryl group or the 5- or 6-membered heteroaryl group containing a nitrogen atom, an oxygen atom or a sulfur atom represented by Ar include specifically a phenyl group, a furyl group, a thienyl group, a thiazolyl group, an oxazolyl group, an imidazolyl group, a pyrrolyl group, a pyridyl group and a pyrimidyl group. Among them, the $C_6$-$C_{10}$ aryl group or the 5- or 6-membered heteroaryl group containing a nitrogen atom, an oxygen atom or a sulfur atom represented by Ar is preferably a phenyl group or a thienyl group.

Y is a hydrogen atom, a $C_1$-$C_6$ alkyl group, a halo $C_1$-$C_4$ alkyl group, a cyano group or a halogen atom.

Examples of the $C_1$-$C_6$ alkyl group represented by Y include specifically a methyl group, an ethyl group, a n-propyl group, a n-butyl group, an isopropyl group, an isobutyl group, a sec-butyl group, a tert-butyl group and a 2,2-dimethylpropyl group. Among them, the $C_1$-$C_6$ alkyl group represented by Y is preferably a methyl group, an ethyl group or a tert-butyl group, and most preferably a methyl group.

The halo $C_1$-$C_4$ alkyl group represented by Y is preferably a fluoromethyl group, a difluoromethyl group, a trifluoromethyl group or a pentafluoroethyl group.

Examples of the halogen atom represented by Y include specifically a fluorine atom, a chlorine atom, a bromine atom and an iodine atom. Among them, the halogen atom represented by Y is preferably a chlorine atom or a fluorine atom, and particularly preferably a chlorine atom.

Y is particularly preferably a methyl group, a cyano group, or a chlorine atom. The substitution position of such Y with respect to Ar when Ar is a 6-membered ring, is preferably the meta position or the para position, and is most preferably the meta position. The substitution position of such Y with respect to Ar when Ar is a heteroaryl group, is preferably the carbon atom adjacent to the heteroatom.

Examples of the $C_1$-$C_3$ alkylene chain which may be substituted with two $C_1$-$C_2$ alkyl groups represented by A include specifically —$CH_2$—, —$(CH_2)_2$—, —$(CH_2)_3$— or the structures described below.

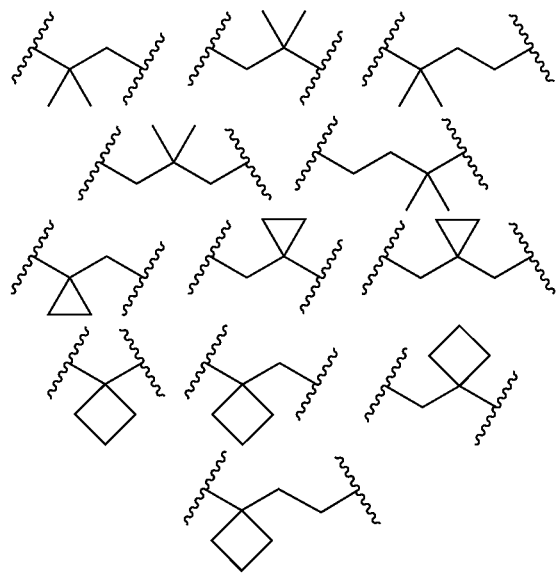

(the left end in each structure represents the binding site to the carboxyl group.)

Among them, the $C_1$-$C_3$ alkylene chain is preferably —$(CH_2)_2$— or a structure selected from the formulae below.

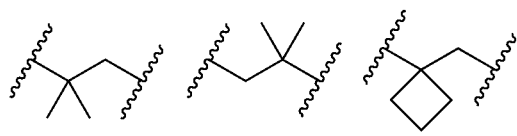

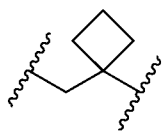

(the left end in each structure represents the binding site to the carboxyl group.)

X represents a hydrogen atom or a halogen atom. Among them, X is preferably a hydrogen atom or a fluorine atom. The substitution position of such X is preferably the ortho position with respect to the carboxyl group. V represents an oxygen atom or a methylene chain, and preferably an oxygen atom among them.

In the case where the group represented by R is the formula below

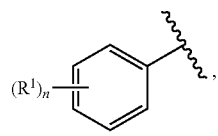

n is particularly preferably 1 or 2.

In the case where the group represented by R is the formula below

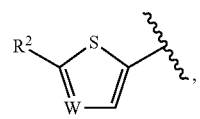

W in the formula is =CH— or a nitrogen atom, and preferably =CH— among them.

The group represented by R is preferably a group selected from the formulae below

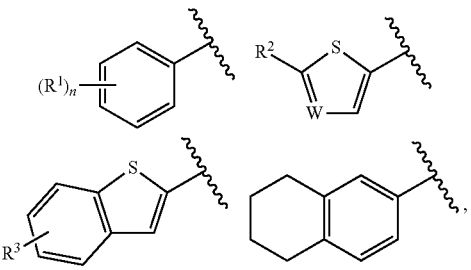

and is particularly preferably

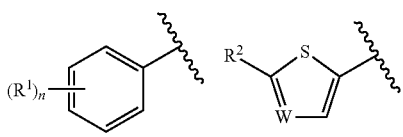

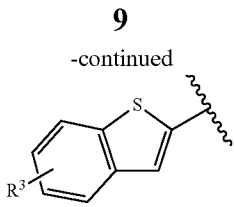

among them.

$R^1$ is preferably a halogen atom, a $C_1$-$C_6$ alkyl group which may have a substituent group, a halo $C_1$-$C_4$ alkyl group, an aryl group which may have a substituent group on the aromatic ring, an aryloxy group which may have a substituent group on the aromatic ring, a benzyl group or the like which may have a substituent group on the benzene ring. Among them, $R^1$ is more preferably a $C_1$-$C_6$ alkyl group which may have a substituent group, or a phenethyl group or benzyloxy group which may have a substituent group the benzene ring. The substitution position of $R^1$ is preferably the meta position or the para position. In addition, the substitution position of $R^1$ in the case where n is 2, is preferably a combination of the ortho position and the para position, or a combination of the meta positions. Herein, a substituent on the $C_1$-$C_6$ alkyl group is preferably a $C_3$-$C_6$ cycloalkyl group. The aryl group is preferably a phenyl group, and the aryloxy group is preferably a phenoxy group, and a substituent on these aryl group or aryloxy group is preferably a halogen atom, a $C_1$-$C_6$ alkyl group, a halo $C_1$-$C_4$ alkyl group or a cyano group. The substituent on the benzene ring is preferably a halogen atom or a halo $C_1$-$C_4$ alkyl group.

$R^2$ is preferably a $C_1$-$C_6$ alkyl group which may have a substituent group, an aryl group which may have a substituent group on the aromatic ring, an aryloxy group which may have a substituent group on the aromatic ring or a phenethyl group which may have a substituent group on the benzene ring. Among them, $R^2$ is most preferably a phenethyl group which may have a substituent group on the benzene ring. Herein, a substituent on a $C_1$-$C_6$ alkyl group is preferably absent. The aryl group is preferably a phenyl group, and the aryloxy group is preferably a phenoxy group, and a substituent on such aryl group or phenethyl group is preferably absent, and a substituent on the aryloxy group is preferably a $C_1$-$C_6$ alkyl group.

$R^3$ is preferably a halogen atom, or a $C_1$-$C_6$ alkyl group or a $C_3$-$C_6$ cycloalkyl group which may have a substituent group. The substitution position of $R^3$ is most preferably the position 6. Herein, the substituent on the $C_1$-$C_6$ alkyl group or a $C_3$-$C_6$ cycloalkyl group is preferably absent.

In general formula (1), it is preferred that Ar is a phenyl group or a thienyl group;
Y is a hydrogen atom, a $C_1$-$C_6$ alkyl group, a cyano group or a halogen atom;
A is, for example, —(CH$_2$)$_2$— or the structure represented by the formulae below,

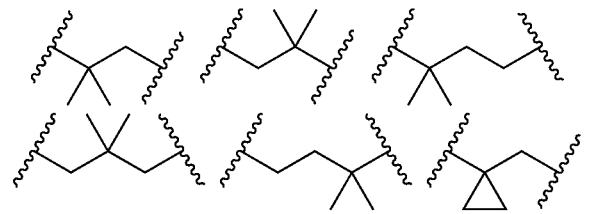

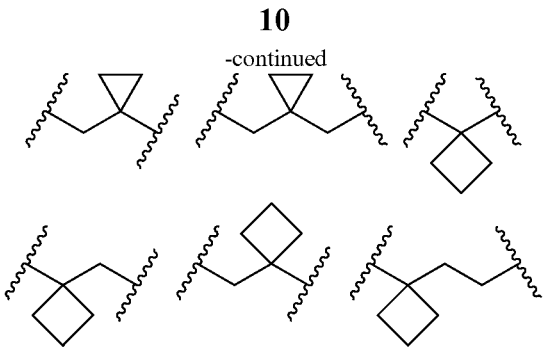

(the left end in each structure represents the binding site to the carboxyl group.)
X is a hydrogen atom or a halogen atom;
V is an oxygen atom; and
R is as follows.

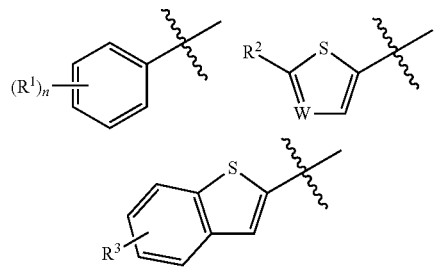

Herein, $R^1$, $R^2$, $R^3$, W and n are as described above.

In general formula (1), it is more preferred that Ar is a phenyl group or a thienyl group;
Y is a hydrogen atom, a $C_1$-$C_6$ alkyl group, a cyano group or a halogen atom;
A is, for example, —(CH$_2$)$_2$— or the structure represented by the formulae below,

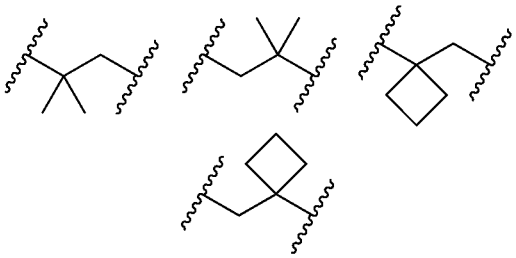

(the left end in each structure represents the binding site to the carboxyl group.)
X is a hydrogen atom or a halogen atom;
V is an oxygen atom; and
R is as follows.

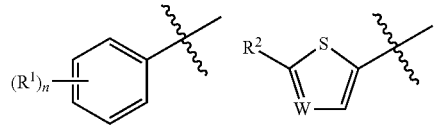

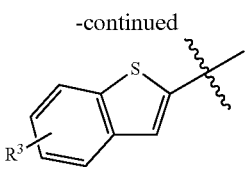

Herein, R¹, R², R³, W and n are as described above.

In the preferred aspect, R¹ is preferably a halogen atom, a $C_1$-$C_6$ alkyl group which may have a substituent group, a halo $C_1$-$C_4$ alkyl group, an aryloxy group which may have a substituent group on the aromatic ring, a phenethyl group which may have a substituent group on the benzene ring, or a benzyloxy group which may have a substituent group on the benzene ring. Among them, R¹ is more preferably a $C_1$-$C_6$ alkyl group which may have a substituent group, a phenethyl group which may have a substituent group on the benzene ring, or a benzyloxy group which may have a substituent group on the benzene ring. Herein, the substituent on the alkyl group, the aryloxy group and the benzene ring is preferably as described above.

R² is preferably a $C_1$-$C_6$ alkyl group which may have a substituent group, an aryl group which may have a substituent group on the aromatic ring, an aryloxy group which may have a substituent group on the aromatic ring, or a phenethyl group which may have a substituent group on the benzene ring. Among them, R² is most preferably a phenethyl group which may have a substituent group on the benzene ring. Herein, the substituent on the alkyl group, the aryl group, the aryloxy group and the benzene ring is preferably as described above.

R³ is preferably a halogen atom, a $C_1$-$C_6$ alkyl group which may have a substituent group or a $C_3$-$C_6$ cycloalkyl group. Herein, the substituent of the alkyl group is preferably as described above.

Particularly preferable examples of the compound of general formula (1) of the present invention specifically include the compounds described below among others.

4-{[N-(4-Carboxybutyl)-N-[2-[4-(2-phenylethyl)benzyloxy]-2-phenylethyl]amino]methyl}benzoic acid (Example 2)

4-{[N-[2-(3-tert-Butylbenzyloxy)-2-phenylethyl]-N-(4-carboxybutyl)amino]methyl}benzoic acid (Example 10)

4-{[N-(5-Carboxypentyl)-N-[2-[4-(2-phenylethyl)benzyloxy]-2-phenylethyl]amino]methyl}benzoic acid (Example 15)

4-{[N-(4-Carboxy-4-methyl pentyl)-N-[2-[4-(2-phenylethyl)benzyloxy]-2-phenylethyl]amino]methyl}benzoic acid (Example 16)

4-{([N-(4-Carboxy-3,3-dimethylbutyl)-N-[2-[4-(2-phenylethyl)benzyloxy]-2-phenylethyl]amino]methyl}benzoic acid (Example 18)

4-{([N-(4-Carboxybutyl)-N-[2-[4-(2-phenylethyl)benzyloxy]-2-(2-thienyl)ethyl]amino]methyl}benzoic acid (Example 19)

4-{[N-(4-Carboxybutyl)-N-[2-(3-chlorophenyl)-2-[4-(2-phenylethyl)benzyloxy]ethyl]amino]methyl}benzoic acid (Example 22)

4-{[N-(4-Carboxybutyl)-N-[2-(3-methylphenyl)-2-[4-(2-phenylethyl)benzyloxy]ethyl]amino]methyl}benzoic acid (Example 23)

4-{[N-(4-Carboxybutyl)-N-[2-(3-chlorophenyl)-2-[5-(2-phenylethyl)thiophen-2-ylmethoxy]ethyl]amino]methyl}benzoic acid (Example 24)

4-{[N-(4-Carboxybutyl)-N-[2-[5-(2-phenylethyl)thiophen-2-ylmethoxy]-2-phenylethyl]amino]methyl}benzoic acid (Example 25)

4-{[N-(4-Carboxybutyl)-N-[2-[4-(2-phenylethyl)benzyloxy]-2-(3-thienyl)ethyl]amino]methyl}benzoic acid (Example 26)

4-{[N-(4-Carboxybutyl)-N-[2-[4-(2-phenylethyl)benzyloxy]-2-(5-chloro-2-thienyl)ethyl]amino]methyl}benzoic acid (Example 27)

4-{[N-(4-Carboxybutyl)-N-[2-[4-(2-phenylethyl)benzyloxy]-2-(5-methyl-2-thienyl)ethyl]amino]methyl}-2-fluorobenzoic acid (Example 28)

(−)-4-{[N-(4-Carboxybutyl)-N-[(2R)-2-(3-chlorophenyl)-2-[4-(2-phenylethyl)benzyloxy]ethyl]amino]methyl}benzoic acid (Example 29)

(−)-4-{[N-(4-Carboxybutyl)-N-[(2R)-2-(3-cyanophenyl)-2-[4-(2-phenylethyl)benzyloxy]ethyl]amino]methyl}benzoic acid (Example 30)

(−)-4-{[N-(4-Carboxybutyl)-N-[(2R)-2-[4-(2-phenylethyl)benzyloxy]-2-phenylethyl]amino]methyl}benzoic acid (Example 32)

(−)-4-{[N-[(2R)-2-(3-tert-Butylbenzyloxy)-2-(3-chlorophenyl)ethyl]-N-(4-carboxybutyl)amino]methyl}benzoic acid (Example 34)

(−)-4-{[N-(4-Carboxybutyl)-N-[(2R)-2-[4-(2-cyclopentylethyl)benzyloxy]-2-phenylethyl]amino]methyl}benzoic acid (Example 39)

(−)-4-{[N-(4-Carboxybutyl)-N-[(2R)-2-[4-[2-(4-chlorophenyl)ethyl]benzyloxy]-2-phenylethyl]amino]methyl}benzoic acid (Example 40)

(−)-4-{[N-(4-Carboxybutyl)-N-[(2R)-2-[4-(4-chlorophenyloxy)benzyloxy]-2-phenylethyl]amino]methyl}benzoic acid (Example 42)

(−)-4-{[N-(4-Carboxybutyl)-N-[(2R)-2-[5-(2-phenylethyl)thiophen-2-ylmethoxy]-2-phenylethyl]amino]methyl}benzoic acid (Example 43)

(−)-4-{[N-(4-Carboxybutyl)-N-[(2R)-2-[2-fluoro-4-(2-phenylethyl)benzyloxy]-2-phenylethyl]amino]methyl}benzoic acid (Example 45)

(−)-4-{[N-(4-Carboxybutyl)-N-[(2R)-2-(3,5-di-tert-butylbenzyloxy)-2-phenylethyl]amino]methyl}benzoic acid (Example 46)

4-{[N-(4-Carboxybutyl)-N-[2-[3-(2-phenylethyl)benzyloxy]-2-phenylethyl]amino]methyl}benzoic acid (Example 60)

In the specification, the compound of general formula (1) may lead to an isomer such as a geometric isomer, an optical isomer, a steric isomer and a tautomer, and the compound of general formula (1) of the present invention encompasses any one of the isomers or a mixture thereof.

Further, the compound of general formula (1) of the present invention encompasses a compound labeled with, for example, an isotope (for example, $^2H$, $^3H$, $^{14}C$, $^{35}S$ or $^{125}I$).

In addition, the present invention encompasses a pharmaceutically acceptable salt of the compound of general formula (1). Specifically, examples of the pharmaceutically acceptable salt include an acid addition salt with an inorganic acid such as hydrochloride, hydrobromide, hydroiodide, sulfate, nitrate and phosphate, and an acid addition salt with an organic acid such as formate, acetate, trichioroacetate, trifluoroacetate, propionate, oxalate, malonate, succinate, fumarate, maleate, lactate, malate, tartrate, citrate, methanesulfonate, ethanesulfonate, benzenesulfonate, p-toluene sulfonate (4-methyl benzene sulfonate), aspartate or glutamate; a base addition salt with an inorganic base such as a sodium salt, a potassium salt, a magnesium salt, a calcium salt, an ammonium salt and an aluminum salt, and a base addition salt with an organic base such as methyl amine, ethyl amine, ethanol amine and lysine and ornithine.

Further, in the present invention, the compound (1) of the present invention and a pharmaceutically acceptable salt thereof may be present as a hydrate, various solvates and a crystalline polymorph form, and are not limited similarly, and any of the crystalline forms may be single or in a crystalline mixture, and all of them are encompassed.

Further, the compound (1) of the present invention may be converted to a prodrug by a pharmacologically acceptable group. Examples of the pharmacologically acceptable group forming a prodrug include, for example, the groups described in Prog. Med., 5, 2157-2161 (1985) and The "Development of medicine" (Hirokawa Publishing Company, 1990) Vol. 7, Molecular Design p. 163-198.

The compound of general formula (1) of the present invention, a pharmaceutically acceptable salt thereof or a solvate thereof (hereinafter, they are collectively referred to as the compound of the present invention) can be manufactured by applying various known synthetic methods related to introduction of a substituent or exchange of functional groups using features based on the basic structure or the kind of the substituent.

Hereinafter, methods of manufacturing the compound of the present invention are exemplified. However, a method of manufacturing the compound of the present invention is not limited thereto at all.

The compound of general formula (1) can be manufactured, for example, by the scheme below.

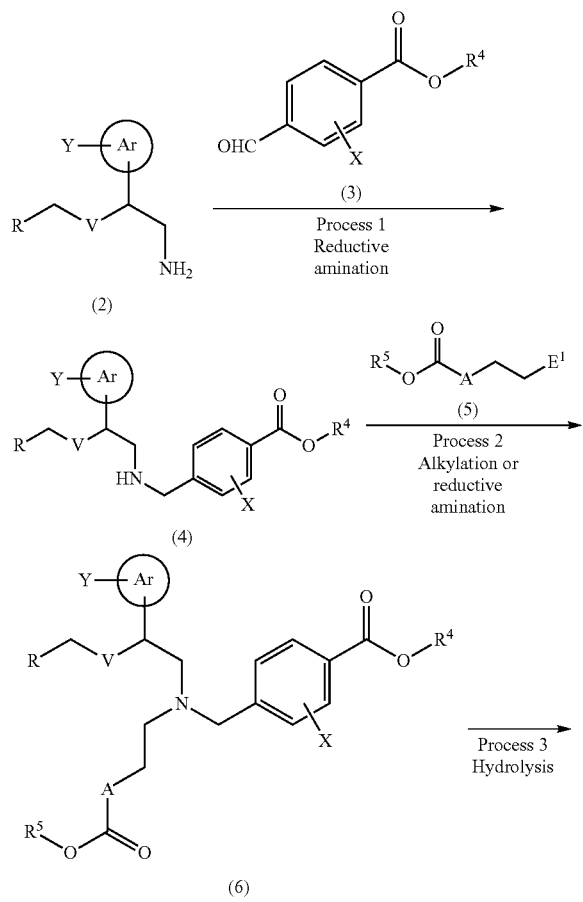

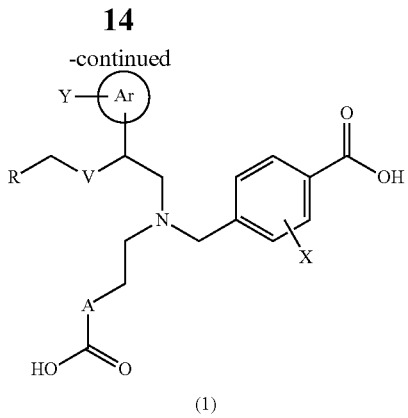

(wherein Ar, Y, R, V, X and A are as defined above. $R^4$ and $R^5$ each represent a $C_1$-$C_6$ alkyl group or a benzyl group. $E^1$ represents a leaving group or a formyl group.)

Herein, the "leaving group" represents a group that is replaced in the presence of a base or a group having an activated oxygen atom. Specifically, examples of the leaving group include a halogen atom; a trihalogenomethyloxy group such as a trichloromethyloxy group; a lower alkanesulfonyloxy group such as a methanesulfonyloxy group and an ethanesulfonyloxy group; a halogeno lower alkanesulfonyloxy group such as a trifluoromethanesulfonyloxy group and a pentafluoroethanesulfonyloxy group; and an arylsulfonyloxy group such as a benzene sulfonyloxy group, a 4-toluene sulfonyloxy group and a 4-nitrobenzene sulfonyloxy group.

Process 1: Reductive Amination

The compound (2) and the compound (3) are reacted in the absence of a solvent or in an inert solvent in the absence or presence of an acid, to first obtain a Schiff base, and subsequently this is reacted in the presence of a reducing agent, whereby to manufacture the compound (4).

The use amount of the compound (3) is usually 1 to 3 equivalents, and preferably 1 to 1.5 equivalents with respect to the compound (2). The acid used is, for example, an inorganic acid such as hydrochloric acid, hydrobromic acid, phosphoric acid and sulfuric acid; or an organic acid such as formic acid, acetic acid, propionic acid, methanesulfonic acid and p-toluene sulfonic acid. Examples of the reducing agent used include, for example, a borohydride compound such as a borane-tetrahydrofuran complex, sodium borohydride, sodium cyanoborohydride and sodium triacetoxyborohydride; an aluminum hydride compound such as lithium aluminum hydride; and hydrogen in the presence of a transition metal catalyst. The use amount of the reducing agent is usually 1 to 10 equivalents, and preferably 1 to 5 equivalents with respect to the compound (2). The solvent used is, for example, an aromatic hydrocarbon such as benzene and toluene, a halohydrocarbon such as chloroform and dichloromethane, an ether such as diethyl ether and tetrahydrofuran (hereinafter, referred to as THF), an ester such as ethyl acetate, propyl acetate and butyl acetate, an alcohol such as methanol, ethanol and 2-propanol, or a mixture thereof. The reaction temperature is usually −78° C. to 150° C., and preferably 0° C. to 60° C. The reaction time is usually for 5 minutes to 48 hours, and preferably 30 minutes to 24 hours.

Process 2: Alkylation or Reductive Amination

In the case where $E^1$ is a leaving group in the compound (5), the compound (4) and the compound (5) are reacted in the absence of a solvent or in an inert solvent in the presence of a base and as necessary, an additive to manufacture the compound (6). The use amount of the compound (5) is usually 1 to 5 equivalents, and preferably 1 to 3 equivalents with respect to the compound (4). The base used is, for example, alkali metal carbonate, alkali metal hydrogencarbonate, alkali metal hydride, alkali metal alkoxide or an organic amine such as triethylamine, diisopropylethylamine and pyridine. The additive used is, for example, alkali metal iodide, tetrabutylammonium salt, or a phase transfer catalyst such as crown ether. The solvent used is, for example, an aromatic hydrocarbon such as benzene and toluene, a nitrile such as acetonitrile, propionitrile and butyronitrile, a halohydrocarbon such as chloroform and dichloromethane, a ketone such as acetone and methylethylketone, an ether such as diethyl ether and THF, an alcohol such as methanol, ethanol and 2-propanol, an amide such as N,N-dimethylformamide (hereinafter, referred to as DMF) and N,N-dimethylacetoamide (hereinafter, referred to as DMA), or a mixture thereof. The reaction temperature is usually −30° C. to 150° C., and preferably 0° C. to 100° C. The reaction time is usually 0.5 to 72 hours, and preferably 0.5 to 48 hours.

In addition, in the case where $E^1$ is a formyl group in the compound (5), the compound (6) can be manufactured with a similar method to that of the process 1 from the compound (4) and the compound (5).

Process 3: Hydrolysis

The compound (6) obtained in Process 2 is subjected to de-esterification, to manufacture the compound of general formula (1). The de-esterification can be generally performed in accordance with a well-known method in the field of organic synthetic chemistry depending on the kind of the ester group ($CO_2R^4$, $CO_2R^5$). For example, the compound of general formula (1) can be manufactured by performing the hydrolysis reaction in the presence of a base.

The base used is, for example, alkali metal carbonate, alkali metal hydroxide, alkaline earth metal hydroxide or alkali metal alkoxide. The solvent used is an ether such as diethyl ether and THF, an alcohol such as methanol, ethanol and 2-propanol, water, or a mixture thereof. Meanwhile, in the hydrolysis reaction, water is essential. The reaction temperature is usually 0° C. to 150° C., and preferably room temperature to 80° C. The reaction time is usually 1 to 48 hours, and preferably 3 to 24 hours.

Meanwhile, an optically active compound of general formula (1) can be manufactured using an optically active compound (2). Further, an optically active compound of general formula (1) can be manufactured through means such as HPLC isolation by a chiral column in the compound of general formula (1).

In addition, the compound (2), the compound (3) and the compound (5) are commercially available, or can be manufactured with a known method.

Meanwhile, in the case where V is —O—, the compound (2) can be manufactured with the method of the scheme below.

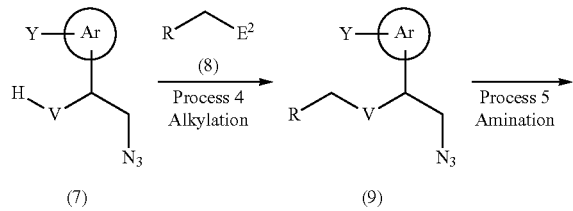

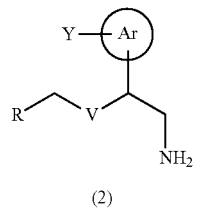

(wherein Ar, Y and R are as defined above, and V herein is —O—. $E^2$ represents a leaving group.)

Process 4: Alkylation

The compound (9) can be manufactured with a similar method to that of the process 2 from the compound (7) and the compound (8).

Meanwhile, the compound (7) and the compound (8) are commercially available, or can be manufactured with a known synthetic method.

Process 5: Amination

The compound (9) obtained in Process 4 and an organic phosphorus compound are reacted in the absence of a solvent or in an inert solvent in the presence of water, whereby to manufacture the compound (2).

The organic phosphorus compound used is, for example, triphenylphosphine, tri-n-butylphosphine or 1,2-bis(diphenylphosphino)ethane. The use amount of the organic phosphorus compound is usually 1 to 10 equivalents, and preferably 1 to 5 equivalents with respect to the compound (9). The solvent used is, for example, an aromatic hydrocarbon such as benzene and toluene, a nitrile such as acetonitrile, propionitrile and butyronitrile, a halohydrocarbon such as chloroform and dichloromethane, an ether such as diethyl ether and THF, an ester such as ethyl acetate, propyl acetate and butyl acetate, an amide such as DMF and DMA, a sulfoxide such as dimethyl sulfoxide (hereinafter, referred to as DMSO) and sulfolane, water, or a mixture thereof. The reaction temperature is usually 0° C. to 100° C., and preferably 0° C. to 60° C. The reaction time is usually 0.5 to 48 hours, and preferably 1 to 24 hours.

In addition, the compound (4) can be manufactured by reacting the compound (9) and an organic phosphorus compound in the absence of a solvent or in an inert solvent to first obtain iminophosphorane, and subsequently reacting this with the compound (3) to obtain a Schiff base and then reacting this in the presence of a reducing agent.

The organic phosphorus compound used is, for example, triphenylphosphine, tri-n-butylphosphine or 1,2-bis(diphenylphosphino)ethane. The use amount of the organic phosphorus compound is usually 1 to 10 equivalents, and preferably 1 to 3 equivalents with respect to the compound (9). The use amount of the compound (3) is usually 1 to 3 equivalents, and preferably 1 to 1.5 equivalents with respect to the compound (9). Examples of the reducing agent used include, for example, a borohydride compound such as a borane-tetrahydrofuran complex, sodium borohydride, sodium cyanoborohydride and sodium triacetoxyborohydride; an aluminum hydride compound such as lithium aluminum hydride; and hydrogen in the presence of a transition metal catalyst. The use amount of the reducing agent is usually 1 to 10 equivalents, and preferably 1 to 5 equivalents with respect to the compound (9). The solvent used is, for example, an aromatic hydrocarbon such as benzene and toluene, a halohydrocarbon such as chloroform and dichloromethane, an ether such as diethyl ether and THF, an ester such as ethyl acetate, propyl acetate and butyl acetate, an alcohol such as methanol, ethanol and 2-propanol, or a mixture thereof. The reaction temperature is usually −30° C. to 100° C., and preferably 0° C. to 60° C. The reaction time is usually 1 to 48 hours, and preferably 2 to 24 hours.

In addition, the compound (2) wherein V is —CH$_2$— may be manufactured with the method of the scheme below.

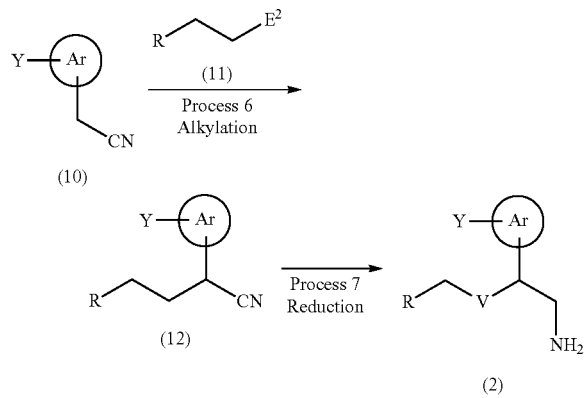

(wherein Ar, Y, R and E$^2$ are as defined above, and V herein is —CH$_2$—.)

Process 6: Alkylation

The compound (12) can be manufactured with a similar method to that of the process 2 from the compound (10) and the compound (11).

Meanwhile, the compound (10) and the compound (11) are commercially available, or can be manufactured with a known method.

Process 7: Reduction

The compound (12) obtained in Process 6 is reacted with a reducing agent in an inert solvent, whereby to manufacture the compound (2).

The reducing agent used is, for example, an aluminum hydride compound such as lithium aluminum hydride and sodium aluminum hydride; a borohydride compound such as lithium triethylborohydride; or a combination of a metal catalyst such as Raney nickel and palladium-carbon, and hydrogen. The use amount of the reducing agent is usually 1 to 10 equivalents, and preferably 1 to 3 equivalents with respect to the compound (12). In this process, an acid or a base may be suitably used as necessary. The acid used is, for example, an inorganic acid such as hydrochloric acid and hydrobromic acid; or an organic acid such as formic acid, acetic acid and propionic acid. The base used is, for example, an alkali metal hydroxide such as lithium hydroxide, sodium hydroxide and potassium hydroxide; an alkali metal alkoxide such as lithium methoxide, sodium methoxide, sodium ethoxide, sodium tert-butoxide and potassium tert-butoxide; or ammonia. The solvent used is, for example, an aromatic hydrocarbon such as benzene and toluene, an ether such as diethyl ether and THF, an alcohol such as methanol, ethanol and 2-propanol, an amide such as DMF and DMA, water, or a mixture thereof. The reaction temperature is usually −30° C. to 100° C., and preferably 0° C. to 80° C. The reaction time is usually 30 minutes to 48 hours, and preferably 1 to 24 hours.

In addition, the compound (6) wherein Y is a cyano group or a methyl group, is manufactured by reacting the compound (6) wherein Y is a chloro group with each of a cyanide reagent or a boric acid derivative in the absence of a solvent or in a solvent in the absence or presence of a palladium catalyst and a base, and may be used in the process 3.

The cyanide reagent used is, for example, tri-n-butyl tin cyanide, zinc cyanide, copper cyanide, sodium cyanide or potassium cyanide. The use amount of the cyanide reagent is usually 1 to 5 equivalents, and preferably 1 to 2 equivalents with respect to the compound (6). The boric acid derivative used is, for example, methyl boronic acid, methyl boronic acid anhydride or potassium methyl trifluoroborane. The use amount of the boric acid derivative is usually 1 to 5 equivalents, and preferably 1 to 3 equivalents with respect to the compound (6). The palladium catalyst used is not particularly limited if it is usually used in a reaction of producing a carbon-carbon bond, and is, for example, tetrakis(triphenylphosphine)palladium(0), bis[1,2-bis(diphenylphosphino)ethane]palladium(0), tris(dibenzylideneacetone)dipalladium(0), bis(tri-tert-butylphosphine)palladium(0), palladium(II) acetate, dichlorobis(triphenylphosphine)palladium(II) or dichlorobis[methylenebis(diphenylphosphine)]dipalladium-dichloromethane adduct. A phosphorus ligand that can be coordinated to the palladium catalyst may be used suitably as necessary in this process. The phosphorus ligand used is, for example, triphenylphosphine, tri-o-tolylphosphine, tri-tert-butylphosphine, 1,3-bis(diphenylphosphino)propane, 1,1'-bis(diphenylphosphino)ferrocene, 2-(dicyclohexylphosphino)-2',6'-dimethoxy 1,1'-biphenyl, 2-(dicyclohexylphosphino)-2',4',6'-tri-iso-propyl-1,1'-biphenyl or 2-(dicyclohexylphosphino)-3,6,-dimethoxy-2',4',6'-triisopropyl-1,1'-biphenyl. The base used is, for example, alkali metal carbonate, alkali metal hydrogencarbonate, alkali metal phosphatetriethylamine, or an organic amine such as triethylamine, diisopropylethylamine and pyridine. A metal salt can be suitably used as a catalyst as necessary in this process. The metal salt used is, for example, a copper salt such as copper(I) chloride, copper(I) bromide, copper(I) iodide, copper(II) chloride, copper(II) bromide and copper(II) iodide. The solvent used is, for example, an aromatic hydrocarbon such as benzene and toluene, a nitrile such as acetonitrile, propionitrile and butyronitrile, a halohydrocarbon such as chloroform and dichloromethane, ketones, an ether such as diethyl ether, THF and 1,4-dioxane, an alcohol such as methanol, ethanol and 2-propanol, an amide such as DMF, N-methyl-2-pyrrolidone and DMA, or a mixture thereof. The reaction temperature is usually 0° C. to 200° C., and preferably 50° C. to 180° C. The reaction time is usually 30 minutes to 48 hours, and preferably 1 to 24 hours.

Thus-obtained compound of the present invention has excellent heme-independent sGC activation effect as shown in Test Examples described later. Accordingly, the compound of the present invention is useful as a pharmaceutical agent for preventing or treating a disease involving sGC in an animal including human, particularly various diseases effective with sGC activation effect. Examples of the disease include heart failure, hypertension, pulmonary hypertension or an ischemic heart disease.

In the case where the compound of the present invention is used as a pharmaceutical agent, it can be administered by oral administration or parenteral administration. The dose of the compound of the present invention is suitably determined individually in consideration of a target disease or symptom, age, or weight or sex of an administration subject. The dose of the compound of the present invention per day for an adult (about 60 kg weight) in the case of oral administration is usually 1 to 1000 mg, preferably 3 to 300 mg, and further preferably 10 to 200 mg, which is administered once, or 2 to 4 times. In addition, the dose per day for an adult in the case of intravenous administration is usually 0.01 to 100 mg, preferably 0.01 to 50 mg, and more preferably 0.01 to 20 mg per 1 kg weight, which is administered once, or multiple times.

The pharmaceutical composition of the present invention can be manufactured by an ordinary method using one or more kinds of the compound of the present invention and a pharmaceutically acceptable additive.

Examples of the pharmaceutical composition of the present invention for oral administration include a tablet, a pill, a capsule, a granule, a powder, an emulsion, a solution, a suspension, a syrup, or an elixir. They can be usually manufactured as a pharmaceutical composition by mixing one or more kinds of the compound of the present invention and an additive such as an pharmaceutically acceptable diluent, a excipient and a carrier. In addition, the pharmaceutical composition of the present invention for oral administration may contain an additive such as a binder, a disintegrator, a lubricant, a swelling agent, a swelling aid, a coating agent, a plasticizer, a stabilizer, a preservative, an antioxidant, a colorant, a solubilizer, a suspending agent, an emulsifier, a sweetening agent, a preservative, a buffer and a humectant.

Examples of the pharmaceutical composition of the present invention for parenteral administration include an injection, a suppository, an eye drop, an inhalation, an ointment, a gel, a cream or a patch. They can be usually manufactured as a pharmaceutical composition by mixing one or more kinds of the compound of the present invention and an additive such as an pharmaceutically acceptable diluent, a excipient and a carrier.

In addition, the pharmaceutical composition of the present invention for parenteral administration may contain an additive such as a stabilizer, a preservative, a solubilizer, a moisturizing agent, a preservative, an antioxidant, a flavoring agent, a gelling agent, a neutralizer, a buffer, an isotonic agent, a surfactant, a colorant, a buffering agent, a thickener, a humectant, a filler, an absorption promoter, a suspending agent and a binder.

In addition, the pharmaceutical composition containing the compound of the present invention may suitably contain another medicinal ingredient such as a diuretic in addition as long as it does not conflict with the object of the present invention.

EXAMPLES

Hereinafter, the present invention will be specifically explained with Examples, but the present invention is not limited thereto.

Reference Example 1

2-Azido-1-(5-methylthiophen-2-yl)ethanone

2-Bromo-1-(5-methylthiophen-2-yl)ethanone (1.19 g) was dissolved in acetone (5.0 mL), and sodium azide (414 mg) and water (2.5 mL) were added, and the reaction solution was stirred at room temperature for 1.25 hours. The solvent was evaporated under reduced pressure, and the residue was extracted with diethyl ether. The residue was washed with saturated brine, and then dried over anhydrous sodium sulfate, and the solvent was evaporated under reduced pressure. The residue was purified by silica gel column chromatography (6 to 40% ethyl acetate/hexane) to yield the title compound (753 mg) as a yellow oil.

$^1$H-NMR(CDCl$_3$) δ: 7.54 (1H, d, J=3.7 Hz), 6.84 (1H, d, J=3.7 Hz), 4.39 (2H, s), 2.56 (3H, s).

Reference Example 2

2-Azido-1-(5-chlorothiophen-2-yl)ethanone

The title compound (446 mg) was manufactured as an orange powder from 2-bromo-1-(5-chloro-2-thienyl)ethanone (718 mg) with a similar method to that of Reference Example 1.

$^1$H-NMR(CDCl$_3$) δ: 7.52 (1H, d, J=4.2 Hz), 7.00 (1H, d, J=4.2 Hz), 4.38 (2H, s).

Reference Example 3

2-Azido-1-(5-methylthiophen-2-yl)ethanol

Reference Example 1 (736 mg) was dissolved in methanol (12.0 mL), and sodium borohydride (178 mg) was added under ice cooling, and the reaction solution was stirred at room temperature for 1 hour. A saturated aqueous solution of ammonium chloride was added, and the reaction solution was stirred, and then the solvent was evaporated under reduced pressure, and the residue was extracted with ethyl acetate. The combined organic layer was washed with saturated brine, and then dried over anhydrous sodium sulfate, and the solvent was evaporated under reduced pressure. The residue was purified by silica gel column chromatography (2 to 22% ethyl acetate/hexane) to yield the title compound (774 mg) as a colorless oil.

$^1$H-NMR(CDCl$_3$) δ: 6.82 (1H, d, J=3.5 Hz), 6.66-6.61 (1H, m), 5.03 (1H, dt, J=7.1, 4.2 Hz), 3.57 (1H, dd, J=12.5, 7.1 Hz), 3.51 (1H, dd, J=12.5, 4.2 Hz), 2.47 (3H, s), 2.35 (1H, d, J=4.2 Hz).

Reference Example 4

2-Azido-1-(5-chlorothiophen-2-yl)ethanol

The title compound (444 mg) was manufactured as an orange oil from Reference Example 2 (440 mg) with a similar method to that of Reference Example 3.

$^1$H-NMR(CDCl$_3$) δ: 6.83-6.78 (2H, m), 5.07-4.95 (1H, m), 3.55 (1H, s), 3.53 (1H, s), 2.51 (1H, d, J=4.2 Hz).

Reference Example 5

Ethyl 5-bromo-2,2-dimethylvalerate

Ethyl isobutyrate (2.32 g) was dissolved in THF (25.0 mL), and 1 mol/L lithium diisopropylamide (21 mL) was added dropwise at −78° C., and the reaction solution was stirred at the same temperature for 30 minutes. A THF solution of 1,3-dibromopropane (2.24 mL) was added dropwise at the same temperature, and the reaction solution was stirred for 1 hour, and then stirred at room temperature for 2 hours. The reaction solution was quenched with an aqueous solution of saturated ammonium chloride, and extracted with ethyl acetate. The combined organic layer was washed with water and saturated brine, and then dried over anhydrous sodium sulfate, and the solvent was evaporated under reduced pressure. The residue was purified by distillation under reduced pressure (0.05 mmHg, 42 to 43° C.) to yield the title compound (3.55 g) as a colorless oil.

$^1$H-NMR(CDCl$_3$) δ: 4.12 (2H, q, J=7.1 Hz), 3.38 (2H, t, J=6.6 Hz), 1.86-1.62 (4H, m), 1.25 (3H, t, J=7.1 Hz), 1.18 (6H, s).

Reference Example 6

Ethyl 1-(3-bromopropyl)cyclobutanecarboxylate

The title compound (3.09 g) was manufactured as a colorless oil from ethyl cyclobutanecarboxylate (2.56 g) with a similar method to that of Reference Example 5.
$^1$H-NMR(CDCl$_3$) δ: 4.15 (2H, q, J=7.0 Hz), 3.40 (2H, t, J=6.5 Hz), 2.49-2.34 (2H, m), 1.95-1.84 (6H, m), 1.80-1.71 (2H, m), 1.27 (3H, t, J=7.0 Hz).

Reference Example 7

Benzyl 5-hydroxy-3,3-dimethylvalerate

Monobenzyl 3,3-dimethylglutarate (200 mg) was dissolved in THF (4.0 mL), and 0.9 mol/L borane-tetrahydrofuran/THF solution (1.6 mL) was added dropwise, and the reaction solution was stirred at room temperature for 1 hour. The reaction solution was quenched with a saturated aqueous solution of sodium hydrogen carbonate under ice cooling, and extracted with ethyl acetate. The combined organic layer was dried over anhydrous sodium sulfate, and the solvent was evaporated under reduced pressure. The residue was purified by silica gel column chromatography (30 to 60% ethyl acetate/hexane) to yield the title compound (183 mg) as a colorless oil.
$^1$H-NMR(CDCl$_3$) δ: 7.37-7.31 (5H, m), 5.11 (2H, s), 3.76-3.70 (2H, m), 2.35 (2H, s), 1.63 (2H, t, J=6.9 Hz), 1.03 (6H, s).

Reference Example 8

Benzyl 3,3-dimethyl-5-oxovalerate

Reference Example 7 (500 mg) was dissolved in dichloromethane (11.0 mL), and Dess-Martin Periodinane (987 mg) was added under ice cooling, and the reaction solution was stirred at the same temperature for 1 hour. The reaction solution was purified by silica gel column chromatography (10 to 30% ethyl acetate/hexane) to yield the title compound (491 mg) as a colorless oil.

$^1$H-NMR(CDCl$_3$) δ: 9.81 (1H, t, J=2.5 Hz), 7.40-7.30 (5H, m), 5.11 (2H, s), 2.49 (2H, d, J=2.5 Hz), 2.45 (2H, s), 1.15 (6H, s).

Reference Example 9

Methyl 5-(2-phenylethyl)thiophen-2-carboxylate

Methyl 5-(2-phenylethenyl)thiophen-2-carboxylate (830 mg) was dissolved in a mixed solution of methanol and THF (4:1, 25.0 mL), 5% palladium carbon (STD type) (124 mg) was added, and the reaction solution was stirred at ordinary pressure and room temperature under hydrogen atmosphere for 18 hours. The reaction solution was filtered with Celite, and washed with methanol, and then the solvent was evaporated under reduced pressure. The residue was purified by silica gel column chromatography (5 to 20% ethyl acetate/hexane) to yield the title compound (831 mg) as a colorless oil.
$^1$H-NMR(CDCl$_3$) δ: 7.61 (1H, d, J=3.8 Hz), 7.32-7.16 (5H, m), 6.74 (1H, d, J=3.8 Hz), 3.86 (3H, s), 3.18-3.11 (2H, m), 3.03-2.96 (2H, m).

Reference Example 10

Ethyl 4-(2-cyclopentylethynyl)benzoate

Ethyl 4-iodobenzoate (1.00 g) was dissolved in DMF (18.0 mL), and cyclopentylacetylene (933 μL), triethylamine (1.51 mL), iodide copper (I) (34.5 mg) and bis(triphenylphosphine) palladium (II) chloride (254 mg) were sequentially added, and the reaction solution was stirred at room temperature under argon atmosphere for 1.5 hours. The solvent was evaporated under reduced pressure, and the residue was suspended in diisopropyl ether, and filtered with Celite, and then the solvent was evaporated under reduced pressure. The residue was purified by silica gel column chromatography (1 to 6% ethyl acetate/hexane) to yield the title compound (1.07 g) as a brown powder.
$^1$H-NMR(CDCl$_3$) δ: 7.95 (2H, d, J=8.2 Hz), 7.43 (2H, d, J=8.2 Hz), 4.37 (2H, q, J=7.1 Hz), 2.91-2.77 (1H, m), 2.09-1.92 (2H, m), 1.86-1.53 (6H, m), 1.39 (3H, t, J=7.1 Hz).

The compounds of Reference Examples 11 and 12 manufactured with a similar method to that of Reference Example 10 using corresponding raw materials are shown in Table 1.

TABLE 1

| Reference Example | Structural formula | $^1$H-NMR |
|---|---|---|
| 11 | 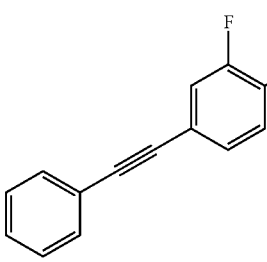 | (CDCl$_3$) δ 7.92 (1H, t, J = 7.8 Hz), 7.58-7.50 (2H, m), 7.42-7.23 (5H, m), 3.94 (3H, s). |

TABLE 1-continued

| Reference Example | Structural formula | $^1$H-NMR |
|---|---|---|
| 12 | *(4-(3,3-dimethylbut-1-yn-1-yl)benzoic acid ethyl ester)* | (CDCl$_3$) δ: 7.95 (2H, d, J = 8.1 Hz), 7.43 (2H, d, J = 8.1 Hz), 4.37 (2H, q, J = 7.1 Hz), 1.39 (3H, t, J = 7.1 Hz), 1.33 (9H, s). |

Reference Example 13

Ethyl 4-(2-cyclopentylethyl)benzoate

Reference Example 10 (990 mg) was dissolved in methanol (16.0 mL), and 5% palladium carbon (STD type) (990 mg) was added, and the reaction solution was stirred at ordinary pressure and room temperature under hydrogen atmosphere for 3 hours. The reaction solution was filtered with Celite, and washed with methanol, and then the solvent was evaporated under reduced pressure. The residue was diluted with ethyl acetate, and then dried over anhydrous sodium sulfate, and the solvent was evaporated under reduced pressure to yield the title compound as a crude product (a yellow oil).

$^1$H-NMR(CDCl$_3$) δ:
7.95 (2H, d, J=8.2 Hz), 7.24 (2H, d, J=8.2 Hz), 4.36 (2H, q, J=7.1 Hz), 2.74-2.58 (2H, m), 1.78-1.12 (14H, m).

The compounds of Reference Examples 14 to 18 manufactured with a similar method to that of Reference Example 13 using corresponding raw materials or Reference Examples 11 and 12 are shown in Table 2.

TABLE 2

| Reference Example | Structural formula | $^1$H-NMR |
|---|---|---|
| 14 | *(ethyl 4-(2-cyclohexylethyl)benzoate)* | (CDCl$_3$) δ: 7.95 (2H, d, J = 8.2 Hz), 7.23 (2H, d, J = 8.2 Hz), 4.36 (2H, q, J = 7.1 Hz), 2.74-2.58 (2H, m), 1.83-1.59 (5H, m), 1.58-1.44 (1H, m), 1.39 (3H, t, J = 7.1 Hz), 1.32-1.06 (5H, m), 1.03-0.82 (2H, m). |
| 15 | *(ethyl 4-(2-(4-chlorophenyl)ethyl)benzoate)* | (CDCl$_3$) δ: 7.95 (2H, d, J = 7.7 Hz), 7.34-7.12 (6H, m), 4.38 (2H, q, J = 7.0 Hz), 3.04-2.88 (4H, m), 1.39 (3H, t, J = 7.0 Hz). |
| 16 | *(ethyl 4-(2-(4-(trifluoromethyl)phenyl)ethyl)benzoate)* | (CDCl$_3$) δ: 7.96 (2H, d, J = 8.1 Hz), 7.52 (2H, d, J = 8.1 Hz), 7.24 (2H, d, J = 8.1 Hz), 7.20 (2H, d, J = 8.1 Hz), 4.37 (2H, q, J = 7.1 Hz), 2.99 (4H, s), 1.39 (3H, t, J = 7.1 Hz). |

TABLE 2-continued

| Reference Example | Structural formula | $^1$H-NMR |
|---|---|---|
| 17 | [structure: methyl 2-fluoro-4-(2-phenylethyl)benzoate] | (CDCl$_3$) δ: 7.84 (1H, t, J = 7.9 Hz), 7.32-7.09 (5H, m), 6.98 (1H, dd, J = 7.9, 1.5 Hz), 6.93 (1H, dd, J = 11.7, 1.5 Hz), 3.92 (3H, s), 3.01-2.88 (4H, m). |
| 18 | [structure: ethyl 4-(3,3-dimethylbutyl)benzoate] | (CDCl$_3$) δ: 7.95 (2H, d, J = 8.4 Hz), 7.25 (2H, d, J = 8.4 Hz), 4.36 (2H, q, J = 7.1 Hz), 2.65-2.59 (2H, m), 1.53-1.47 (2H, m), 1.39 (3H, t, J = 7.1 Hz), 0.97 (9H, s). |

Reference Example 19

Methyl 4-(4-tert-butylphenyl)-2-fluorobenzoate

Methyl 2-fluoro-4-iodobenzoate (505 mg) was dissolved in dimethoxyethane (4.0 mL), and 4-tert-butylphenylboronic acid (385 mg), bis(triphenylphosphine)palladium(II) chloride (63.3 mg) and anhydrous sodium carbonate (430 mg) were sequentially added at room temperature under argon atmosphere, and the reaction solution was stirred and heated under reflux for 4.66 hours. The reaction solution was cooled to room temperature, and then the solvent was evaporated under reduced pressure. The residue was suspended in chloroform, and filtered with Celite, and then the solvent was evaporated under reduced pressure. The residue was purified by silica gel column chromatography (1 to 10% ethyl acetate/hexane) to yield the title compound (421 mg) as a pale yellow solid.

$^1$H-NMR(CDCl$_3$) δ:
7.99 (1H, t, J=7.9 Hz), 7.56 (2H, d, J=8.5 Hz), 7.49 (2H, d, J=8.5 Hz), 7.43 (1H, dd, J=7.9, 1.6 Hz), 7.36 (1H, dd, J=12.1, 1.6 Hz), 3.95 (3H, s), 1.36 (9H, s).

Reference Example 20

Methyl 4-(4-chlorophenyloxy)-2-fluorobenzoate

4-Chlorophenol (200 mg) was dissolved in dichloromethane (16.0 mL), and [3-fluoro-4-(methoxycarbonyl)phenyl]boronic acid (400 mg), triethylamine (1.08 mL) and copper (II) acetate (282 mg) were added under ice cooling, and the reaction solution was stirred at room temperature for 2.5 hours. The solvent was evaporated under reduced pressure, and the residue was suspended in ethyl acetate, and filtered with Celite, and then the solvent was evaporated under reduced pressure. The residue was purified by silica gel column chromatography (2 to 8% ethyl acetate/hexane) to yield the title compound (130 mg) as a colorless oil.

$^1$H-NMR(CDCl$_3$) δ:
7.92 (1H, t, J=8.6 Hz), 7.38 (2H, d, J=9.0 Hz), 7.02 (2H, d, J=9.0 Hz), 6.76 (1H, dd, J=8.6, 2.4 Hz), 6.67 (1H, dd, J=11.9, 2.4 Hz), 3.91 (3H, s).

Reference Example 21

[5-(2-Phenylethyl)thiophen-2-yl]methyl alcohol

To a suspension of lithium aluminum hydride (206 mg) in THF (30.0 mL), a THF solution (12.0 mL) of Reference Example 9 (2.06 g) was added dropwise under ice cooling, and the reaction solution was stirred at the same temperature for 1 hour. Sodium sulfate 10-hydrate was added portionwise at the same temperature, and then the reaction solution was stirred at room temperature for 1 hour. The reaction solution was filtered with Celite, and washed with ethyl acetate, and then the solvent was evaporated under reduced pressure. The residue was purified by silica gel column chromatography (15 to 30% ethyl acetate/hexane) to yield the title compound (1.58 g) as a colorless oil.

$^1$H-NMR(CDCl$_3$) δ: 7.32-7.25 (2H, m), 7.25-7.17 (3H, m), 6.81 (1H, d, J=3.5 Hz), 6.62 (1H, d, J=3.5 Hz), 4.75 (2H, d, J=6.0 Hz), 3.15-3.06 (2H, m), 3.02-2.93 (2H, m), 1.67 (1H, t, J=6.0 Hz).

The compounds of Reference Examples 22 to 29 manufactured with a similar method to that of Reference Example 21 using the compounds of Reference Examples 13 to 20 are shown in Table 3.

TABLE 3

| Reference Example | Structural formula | $^1$H-NMR |
|---|---|---|
| 22 | [structure: 4-(2-cyclopentylethyl)benzyl alcohol] | (CDCl$_3$) δ: 7.28 (2H, d, J = 8.2 Hz), 7.18 (2H, d, J = 8.2 Hz), 4.66 (2H, d, J = 5.5 Hz), 2.62 (2H, t, J = 8.0 Hz), 1.89-1.71 (3H, m), 1.71-1.45 (7H, m), 1.23-1.01 (2H, m). |

TABLE 3-continued

| Reference Example | Structural formula | $^1$H-NMR |
|---|---|---|
| 23 | 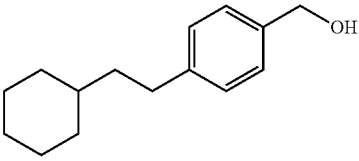 [SMILES: OCc1ccc(CCC2CCCCC2)cc1] | (CDCl$_3$) δ: 7.27 (2H, d, J = 8.2 Hz), 7.17 (2H, d, J = 8.2 Hz), 4.65 (2H, d, J = 5.7 Hz), 2.69-2.55 (2H, m), 1.86-1.41 (8H, m), 1.32-1.13 (3H, m), 1.04-0.82 (2H, m). |
| 24 | 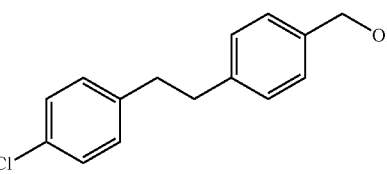 | (CDCl$_3$) δ: 7.36-7.12 (8H, m), 4.66 (2H, d, J = 5.5 Hz), 2.92 (4H, s), 1.59 (1H, t, J = 5.5 Hz). |
| 25 | 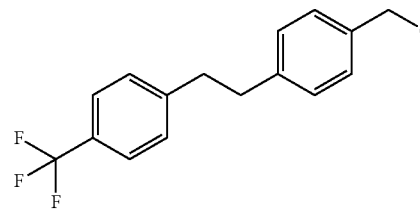 | (CDCl$_3$) δ: 7.52 (2H, d, J = 8.4 Hz), 7.32-7.20 (4H, m), 7.15 (2H, d, J = 8.1 Hz), 4.67 (2H, d, J = 5.7 Hz), 3.05-2.83 (4H, m), 1.60 (1H, t, J = 5.7 Hz). |
| 26 | 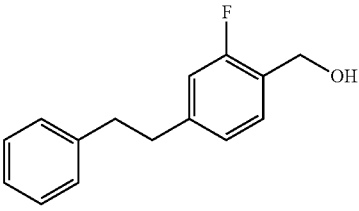 [SMILES: OCc1ccc(CCc2ccccc2)cc1F] | (CDCl$_3$) δ: 7.34-7.24 (3H, m), 7.24-7.13 (3H, m), 6.95 (1H, dd, J = 7.7, 1.5 Hz), 6.87 (1H, dd, J = 11.2, 1.5 Hz), 4.72 (2H, d, J = 6.0 Hz), 2.91 (4H, s), 1.72 (1H, t, J = 6.0 Hz). |
| 27 | 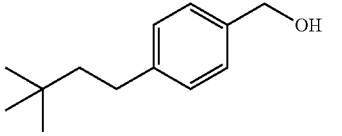 | (CDCl$_3$) δ: 7.27 (2H, d, J = 8.1 Hz), 7.18 (2H, d, J = 8.1 Hz), 4.65 (2H, d, J = 5.5 Hz), 2.60-2.54 (2H, m), 1.61 (1H, t, J = 5.5 Hz), 1.51-1.45 (2H, m), 0.96 (9H, s). |
| 28 | 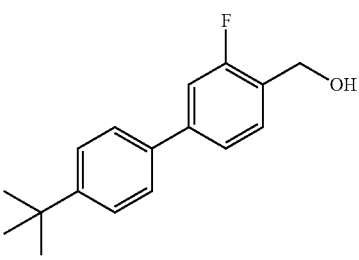 [SMILES: CC(C)(C)c1ccc(-c2ccc(CO)c(F)c2)cc1] | (CDCl$_3$) δ: 7.56-7.43 (5H, m), 7.38 (1H, dd, J = 8.0, 1.6 Hz), 7.29 (1H, dd, J = 11.5, 1.6 Hz), 4.79 (2H, d, J = 6.1 Hz), 1.78 (1H, t, J = 6.1 Hz), 1.36 (9H, s). |
| 29 | 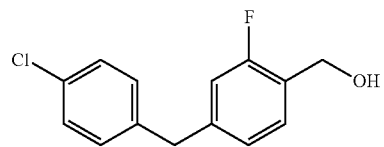 [SMILES: OCc1ccc(Cc2ccc(Cl)cc2)cc1F] | (CDCl$_3$) δ: 7.36 (1H, t, J = 8.3 Hz), 7.32 (2H, d, J = 9.0 Hz), 6.96 (2H, d, J = 9.0 Hz), 6.77 (1H, dd, J = 8.3, 2.4 Hz), 6.70 (1H, dd, J = 11.0, 2.4 Hz), 4.72 (2H, d, J = 6.0 Hz), 1.72 (1H, t, J = 6.0 Hz). |

Reference Example 30

(2-tert-Butyl-1,3-thiazol-5-yl)methanol 2-tert-Butyl-1,3-thiazol-5-carbaldehyde (535 mg) was dissolved in methanol (15.0 mL), and sodium borohydride (132 mg) was added under ice cooling, and the reaction solution was stirred at room temperature for 1 hour. An aqueous solution of saturated ammonium chloride was added, and the reaction solution was stirred, and then the solvent was evaporated under reduced pressure, and the residue was extracted with ethyl acetate. The combined organic layer was washed with saturated brine, and then dried over anhydrous sodium sulfate, and the solvent was evaporated under reduced pressure. The residue was purified by silica gel column chromatography (5 to 50% ethyl acetate/hexane) to yield the title compound (467 mg) as a colorless oil.
$^1$H-NMR(CDCl$_3$) δ:
7.53 (1H, s), 4.83 (2H, dd, J=6.0, 0.6 Hz), 1.82 (1H, t, J=6.0 Hz), 1.43 (9H, s).

Reference Example 31

[5-(4-Methylphenyloxy)thiophen-2-yl]methanol

The title compound (391 mg) was manufactured as a colorless oil from [5-(4-methylphenyloxy)thiophen-2-carbaldehyde (375 mg) with a similar method to that of Reference Example 30.
$^1$H-NMR(CDCl$_3$) δ:
7.12 (2H, d, J=8.8 Hz), 6.99 (2H, d, J=8.8 Hz), 6.71 (1H, dt, J=3.8, 0.8 Hz), 6.35 (1H, d, J=3.8 Hz), 4.70 (2H, dd, J=6.0, 0.8 Hz), 2.32 (3H, s), 1.70 (1H, t, J=6.0 Hz)

Reference Example 32

(6-Cyclopropylbenzo[b]thiophen-2-yl)methanol (6-Bromobenzo[b]thiophen-2-yl)methanol (500 mg) was dissolved in toluene (9.0 mL), and water (1.0 mL) was added, and potassium cyclopropyltrifluoroborate (457 mg), potassium carbonate (853 mg), 2-dicyclohexyl phosphino-2',4',6'-triisopropyl biphenyl (196 mg) and palladium acetate (46 mg) were sequentially added under argon atmosphere, and the reaction solution was stirred at 100° C. for 19 hours. The reaction solution was cooled to room temperature, filtered with Celite, and washed with ethyl acetate, and then the filtrate was diluted with water, and extracted with ethyl acetate. The combined organic layer was washed with saturated brine, and then dried over anhydrous sodium sulfate, and the solvent was evaporated under reduced pressure. The residue was purified by amino-functionalized silica gel column chromatography (20 to 40% ethyl acetate/hexane) to yield the title compound (223 mg) as a colorless oil.
$^1$H-NMR(CDCl$_3$) δ:
7.59 (1H, d, J=8.2 Hz), 7.52 (1H, d, J=0.7 Hz), 7.14 (1H, d, J=0.7 Hz), 7.06 (1H, dd, J=8.2, 1.5 Hz), 4.89 (2H, d, J=5.5 Hz), 2.05-1.95 (1H, m), 1.87 (1H, t, J=5.5 Hz), 1.03-0.93 (2H, m), 0.77-0.67 (2H, m).

Reference Example 33

[5-(2-Phenylethyl)-2-chloromethyl]thiophene

Reference Example 21 (327 mg) was dissolved in dichloromethane (8.0 mL), thionyl chloride (129 μL) was added, and the reaction solution was stirred at room temperature for 1 hour. The solvent and the reagents were evaporated under reduced pressure to yield the title compound as a crude product (a pale purple oil).
$^1$H-NMR(C$_6$D$_6$) δ: 6.77-6.63 (3H, m), 6.57-6.50 (2H, m), 6.08 (1H, d, J=3.5 Hz), 5.87 (1H, d, J=3.5 Hz), 3.83 (2H, s), 2.40-2.26 (4H, m).

The compounds of Reference Examples 34 to 41 manufactured with a similar method to that of Reference Example 33 using the compounds of Reference Examples 22 to 29 are shown in Table 4.

TABLE 4

| Reference Example | Structural formula | $^1$H-NMR |
|---|---|---|
| 34 | | (CDCl$_3$) δ: 7.29 (2H, d, J = 8.1 Hz), 7.17 (2H, d, J = 8.1 Hz), 4.57 (2H, s), 2.69-2.55 (2H, m), 1.87-1.40 (9H, m), 1.14-1.10 (2H, m). |
| 35 | | (CDCl$_3$) δ: 7.29 (2H, d, J = 8.1 Hz), 7.16 (2H, d, J = 8.1 Hz), 4.57 (2H, s), 2.61 (2H, dd, J = 9.3, 7.0 Hz), 1.83-1.59 (5H, m), 1.57-1.43 (2H, m), 1.34-1.10 (4H, m), 1.03-0.84 (2H, m). |
| 36 | | (CDCl$_3$) δ: 7.33-7.24 (4H, m), 7.23-7.14 (4H, m), 4.57 (2H, s), 2.92 (4H, s). |
| 37 | | (CDCl$_3$) δ: 7.53 (2H, d, J = 8.1 Hz), 7.31 (2H, d, J = 8.4 Hz), 7.26 (2H, d, J = 8.4 Hz), 7.15 (2H, d, J = 8.1 Hz), 4.58 (2H, s), 2.97-2.93 (4H, m). |

TABLE 4-continued

| Reference Example | Structural formula | $^1$H-NMR |
|---|---|---|
| 38 | 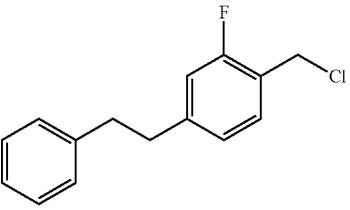 [SMILES: Fc1cc(CCc2ccccc2)ccc1CCl] | (CDCl$_3$) δ: 7.34-7.13 (6H, m), 6.95 (1H, dd, J = 7.7, 1.5 Hz), 6.89 (1H, dd, J = 10.8, 1.5 Hz), 4.62 (2H, s), 2.91 (4H, s). |
| 39 | 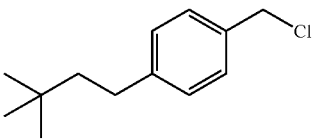 | (CDCl$_3$) δ: 7.29 (2H, d, J = 8.2 Hz), 7.17 (2H, d, J = 8.2 Hz), 4.57 (2H, s), 2.60-2.54 (2H, m), 1.51-1.45 (2H, m), 0.96 (9H, s). |
| 40 | 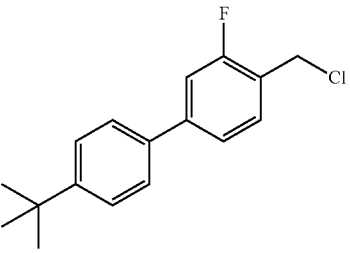 [SMILES: CC(C)(C)c1ccc(-c2ccc(CCl)c(F)c2)cc1] | (CDCl$_3$) δ: 7.60-7.21 (7H, m), 4.68 (2H, s), 1.37 (9H, s). |
| 41 | 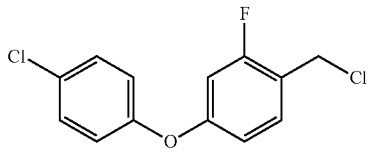 [SMILES: Fc1cc(Oc2ccc(Cl)cc2)ccc1CCl] | (CDCl$_3$) δ: 7.39-7.29 (3H, m), 6.98 (2H, d, J = 9.0 Hz), 6.76 (1H, dd, J = 8.3, 2.4 Hz), 6.69 (1H, dd, J = 11.0, 2.4 Hz), 4.61 (2H, s). |

Reference Example 42

5-Bromomethyl-2-tert-butylthiazole

Reference Example 30 (375 mg) was dissolved in dichloromethane (7.0 mL), and triphenylphosphine (603 mg) and carbontetrabromide (762 mg) were added under ice cooling, and the reaction solution was stirred at room temperature for 1.16 hours. The solvent was evaporated under reduced pressure, and the residue was extracted with ethyl acetate. The combined organic layer was washed with saturated brine, and then dried over anhydrous sodium sulfate, and the solvent was evaporated under reduced pressure. The residue was purified by silica gel column chromatography (0 to 5% ethyl acetate/hexane) to yield the title compound (465 mg) as a colorless oil.
$^1$H-NMR(CDCl$_3$) δ: 7.60 (1H, s), 4.69 (2H, s), 1.43 (9H, s).

Reference Example 43

2-Azido-1-phenylethyl 4-tert-butylbenzyl ether

2-Azido-1-phenyl ethanol (362 mg) was dissolved in DMF (11 mL), sodium hydride (133 mg) was added under ice cooling, and the reaction solution was stirred at the same temperature for 30 minutes. 4-Tert-butylbenzyl bromide (756 mg) was added at the same temperature, and the reaction solution was stirred at room temperature for 1.25 hours. The reaction solution was quenched with water, and extracted with diethyl ether. The combined organic layer was washed with saturated brine, and then dried over anhydrous sodium sulfate, and the solvent was evaporated under reduced pressure. The residue was purified by silica gel column chromatography (0 to 2% ethyl acetate/hexane) to yield the title compound (606 mg) as a colorless oil.
$^1$H-NMR(CDCl$_3$) δ: 7.43-7.24 (9H, m), 4.58 (1H, dd, J=8.6, 3.7 Hz), 4.51 (1H, d, J=11.5 Hz), 4.36 (1H, d, J=11.5 Hz), 3.56 (1H, dd, J=12.9, 8.6 Hz), 3.19 (1H, dd, J=12.9, 3.7 Hz), 1.32 (9H, s).

The compounds of Reference Examples 44 to 81 manufactured with a similar method to that of Reference Example 43 using corresponding raw materials or Reference Example compounds are shown in Tables 5 to 10.

TABLE 5
| Reference Example | Structural formula | ¹H-NMR |
|---|---|---|
| 44 | 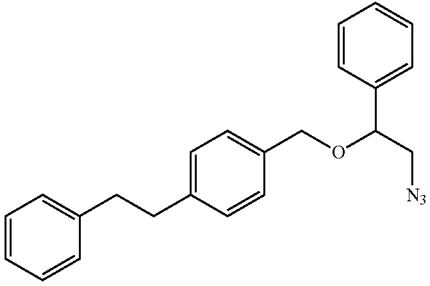 [SMILES: [N-]=[N+]=NCC(OCc1ccc(CCc2ccccc2)cc1)c1ccccc1] | (CDCl₃) δ: 7.43-7.34 (5H, m), 7.33-7.24 (2H, m), 7.21-7.17 (7H, m), 4.57 (1H, dd, J = 8.5, 3.7 Hz), 4.52 (1H, d, J = 11.4 Hz), 4.35 (1H, d, J = 11.4 Hz), 3.55 (1H, dd, J = 13.0, 8.5 Hz), 3.19 (1H, dd, J = 13.0, 3.7 Hz), 2.89 (4H, s). |
| 45 | 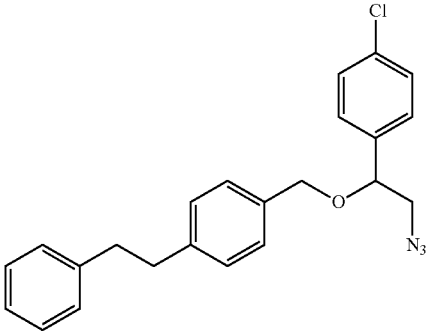 | (CDCl₃) δ: 7.38-7.36 (2H, m), 7.30-7.25 (4H, m), 7.20-7.17 (7H, m), 4.53 (1H, dd, J = 8.2, 3.8 Hz), 4.49 (1H, d, J = 11.5 Hz), 4.34 (1H, d, J = 11.5 Hz), 3.51 (1H, ddd, J = 13.0, 8.2, 1.5 Hz), 3.17 (1H, ddd, J = 13.0, 3.8, 1.5 Hz), 2.94 (4H, s). |
| 46 | 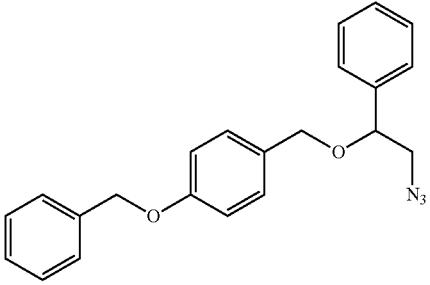 [SMILES: [N-]=[N+]=NCC(OCc1ccc(OCc2ccccc2)cc1)c1ccccc1] | (CDCl₃) δ: 7.46-7.22 (12H, m), 6.96 (2H, d, J = 8.4 Hz), 5.07 (2H, s), 4.56 (1H, dd, J = 8.4, 3.6 Hz), 4.48 (1H, d, J = 11.2 Hz), 4.31 (1H, d, J = 11.2 Hz), 3.54 (1H, dd, J = 13.0, 8.4 Hz), 3.17 (1H, dd, J = 13.0, 3.6 Hz). |
| 47 | 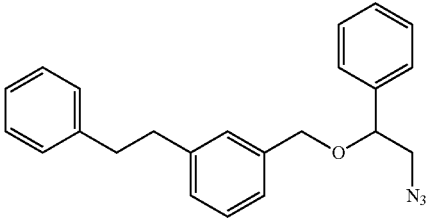 [SMILES: [N-]=[N+]=NCC(OCc1cccc(CCc2ccccc2)c1)c1ccccc1] | (CDCl₃) δ: 7.43-7.25 (7H, m), 7.24-7.10 (7H, m), 4.56 (1H, dd, J = 8.4, 3.7 Hz), 4.52 (1H, d, J = 11.7 Hz), 4.35 (1H, d, J = 11.7 Hz), 3.56 (1H, dd, J = 13.0, 8.4 Hz), 3.19 (1H, dd, J = 13.0, 3.7 Hz), 2.92 (4H, s). |
| 48 | 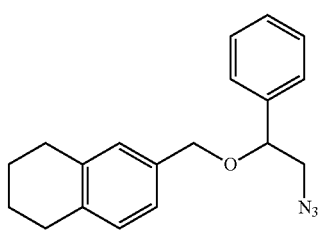 [SMILES: [N-]=[N+]=NCC(OCc1ccc2c(c1)CCCC2)c1ccccc1] | (CDCl₃) δ: 7.44-7.29 (5H, m), 7.14-6.99 (3H, m), 4.57 (1H, dd, J = 8.3, 3.6 Hz), 4.47 (1H, d, J = 11.2 Hz), 4.30 (1H, d, J = 11.2 Hz), 3.55 (1H, dd, J = 12.9, 8.3 Hz), 3.18 (1H, dd, J = 12.9, 3.6 Hz), 2.84-2.67 (4H, m), 1.86-1.72 (4H, m). |

TABLE 5-continued

| Reference Example | Structural formula | ¹H-NMR |
|---|---|---|
| 49 | | (CDCl₃) δ: 7.44-7.27 (8H, m), 7.16-7.11 (1H, m), 4.58 (1H, dd, J = 8.5, 3.6 Hz), 4.55 (1H, d, J = 11.7 Hz), 4.38 (1H, d, J = 11.7 Hz), 3.57 (1H, dd, J = 12.8, 8.5 Hz), 3.18 (1H, dd, J = 12.8, 3.6 Hz), 1.32 (9H, s). |
| 50 | | (CDCl₃) δ: 7.37-7.12 (10H, m), 7.06-7.00 (2H, m), 4.81 (1H, dd, J = 8.2, 4.0 Hz), 4.60 (1H, d, J = 11.6 Hz), 4.39 (1H, d, J = 11.6 Hz), 3.64 (1H, dd, J = 12.8, 8.2 Hz), 3.29 (1H, dd, J = 12.8, 4.0 Hz), 2.92 (4H, s). |

TABLE 6

| Reference Example | Structural formula | ¹H-NMR |
|---|---|---|
| 51 | | (CDCl₃) δ: 7.33-7.13 (9H, m), 6.84-6.79 (1H, m), 6.68-6.63 (1H, m), 4.70 (1H, dd, J = 8.1, 4.0 Hz), 4.60 (1H, d, J = 11.5 Hz), 4.37 (1H, d, J = 11.5 Hz), 3.61 (1H, dd, J = 12.8, 8.1 Hz), 3.27 (1H, dd, J = 12.8, 4.0 Hz), 2.92 (4H, s), 2.49 (3H, s). |
| 52 | | (CDCl₃) δ: 7.36-7.16 (13H, m), 4.53 (1H, d, J = 11.5 Hz), 4.53 (1H, dd, J = 8.3, 3.7 Hz), 4.35 (1H, d, J = 11.5 Hz), 3.52 (1H, dd, J = 13.0, 8.3 Hz), 3.18 (1H, dd, J = 13.0, 3.7 Hz), 2.92 (4H, s). |
| 53 | | (CDCl₃) δ: 7.44-7.10 (14H, m), 4.56 (1H, dd, J = 8.4, 3.6 Hz), 4.52 (1H, d, J = 11.5 Hz), 4.35 (1H, d, J = 11.5 Hz), 3.56 (1H, dd, J = 13.0, 8.4 Hz), 3.19 (1H, dd, J = 13.0, 3.6 Hz), 2.92 (4H, s). |

TABLE 6-continued

| Reference Example | Structural formula | ¹H-NMR |
|---|---|---|
| 54 | | (CDCl₃) δ: 7.40-7.11 (14H, m), 4.56 (1H, dd, J = 8.5, 3.6 Hz), 4.52 (1H, d, J = 11.7 Hz), 4.35 (1H, d, J = 11.7 Hz), 3.56 (1H, dd, J = 12.9, 8.5 Hz), 3.19 (1H, dd, J = 12.9, 3.6 Hz), 2.92 (4H, s). |
| 55 | | (CDCl₃) δ: 7.44-7.13 (14H, m), 4.57 (1H, dd, J = 8.4, 3.8 Hz), 4.52 (1H, d, J = 11.5 Hz), 4.35 (1H, d, J = 11.5 Hz), 3.55 (1H, dd, J = 12.9, 8.4 Hz), 3.19 (1H, dd, J = 12.9, 3.8 Hz), 2.92 (4H, s). |
| 56 | | (CDCl₃) δ: 7.43-7.13 (14H, m), 4.57 (1H, dd, J = 8.5, 3.6 Hz), 4.52 (1H, d, J = 11.4 Hz), 4.35 (1H, d, J = 11.4 Hz), 3.55 (1H, dd, J = 12.9, 8.5 Hz), 3.19 (1H, dd, J = 12.9, 3.6 Hz), 2.92 (4H, s). |
| 57 | | (CDCl₃) δ: 7.36-7.11 (13H, m), 4.53 (1H, dd, J = 8.3, 3.7 Hz), 4.53 (1H, d, J = 11.5 Hz), 4.35 (1H, d, J = 11.5 Hz), 3.52 (1H, dd, J = 13.0, 8.3 Hz), 3.18 (1H, dd, J = 13.0, 3.7 Hz), 2.93-2.90 (4H, m). |

TABLE 7

| Reference Example | Structural formula | ¹H-NMR |
|---|---|---|
| 58 | (structure with 4-fluorophenyl, CH(OCH₂-C₆H₄-CH₂CH₂-C₆H₅)CH₂N₃) | (CDCl₃) δ: 7.35-7.16 (11H, m), 7.14-7.05 (2H, m), 4.54 (1H, dd, J = 8.3, 3.8 Hz), 4.49 (1H, d, J = 11.5 Hz), 4.33 (1H, d, J = 11.5 Hz), 3.53 (1H, dd, J = 13.0, 8.3 Hz), 3.17 (1H, dd, J = 13.0, 3.8 Hz), 2.93-2.90 (4H, m). |
| 59 | (structure with 3-chlorophenyl, CH(O-CH₂-thienyl-CH₂CH₂-C₆H₅)CH₂N₃) | (CDCl₃) δ: 7.35-7.19 (9H, m), 6.74 (1H, d, J = 3.5 Hz), 6.62 (1H, d, J = 3.5 Hz), 4.65 (1H, d, J = 12.2 Hz), 4.56 (1H, dd, J = 8.2, 3.8 Hz), 4.45 (1H, d, J = 12.2 Hz), 3.50 (1H, dd, J = 13.0, 8.2 Hz), 3.18 (1H, dd, J = 13.0, 3.8 Hz), 3.14-3.08 (2H, m), 3.02-2.95 (2H, m). |
| 60 | (structure with phenyl, CH(O-CH₂-thienyl-CH₂CH₂-C₆H₅)CH₂N₃) | (CDCl₃) δ: 7.43-7.27 (7H, m), 7.25-7.16 (3H, m), 6.74 (1H, d, J = 3.4 Hz), 6.62 (1H, d, J = 3.4 Hz), 4.63 (1H, d, J = 12.3 Hz), 4.59 (1H, dd, J = 8.3, 3.8 Hz), 4.44 (1H, d, J = 12.3 Hz), 3.54 (1H, dd, J = 12.9, 8.3 Hz), 3.19 (1H, dd, J = 12.9, 3.8 Hz), 3.13-3.07 (2H, m), 3.01-2.95 (2H, m). |
| 61 | (structure with 3-thienyl, CH(OCH₂-C₆H₄-CH₂CH₂-C₆H₅)CH₂N₃) | (CDCl₃) δ: 7.36 (1H, dd, J = 4.9, 2.9 Hz), 7.32-7.13 (10H, m), 7.09 (1H, dd, J = 4.9, 1.3 Hz), 4.67 (1H, dd, J = 8.2, 3.8 Hz), 4.54 (1H, d, J = 11.5 Hz), 4.37 (1H, d, J = 11.5 Hz), 3.58 (1H, dd, J = 12.8, 8.2 Hz), 3.24 (1H, dd, J = 12.8, 3.8 Hz), 2.92 (4H, s). |
| 62 | (structure with 5-chlorothienyl, CH(OCH₂-C₆H₄-CH₂CH₂-C₆H₅)CH₂N₃) | (CDCl₃) δ: 7.34-7.12 (9H, m), 6.82 (1H, d, J = 3.8 Hz), 6.80 (1H, d, J = 3.8 Hz), 4.67 (1H, dd, J = 7.8, 4.1 Hz), 4.62 (1H, d, J = 11.5 Hz), 4.40 (1H, d, J = 11.5 Hz), 3.57 (1H, dd, J = 12.9, 7.8 Hz), 3.29 (1H, dd, J = 12.9, 4.1 Hz), 2.92 (4H, s). |

TABLE 7-continued

| Reference Example | Structural formula | ¹H-NMR |
|---|---|---|
| 63 | | (CDCl$_3$) δ: 7.33-7.23 (4H, m), 7.23-7.13 (5H, m), 6.81 (1H, d, J = 3.5 Hz), 6.65 (1H, d, J = 3.5 Hz), 4.70 (1H, dd, J = 8.1, 4.0 Hz), 4.59 (1H, d, J = 11.7 Hz), 4.37 (1H, d, J = 11.7 Hz), 3.61 (1H, dd, J = 12.8, 8.1 Hz), 3.28 (1H, dd, J = 12.8, 4.0 Hz), 2.92 (4H, s), 2.49 (3H, s). |

TABLE 8

| Reference Example | Structural formula | ¹H-NMR |
|---|---|---|
| 64 | | (CDCl$_3$) δ: 7.38-7.35 (2H, m), 7.34-7.28 (3H, m), 7.27-7.20 (2H, m), 7.13 (1H, dt, J = 7.1, 1.5 Hz), 4.56 (1H, d, J = 11.7 Hz), 4.54 (1H, dd, J = 8.4, 3.6 Hz), 4.39 (1H, d, J = 11.7 Hz), 3.54 (1H, dd, J = 13.0, 8.4 Hz), 3.17 (1H, dd, J = 13.0, 3.6 Hz), 1.31 (9H, s). |
| 65 | | (CDCl$_3$) δ: 7.38-7.22 (8H, m), 7.15-7.07 (1H, m), 7.03-6.96 (4H, m), 4.55 (1H, dd, J = 8.4, 3.7 Hz), 4.52 (1H, d, J = 11.5 Hz), 4.37 (1H, d, J = 11.5 Hz), 3.53 (1H, dd, J = 13.0, 8.4 Hz), 3.19 (1H, dd, J = 13.0, 3.7 Hz). |
| 66 | | (CDCl$_3$) δ: 7.43-7.30 (5H, m), 7.27-7.13 (4H, m), 4.57 (1H, dd, J = 8.4, 3.7 Hz), 4.51 (1H, d, J = 11.5 Hz), 4.34 (1H, d, J = 11.5 Hz), 3.55 (1H, dd, J = 13.0, 8.4 Hz), 3.18 (1H, dd, J = 13.0, 3.7 Hz), 2.66-2.56 (2H, m), 1.82-1.59 (4H, m), 1.55-1.44 (2H, m), 1.33-1.13 (5H, m), 1.01-0.84 (2H, m). |
| 67 | | (CDCl$_3$) δ: 7.43-7.31 (5H, m), 7.27-7.14 (4H, m), 4.57 (1H, dd, J = 8.6, 3.7 Hz), 4.51 (1H, d, J = 11.5 Hz), 4.34 (1H, d, J = 11.5 Hz), 3.55 (1H, dd, J = 12.9, 8.6 Hz), 3.18 (1H, dd, J = 12.9, 3.7 Hz), 2.68-2.56 (2H, m), 1.86-1.70 (4H, m), 1.69-1.42 (5H, m), 1.21-1.03 (2H, m). |

TABLE 8-continued

| Reference Example | Structural formula | ¹H-NMR |
|---|---|---|
| 68 | | (CDCl₃) δ: 7.43-7.13 (13H, m), 4.57 (1H, dd, J = 8.3, 3.7 Hz), 4.52 (1H, d, J = 11.5 Hz), 4.35 (1H, d, J = 11.5 Hz), 3.56 (1H, dd, J = 13.0, 8.3 Hz), 3.19 (1H, dd, J = 13.0, 3.7 Hz), 2.92 (4H, s). |
| 69 | | (CDCl₃) δ: 7.52 (2H, d, J = 7.9 Hz), 7.44-7.20 (9H, m), 7.14 (2H, d, J = 7.9 Hz), 4.57 (1H, dd, J = 8.5, 3.6 Hz), 4.52 (1H, d, J = 11.5 Hz), 4.35 (1H, d, J = 11.5 Hz), 3.56 (1H, dd, J = 12.9, 8.5 Hz), 3.19 (1H, dd, J = 12.9, 3.6 Hz), 3.04-2.87 (4H, m). |

TABLE 9

| Reference Example | Structural formula | ¹H-NMR |
|---|---|---|
| 70 | | (CDCl₃) δ: 7.45-7.24 (8H, m), 7.04-6.88 (5H, m), 4.59 (1H, dd, J = 8.6, 3.6 Hz), 4.51 (1H, d, J = 11.5 Hz), 4.36 (1H, d, J = 11.5 Hz), 3.57 (1H, dd, J = 13.1, 8.6 Hz), 3.20 (1H, dd, J = 13.1, 3.6 Hz). |
| 71 | | (CDCl₃) δ: 7.43-7.18 (10H, m), 6.73 (1H, d, J = 3.3 Hz), 6.61 (1H, d, J = 3.3 Hz), 4.63 (1H, d, J = 12.3 Hz), 4.60-4.58 (1H, m), 4.44 (1H, d, J = 12.3 Hz), 3.53 (1H, dd, J = 12.9, 8.3 Hz), 3.18 (1H, dd, J = 12.9, 3.8 Hz), 3.13-3.07 (2H, m), 3.02-2.95 (2H, m). |

TABLE 9-continued

| Reference Example | Structural formula | ¹H-NMR |
|---|---|---|
| 72 | | (CDCl₃) δ: 7.55-7.23 (12H, m), 4.63 (1H, dd, J = 8.4, 3.7 Hz), 4.62 (1H, d, J = 12.1 Hz), 4.46 (1H, d, J = 12.1 Hz), 3.57 (1H, dd, J = 13.0, 8.4 Hz), 3.23 (1H, dd, J = 13.0, 3.7 Hz), 1.36 (9H, s). |
| 73 | | (CDCl₃) δ: 7.44-7.13 (8H, m), 6.99-6.81 (5H, m), 4.59 (1H, dd, J = 8.4, 3.7 Hz), 4.55 (1H, d, J = 11.7 Hz), 4.42 (1H, d, J = 11.7 Hz), 3.54 (1H, dd, J = 12.8, 8.4 Hz), 3.20 (1H, dd, J = 12.8, 3.7 Hz), 2.93-2.89 (4H, m). |
| 74 | | (CDCl₃) δ: 7.45-7.31 (6H, m), 7.18 (2H, d, J = 1.8 Hz), 4.59 (1H, dd, J = 8.7, 3.4 Hz), 4.54 (1H, d, J = 11.5 Hz), 4.38 (1H, d, J = 11.5 Hz), 3.57 (1H, dd, J = 12.9, 8.7 Hz), 3.16 (1H, dd, J = 12.9, 3.4 Hz), 1.32 (18H, s). |
| 75 | | (CDCl₃) δ: 7.43-7.32 (5H, m), 7.25 (2H, d, J = 8.1 Hz), 7.17 (2H, d, J = 8.1 Hz), 4.57 (1H, dd, J = 8.5, 3.7 Hz), 4.51 (1H, d, J = 11.5 Hz), 4.34 (1H, d, J = 11.5 Hz), 3.55 (1H, dd, J = 12.9, 8.5 Hz), 3.18 (1H, dd, J = 12.9, 3.7 Hz), 2.59-2.53 (2H, m), 1.52-1.46 (2H, m), 0.96 (9H, s). |

TABLE 10

| Reference Example | Structural formula | ¹H-NMR |
|---|---|---|
| 76 | | (CDCl₃) δ: 7.37-7.21 (8H, m), 7.00-6.91 (4H, m), 4.54 (1H, dd, J = 8.4, 3.7 Hz), 4.51 (1H, d, J = 11.5 Hz), 4.37 (1H, d, J = 11.5 Hz), 3.53 (1H, dd, J = 13.0, 8.4 Hz), 3.20 (1H, dd, J = 13.0, 3.7 Hz). |
| 77 | | (CDCl₃) δ: 7.41-7.11 (7H, m), 4.55 (1H, d, J = 11.4 Hz), 4.54 (1H, dd, J = 8.2, 3.7 Hz), 4.40 (1H, d, J = 11.4 Hz), 3.54 (1H, dd, J = 13.0, 8.2 Hz), 3.16 (1H, dd, J = 13.0, 3.7 Hz), 1.32 (18H, s). |
| 78 | | (CDCl₃) δ: 7.60 (2H, d, J = 9.0 Hz), 7.45-7.32 (7H, m), 7.08-6.98 (4H, m), 4.60 (1H, dd, J = 8.7, 3.5 Hz), 4.53 (1H, d, J = 11.6 Hz), 4.41 (1H, d, J = 11.6 Hz), 3.58 (1H, dd, J = 13.0, 8.7 Hz), 3.22 (1H, dd, J = 13.0, 3.5 Hz). |
| 79 | | (CDCl₃) δ: 7.47-7.29 (6H, m), 4.67 (1H, dd, J = 12.3, 0.9 Hz), 4.58 (1H, dd, J = 8.6, 3.9 Hz), 4.52 (1H, dd, J = 12.3, 0.9 Hz), 3.53 (1H, dd, J = 13.0, 8.6 Hz), 3.20 (1H, dd, J = 13.0, 3.9 Hz), 1.44 (9H, d, J = 2.0 Hz). |
| 80 | | (CDCl₃) δ: 7.45-7.27 (6H, m), 6.96 (2H, d, J = 8.8 Hz), 6.77 (1H, ddd, J = 8.4, 2.4, 0.6 Hz), 6.66 (1H, dd, J = 11.0, 2.4 Hz), 4.59 (1H, dd, J = 8.4, 3.7 Hz), 4.54 (1H, d, J = 11.9 Hz), 4.42 (1H, d, J = 11.9 Hz), 3.54 (1H, dd, J = 13.0, 8.4 Hz), 3.20 (1H, dd, J = 13.0, 3.7 Hz). |
| 81 | | (CDCl₃) δ: 7.37-7.29 (3H, m), 7.26-7.21 (3H, m), 6.75 (1H, d, J = 3.5 Hz), 6.67 (1H, d, J = 3.5 Hz), 4.64 (1H, dd, J = 12.3, 0.6 Hz), 4.56 (1H, dd, J = 8.1, 4.0 Hz), 4.47 (1H, dd, J = 12.3, 0.6 Hz), 3.51 (1H, dd, J = 12.9, 8.1 Hz), 3.20 (1H, dd, J = 12.9, 4.0 Hz), 1.37 (9H, s). |

Reference Example 82

(1R)-2-Azido-1-(3-chlorophenyl)ethyl 6-cyclopropylbenzo[b]thiophen-2-yl ether Reference Example 32 (215 mg) was dissolved in dichloromethane (4.0 mL), thionyl chloride (151 μL) was added, and the reaction solution was stirred at room temperature for 2 hours. The solvent and the reagents were evaporated under reduced pressure to yield a crude product (a brown oil). (1R)-2-Azido-1-(3-chlorophenyl) ethanol (198 mg) was dissolved in DMF (4.0 mL), sodium hydride (48 mg) was added under ice cooling, and the reaction solution was stirred at the same temperature for 5 minutes. The crude product was added at the same temperature, and the reaction solution was stirred at room temperature for 2 hours. The reaction solution was quenched with water, and extracted with ethyl acetate and the solvent was evaporated under reduced pressure. The residue was purified by silica gel column chromatography (3 to 20% ethyl acetate/hexane) to yield the title compound (240 mg) as a pale yellow oil.

$^1$H-NMR(CDCl$_3$) δ: 7.60 (1H, d, J=8.2 Hz), 7.53 (1H, s), 7.38-7.30 (4H, m), 7.10-7.04 (2H, m), 4.79 (1H, dd, J=12.7, 1.0 Hz), 4.60 (1H, dd, J=8.0, 3.8 Hz), 4.58 (1H, dd, J=12.7, 1.0 Hz), 3.53 (1H, dd, J=13.0, 8.0 Hz), 3.26-3.18 (1H, m), 3.22 (1H, dd, J=13.0, 3.8 Hz), 2.04-1.96 (1H, m), 1.04-0.97 (2H, m), 0.79-0.72 (2H, m).

The compounds of Reference Examples 83 and 84 manufactured with a similar method to that of Reference Example 82 using corresponding raw materials or Reference Example compounds are shown in Table 11.

TABLE 11

| Reference Example | Structural formula | $^1$H-NMR |
|---|---|---|
| 83 | (structure) | (CDCl$_3$) δ: 7.80 (1H, d, J = 1.8 Hz), 7.63 (1H, d, J = 8.4 Hz), 7.38-7.33 (3H, m), 7.31 (1H, dd, J = 8.4, 1.8 Hz), 7.26-7.22 (1H, m), 7.13 (1H, s), 4.79 (1H, dd, J = 12.7, 1.0 Hz), 4.61 (1H, d, J = 12.7 Hz), 4.60 (1H, dd, J = 8.1, 3.8 Hz), 3.54 (1H, dd, J = 13.0, 8.1 Hz), 3.23 (1H, dd, J = 13.0, 3.8 Hz). |
| 84 | (structure) | (CDCl$_3$) δ: 7.36-7.30 (3H, m), 7.15-7.09 (3H, m), 7.01-6.97 (2H, m), 6.64 (1H, d, J = 3.8 Hz), 6.33 (1H, d, J = 3.8 Hz), 4.59 (1H, d, J = 12.5 Hz), 4.57 (1H, dd, J = 8.1, 3.8 Hz), 4.41 (1H, d, J = 12.5 Hz), 3.50 (1H, dd, J = 13.0, 8.1 Hz), 3.19 (1H, dd, J = 13.0, 3.8 Hz), 2.33 (3H, s). |

Reference Example 85

2-(4-tert-Butylbenzyloxy)-2-phenylethyl amine

Reference Example 43 (600 mg) was dissolved in THF-water mixed solution (9:1, 10.0 mL), and triphenylphosphine (661 mg) was added, and the reaction solution was stirred at room temperature for 19 hours. The solvent was evaporated under reduced pressure, and the residue was extracted with chloroform, and washed with water and saturated brine. The combined organic layer was dried over anhydrous sodium sulfate, and then the solvent was evaporated under reduced pressure, and the residue was purified by silica gel column chromatography (1 to 9% methanol/chloroform) to yield the title compound (185 mg) as a colorless oil.

$^1$H-NMR(CDCl$_3$) δ: 7.42-7.23 (9H, m), 4.49 (1H, d, J=11.4 Hz), 4.36 (1H, dd, J=7.8, 4.3 Hz), 4.29 (1H, d, J=11.4 Hz), 2.96 (1H, dd, J=13.3, 7.8 Hz), 2.86 (1H, dd, J=13.3, 4.3 Hz), 1.32 (9H, s).

The compounds of Reference Examples 86 to 97 manufactured with a similar method to that of Reference Example 85 using the compounds of Reference Examples 44 to 51 and Reference Examples 53 to 56 are shown in Tables 12 and 13.

TABLE 12

| Reference Example | Structural formula | $^1$H-NMR |
|---|---|---|
| 86 | (structure) | (CDCl$_3$) δ: 7.38-7.31 (7H, m), 7.23-7.15 (7H, m), 4.50 (1H, d, J = 11.5 Hz), 4.34 (1H, dd, J = 7.7, 4.2 Hz), 4.28 (1H, d, J = 11.5 Hz), 2.96 (1H, dd, J = 13.4, 7.7 Hz), 2.92 (4H, s), 2.85 (1H, dd, J = 13.4, 4.2 Hz). |

TABLE 12-continued

| Reference Example | Structural formula | ¹H-NMR |
|---|---|---|
| 87 | 4-chlorophenyl-CH(OCH₂-[4-(2-phenylethyl)phenyl])-CH₂NH₂ | (CDCl₃) δ: 7.37-7.15 (13H, m), 4.47 (1H, d, J = 11.5 Hz), 4.31 (1H, dd, J = 8.2, 4.9 Hz), 4.27 (1H, d, J = 11.5 Hz), 2.93 (1H, dd, J = 13.6, 8.2 Hz), 2.92 (4H, s), 2.82 (1H, dd, J = 13.6, 4.9 Hz). |
| 88 | phenyl-CH(OCH₂-[4-(benzyloxy)phenyl])-CH₂NH₂ | (CDCl₃) δ: 7.47-7.21 (12H, m), 6.95 (2H, d, J = 8.8 Hz), 5.07 (2H, s), 4.45 (1H, d, J = 11.4 Hz), 4.33 (1H, dd, J = 7.7, 4.2 Hz), 4.24 (1H, d, J = 11.4 Hz), 2.95 (1H, dd, J = 13.3, 7.7 Hz), 2.84 (1H, dd, J = 13.3, 4.2 Hz). |
| 89 | phenyl-CH(OCH₂-[3-(2-phenylethyl)phenyl])-CH₂NH₂ | (CDCl₃) δ: 7.41-7.28 (6H, m), 7.22-7.18 (6H, m), 7.13-7.12 (2H, m), 4.49 (1H, d, J = 11.5 Hz), 4.32 (1H, dd, J = 8.2, 4.2 Hz), 4.28 (1H, d, J = 11.5 Hz), 2.96 (1H, dd, J = 13.4, 8.2 Hz), 2.92 (4H, s), 2.85 (1H, dd, J = 13.4, 4.2 Hz). |
| 90 | phenyl-CH(OCH₂-[5,6,7,8-tetrahydronaphthalen-2-yl])-CH₂NH₂ | (CDCl₃) δ: 7.44-7.24 (5H, m), 7.06-6.99 (3H, m), 4.44 (1H, d, J = 11.2 Hz), 4.35 (1H, dd, J = 7.7, 4.3 Hz), 4.23 (1H, d, J = 11.2 Hz), 2.95 (1H, dd, J = 13.3, 7.7 Hz), 2.85 (1H, dd, J = 13.3, 4.3 Hz), 2.81-2.71 (4H, m), 1.85-1.74 (4H, m). |
| 91 | phenyl-CH(OCH₂-[3-tert-butylphenyl])-CH₂NH₂ | (CDCl₃) δ: 7.43-7.24 (8H, m), 7.18-7.12 (1H, m), 4.52 (1H, d, J = 11.5 Hz), 4.35 (1H, dd, J = 7.7, 4.2 Hz), 4.31 (1H, d, J = 11.5 Hz), 2.97 (1H, dd, J = 13.4, 7.7 Hz), 2.86 (1H, dd, J = 13.4, 4.2 Hz), 1.32 (9H, s). |

TABLE 12-continued

| Reference Example | Structural formula | ¹H-NMR |
| --- | --- | --- |
| 92 | (structure) | (CDCl₃) δ: 7.34-7.13 (10H, m), 7.04-6.99 (2H, m), 4.61 (1H, dd, J = 7.3, 4.8 Hz), 4.57 (1H, d, J = 11.6 Hz), 4.34 (1H, d, J = 11.6 Hz), 3.07 (1H, dd, J = 12.6, 7.3 Hz), 2.95 (1H, dd, J = 12.6, 4.8 Hz), 2.91 (4H, s). |

TABLE 13

| Reference Example | Structural formula | ¹H-NMR |
| --- | --- | --- |
| 93 | (structure) | (CDCl₃) δ: 7.32-7.13 (9H, m), 6.79 (1H, d, J = 3.3 Hz), 6.68-6.61 (1H, m), 4.57 (1H, d, J = 11.4 Hz), 4.52-4.44 (1H, m), 4.32 (1H, d, J = 11.4 Hz), 3.11-2.81 (2H, m), 2.91 (4H, s), 2.49 (3H, s). |
| 94 | (structure) | (CDCl₃) δ: 7.73-7.10 (14H, m), 4.49 (1H, d, J = 11.5 Hz), 4.32 (1H, dd, J = 7.7, 4.3 Hz), 4.28 (1H, d, J = 11.5 Hz), 2.96 (1H, dd, J = 13.4, 7.7 Hz), 2.92 (4H, s), 2.85 (1H, dd, J = 13.4, 4.3 Hz). |
| 95 | (structure) | (CDCl₃) δ: 7.41-7.12 (14H, m), 4.49 (1H, d, J = 11.5 Hz), 4.33 (1H, dd, J = 7.7, 4.2 Hz), 4.28 (1H, d, J = 11.5 Hz), 2.96 (1H, dd, J = 13.4, 7.7 Hz), 2.92 (4H, s), 2.85 (1H, dd, J = 13.4, 4.2 Hz). |
| 96 | (structure) | (CDCl₃) δ: 7.43-7.10 (14H, m), 4.50 (1H, d, J = 11.4 Hz), 4.35 (1H, dd, J = 7.8, 4.2 Hz), 4.28 (1H, d, J = 11.4 Hz), 2.96 (1H, dd, J = 13.4, 7.8 Hz), 2.92 (4H, s), 2.85 (1H, dd, J = 13.4, 4.2 Hz). |

TABLE 13-continued

| Reference Example | Structural formula | ¹H-NMR |
|---|---|---|
| 97 | [structure: 1-[4-(2-phenylethyl)benzyl]oxy-2-phenyl-ethylamine] | (CDCl$_3$) δ: 7.43-7.14 (14H, m), 4.50 (1H, d, J = 11.4 Hz), 4.35 (1H, dd, J = 7.7, 4.2 Hz), 4.28 (1H, d, J = 11.4 Hz), 2.96 (1H, dd, J = 13.4, 7.7 Hz), 2.92 (4H, s), 2.86 (1H, dd, J = 13.4, 4.2 Hz). |

Reference Example 98

1-(2-Bromoethyl)-4-(2-phenylethyl)benzene

The title compound (446 mg) was manufactured as an orange powder from 2-[4-(2-phenylethyl)phenyl] ethanol (600 mg) with a similar method to that of Reference Example 42.

¹H-NMR(CDCl$_3$) δ: 7.31-7.26 (2H, m), 7.21-7.16 (3H, m), 7.15-7.09 (4H, m), 3.55 (2H, t, J=7.7 Hz), 3.13 (2H, t, J=7.7 Hz), 2.91 (4H, s).

Reference Example 99

4-(4-(2-Phenylethyl)phenyl)-2-phenyl butyronitrile

The title compound (497 mg) was manufactured as a colorless oil using Reference Example 98 (732 mg) and phenyl acetonitrile (269 mg) with a similar method to that of Reference Example 43.

¹H-NMR(CDCl$_3$) δ: 7.41-7.27 (6H, m), 7.21-7.08 (8H, m), 3.73 (1H, dd, J=8.9, 6.1 Hz), 2.90 (4H, s), 2.82-2.74 (2H, m), 2.32-2.04 (2H, m).

Reference Example 100

4-(4-(2-Phenylethyl)phenyl)-2-phenylbutyl amine

The title compound (321 mg) was manufactured as a colorless oil from Reference Example 99 (490 mg) with a similar method to that of Reference Example 21.

¹H-NMR(CDCl$_3$) δ: 7.37-7.23 (5H, m), 7.22-7.16 (5H, m), 7.08 (2H, d, J=8.1 Hz), 7.02 (2H, d, J=8.1 Hz), 2.96-2.81 (2H, m), 2.89 (4H, s), 2.65-2.38 (3H, m), 2.04-1.84 (2H, m), 1.41-1.25 (2H, m).

Reference Example 101

Methyl 4-{[N-[2-(4-tert-butylbenzyloxy)-2-phenyl-ethyl]amino]methyl} benzoate

Reference Example 85 (180 mg) and methyl terephthalaldehydate (104 mg) were dissolved in THF (5.0 mL), acetic acid (91 μL) was added, and the reaction solution was stirred at room temperature for 30 minutes. Then, sodium triacetoxyborohydride (403 mg) was added, and then the reaction solution was stirred at the same temperature for 16 hours. The solvent was evaporated under reduced pressure, and a saturated aqueous solution of sodium hydrogen carbonate was added. The reaction solution was stirred, and then extracted with ethyl acetate, and washed with water and saturated brine. The combined organic layer was dried over anhydrous sodium sulfate, and then the solvent was evaporated under reduced pressure, and the residue was purified by silica gel column chromatography (6 to 50% ethyl acetate/hexane) to yield the title compound (259 mg) as a colorless oil.

¹H-NMR(CDCl$_3$) δ: 7.97 (2H, d, J=8.2 Hz), 7.39-7.21 (11H, m), 4.58 (1H, dd, J=9.0, 3.7 Hz), 4.46 (1H, d, J=11.4 Hz), 4.27 (1H, d, J=11.4 Hz), 3.90 (3H, s), 3.84 (1H, d, J=13.8 Hz), 3.79 (1H, d, J=13.8 Hz), 2.95 (1H, dd, J=12.3, 9.0 Hz), 2.73 (1H, dd, J=12.3, 3.7 Hz), 1.31 (9H, s).

The compounds of Reference Examples 102 to 114 manufactured with a similar method to that of Reference Example 101 using Reference Examples 86 to 97 and Reference Example 100 are shown in Tables 14 to 16.

TABLE 14

| Reference Example | Structural formula | ¹H-NMR |
|---|---|---|
| 102 | [structure] | (CDCl$_3$) δ: 7.98 (2H, d, J = 8.2 Hz), 7.40-7.36 (5H, m), 7.33-7.14 (11H, m), 4.57 (1H, dd, J = 8.9, 3.8 Hz), 4.47 (1H, d, J = 11.5 Hz), 4.27 (1H, d, J = 11.5 Hz), 3.90 (3H, s), 3.85 (1H, d, J = 14.0 Hz), 3.79 (1H, d, J = 14.0 Hz), 2.95 (1H, dd, J = 12.4, 8.9 Hz), 2.91 (4H, s), 2.73 (1H, dd, J = 12.4, 3.8 Hz). |

TABLE 14-continued

| Reference Example | Structural formula | ¹H-NMR |
|---|---|---|
| 103 | | (CDCl₃) δ: 7.98 (2H, d, J = 8.4 Hz), 7.35-7.33 (4H, m), 7.29-7.28 (3H, m), 7.26 (1H, s), 7.20-7.16 (7H, m), 4.53 (1H, dd, J = 8.9, 3.8 Hz), 4.44 (1H, d, J = 11.4 Hz), 4.25 (1H, d, J = 11.4 Hz), 3.91 (3H, s), 3.84 (1H, d, J = 14.0 Hz), 3.78 (1H, d, J = 14.0 Hz), 2.91 (4H, s), 2.91 (1H, dd, J = 12.4, 8.9 Hz), 2.70 (1H, dd, J = 12.4, 3.8 Hz). |
| 104 | | (CDCl₃) δ: 7.97 (2H, d, J = 8.4 Hz), 7.44-7.26 (12H, m), 7.22 (2H, d, J = 8.6 Hz), 6.94 (2H, d, J = 8.6 Hz), 5.06 (2H, s), 4.57 (1H, dd, J = 9.0, 3.7 Hz), 4.42 (1H, d, J = 11.2 Hz), 4.22 (1H, d, J = 11.2 Hz), 3.90 (3H, s), 3.81 (2H, s), 2.93 (1H, dd, J = 12.4, 9.0 Hz), 2.73 (1H, dd, J = 12.4, 3.7 Hz). |
| 105 | | (CDCl₃) δ: 7.97 (2H, dd, J = 6.7, 1.7 Hz), 7.40-7.28 (10H, m), 7.23-7.16 (4H, m), 7.12 (2H, dd, J = 3.8, 1.8 Hz), 4.57 (1H, dd, J = 8.9, 3.8 Hz), 4.47 (1H, d, J = 11.5 Hz), 4.27 (1H, d, J = 11.5 Hz), 3.90 (3H, s), 3.85 (1H, d, J = 14.0 Hz), 3.80 (1H, d, J = 14.0 Hz), 2.96 (1H, dd, J = 12.4, 8.9 Hz), 2.90 (4H, s), 2.74 (1H, dd, J = 12.4, 3.8 Hz). |
| 106 | | (CDCl₃) δ: 7.97 (2H, d, J = 8.1 Hz), 7.46-7.22 (7H, m), 7.03-6.97 (3H, m), 4.57 (1H, dd, J = 8.9, 3.8 Hz), 4.42 (1H, d, J = 11.2 Hz), 4.21 (1H, d, J = 11.2 Hz), 3.90 (3H, s), 3.84 (1H, d, J = 13.7 Hz), 3.79 (1H, d, J = 13.7 Hz), 2.94 (1H, dd, J = 12.5, 8.9 Hz), 2.78-2.68 (5H, m), 1.82-1.75 (4H, m). |

TABLE 15

| Reference Example | Structural formula | ¹H-NMR |
|---|---|---|
| 107 | | (CDCl₃) δ: 8.00-7.93 (2H, m), 7.42-7.21 (10H, m), 7.16-7.10 (1H, m), 4.58 (1H, dd, J = 9.0, 3.7 Hz), 4.49 (1H, d, J = 11.4 Hz), 4.30 (1H, d, J = 11.4 Hz), 3.91 (3H, s), 3.83 (2H, s), 2.96 (1H, dd, J = 12.4, 9.0 Hz), 2.74 (1H, dd, J = 12.4, 3.7 Hz), 1.29 (9H, s). |

TABLE 15-continued

| Reference Example | Structural formula | ¹H-NMR |
|---|---|---|
| 108 | | (CDCl₃) δ: 7.98 (2H, d, J = 8.2 Hz), 7.40-7.12 (12H, m), 7.06-6.96 (2H, m), 4.82 (1H, dd, J = 8.3, 4.1 Hz), 4.54 (1H, d, J = 11.4 Hz), 4.31 (1H, d, J = 11.4 Hz), 3.91 (3H, s), 3.85 (1H, d, J = 14.1 Hz), 3.80 (1H, d, J = 14.1 Hz), 3.07 (1H, dd, J = 12.1, 8.3 Hz), 2.91 (4H, s), 2.84 (1H, dd, J = 12.1, 4.1 Hz). |
| 109 | | (CDCl₃) δ: 7.98 (2H, d, J = 8.2 Hz), 7.39-7.12 (11H, m), 6.80 (1H, d, J = 3.5 Hz), 6.65-6.61 (1H, m), 4.71 (1H, dd, J = 8.3, 4.3 Hz), 4.54 (1H, d, J = 11.5 Hz), 4.30 (1H, d, J = 11.5 Hz), 3.91 (3H, s), 3.85 (1H, d, J = 14.1 Hz), 3.79 (1H, d, J = 14.1 Hz), 3.04 (1H, dd, J = 12.0, 8.3 Hz), 2.91 (4H, s), 2.82 (1H, dd, J = 12.0, 4.3 Hz), 2.48 (3H, s). |
| 110 | | (CDCl₃) δ: 7.99-7.93 (2H, m), 7.37-7.08 (16H, m), 4.57 (1H, dd, J = 8.9, 3.8 Hz), 4.47 (1H, d, J = 11.5 Hz), 4.27 (1H, d, J = 11.5 Hz), 3.90 (3H, s), 3.86 (1H, d, J = 13.7 Hz), 3.80 (1H, d, J = 13.7 Hz), 3.02-2.84 (5H, m), 2.74 (1H, dd, J = 12.4, 3.8 Hz). |
| 111 | | (CDCl₃) δ: 7.97 (2H, d, J = 8.4 Hz), 7.40-7.11 (16H, m), 4.57 (1H, dd, J = 8.9, 3.8 Hz), 4.47 (1H, d, J = 11.4 Hz), 4.27 (1H, d, J = 11.4 Hz), 3.90 (3H, s), 3.85 (1H, d, J = 13.7 Hz), 3.83 (1H, d, J = 13.7 Hz), 2.96 (1H, dd, J = 12.3, 8.9 Hz), 2.89 (4H, s), 2.74 (1H, dd, J = 12.3, 3.8 Hz). |
| 112 | | (CDCl₃) δ: 8.00-7.94 (2H, m), 7.41-7.12 (16H, m), 4.57 (1H, dd, J = 9.1, 3.8 Hz), 4.46 (1H, d, J = 11.4 Hz), 4.27 (1H, d, J = 11.4 Hz), 3.90 (3H, s), 3.85 (1H, d, J = 13.8 Hz), 3.79 (1H, d, J = 13.8 Hz), 2.95 (1H, dd, J = 12.4, 9.1 Hz), 2.91 (4H, s), 2.73 (1H, dd, J = 12.4, 3.8 Hz). |

TABLE 16

| Reference Example | Structural formula | ¹H-NMR |
|---|---|---|
| 113 | | (CDCl$_3$) δ: 8.02-7.94 (2H, m), 7.47-7.08 (16H, m), 4.58 (1H, dd, J = 9.0, 3.7 Hz), 4.46 (1H, d, J = 11.4 Hz), 4.27 (1H, d, J = 11.4 Hz), 3.90 (3H, s), 3.85 (1H, d, J = 14.1 Hz), 3.80 (1H, d, J = 14.1 Hz), 2.94 (1H, dd, J = 12.4, 9.0 Hz), 2.91 (4H, s), 2.74 (1H, dd, J = 12.4, 3.7 Hz). |
| 114 | | (CDCl$_3$) δ: 7.95 (2H, d, J = 8.1 Hz), 7.37-7.24 (7H, m), 7.21-7.17 (5H, m), 7.07 (2H, d, J = 7.9 Hz), 7.00 (2H, d, J = 7.9 Hz), 3.90 (3H, s), 3.79 (1H, d, J = 13.9 Hz), 3.73 (1H, d, J = 13.9 Hz), 2.92-2.85 (1H, m), 2.88 (4H, s), 2.84-2.75 (3H, m), 2.49-2.40 (2H, m), 2.00-1.84 (2H, m). |

Reference Example 115

Methyl 4-{[N-[2-(3-chlorophenyl)-2-[4-(2-phenylethyl)benzyloxy]ethyl]amino]methyl} benzoate Reference Example 57 (1.60 g) was dissolved in THF (26.0 mL), tri-n-butylphosphine (1.12 mL) was added, and the reaction solution was stirred at room temperature for 30 minutes. Then, methyl terephthalaldehydate (670 mg) was added and the reaction solution was stirred at the same temperature for 18 hours. Then, sodium borohydride (231 mg) and methanol (16.0 mL) was added, and the reaction solution was stirred at the same temperature for 3 hours. The reaction solution was quenched with a 1 mol/L aqueous solution of hydrochloric acid, and stirred, and then neutralized with a saturated aqueous solution of sodium hydrogen carbonate, and extracted with ethyl acetate. The combined organic layer was dried over anhydrous sodium sulfate, and then the solvent was evaporated under reduced pressure, and the residue was purified by silica gel column chromatography (20 to 60% ethyl acetate/hexane) to yield the title compound (1.99 g) as a pale yellow oil.

¹H-NMR(CDCl$_3$) δ: 8.06-7.96 (2H, m), 7.45-7.12 (15H, m), 4.53 (1H, dd, J=8.8, 3.5 Hz), 4.47 (1H, d, J=11.4 Hz), 4.27 (1H, d, J=11.4 Hz), 3.91 (3H, s), 3.83 (1H, d, J=14.1 Hz), 3.78 (1H, d, J=14.1 Hz), 2.91 (4H, s), 2.91 (1H, dd, J=12.5, 8.8 Hz), 2.71 (1H, dd, J=12.5, 3.7 Hz).

The compounds of Reference Examples 116 to 142 manufactured with a similar method to that of Reference Example 115 using the compounds of Reference Example 52 and Reference Examples 58 to 83 are shown in Tables 17 to 22.

TABLE 17

| Reference Example | Structural formula | ¹H-NMR |
|---|---|---|
| 116 | | (CDCl$_3$) δ: 7.98 (2H, d, J = 8.2 Hz), 7.37-7.27 (6H, m), 7.22-7.13 (7H, m), 7.08-7.02 (2H, m), 4.54 (1H, dd, J = 9.0, 3.7 Hz), 4.43 (1H, d, J = 11.3 Hz), 4.25 (1H, d, J = 11.3 Hz), 3.91 (3H, s), 3.84 (1H, d, J = 13.9 Hz), 3.79 (1H, d, J = 13.9 Hz), 2.92 (1H, dd, J = 12.2, 9.0 Hz), 2.91 (4H, s), 2.70 (1H, dd, J = 12.2, 3.7 Hz). |

TABLE 17-continued

| Reference Example | Structural formula | ¹H-NMR |
|---|---|---|
| 117 | 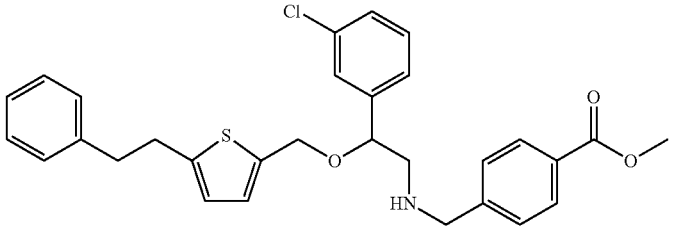 [SMILES: COC(=O)c1ccc(CNCC(OCc2ccc(CCc3ccccc3)s2)c2cccc(Cl)c2)cc1] | (CDCl₃) δ: 7.98 (2H, d, J = 8.4 Hz), 7.37-7.24 (7H, m), 7.23-7.19 (4H, m), 6.72 (1H, d, J = 3.5 Hz), 6.62 (1H, d, J = 3.5 Hz), 4.59 (1H, d, J = 12.3 Hz), 4.57 (1H, dd, J = 8.6, 3.7 Hz), 4.38 (1H, d, J = 12.3 Hz), 3.90 (3H, s), 3.81 (2H, s), 3.12-3.05 (2H, m), 2.99-2.85 (3H, m), 2.69 (1H, dd, J = 12.6, 3.7 Hz). |
| 118 | 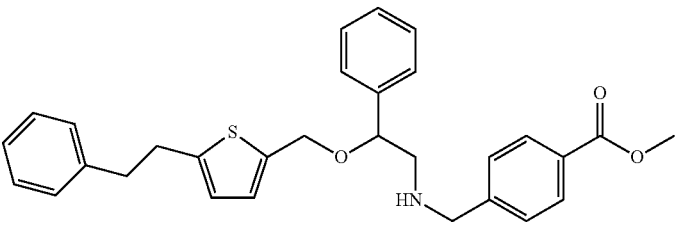 [SMILES: COC(=O)c1ccc(CNCC(OCc2ccc(CCc3ccccc3)s2)c2ccccc2)cc1] | (CDCl₃) δ: 7.98 (2H, dd, J = 6.5, 1.7 Hz), 7.45-7.25 (9H, m), 7.24-7.17 (3H, m), 6.71 (1H, d, J = 3.3 Hz), 6.61 (1H, d, J = 3.3 Hz), 4.60 (1H, dd, J = 8.8, 3.5 Hz), 4.58 (1H, d, J = 12.3 Hz), 4.38 (1H, d, J = 12.3 Hz), 3.89 (3H, s), 3.82 (2H, s), 3.11-3.05 (2H, m), 3.00-2.93 (2H, m), 2.94 (1H, dd, J = 12.5, 8.8 Hz), 2.72 (1H, dd, J = 12.5, 3.5 Hz). |
| 119 | 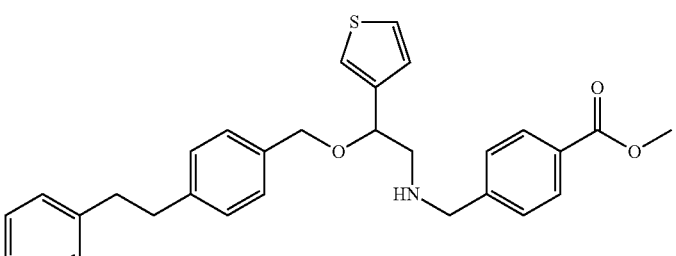 | (CDCl₃) δ: 7.98 (2H, d, J = 8.4 Hz), 7.38-7.12 (13H, m), 7.08 (1H, dd, J = 4.9, 1.1 Hz), 4.68 (1H, dd, J = 8.6, 4.0 Hz), 4.48 (1H, d, J = 11.4 Hz), 4.29 (1H, d, J = 11.4 Hz), 3.91 (3H, s), 3.85 (1H, d, J = 13.5 Hz), 3.79 (1H, d, J = 13.5 Hz), 3.00 (1H, dd, J = 12.2, 8.6 Hz), 2.91 (4H, s), 2.77 (1H, dd, J = 12.2, 4.0 Hz). |
| 120 | 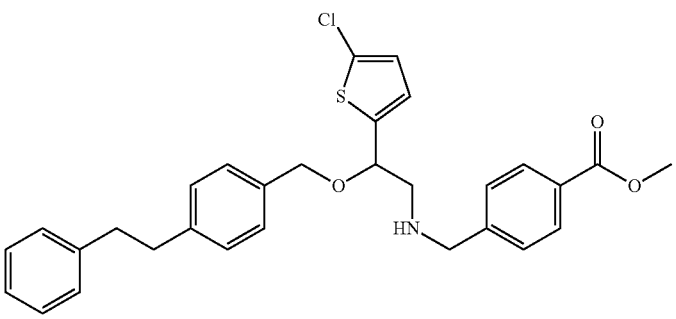 [SMILES: COC(=O)c1ccc(CNCC(OCc2ccc(CCc3ccccc3)cc2)c2ccc(Cl)s2)cc1] | (CDCl₃) δ: 7.99 (2H, d, J = 8.4 Hz), 7.49-7.10 (11H, m), 6.79 (1H, d, J = 6.0 Hz), 6.78 (1H, d, J = 6.0 Hz), 4.67 (1H, dd, J = 7.8, 4.0 Hz), 4.55 (1H, d, J = 11.4 Hz), 4.31 (1H, d, J = 11.4 Hz), 3.91 (3H, s), 3.82 (2H, s), 2.98 (1H, dd, J = 12.4, 7.8 Hz), 2.91 (4H, s), 2.84 (1H, dd, J = 12.4, 4.0 Hz). |

TABLE 18

| Reference Example | Structural formula | 1H-NMR |
|---|---|---|
| 121 | 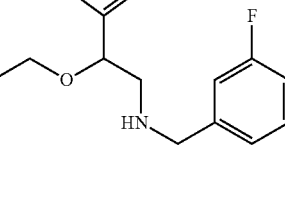 | (CDCl3) δ: 7.86 (1H, t, J = 7.7 Hz), 7.34-7.05 (11H, m), 6.80 (1H, d, J = 3.3 Hz), 6.64 (1H, d, J = 3.3 Hz), 4.70 (1H, dd, J = 8.0, 4.3 Hz), 4.55 (1H, d, J = 11.4 Hz), 4.30 (1H, d, J = 11.4 Hz), 3.92 (3H, s), 3.82 (1H, d, J = 14.6 Hz), 3.76 (1H, d, J = 14.6 Hz), 3.02 (1H, dd, J = 12.3, 8.0 Hz), 2.91 (4H, s), 2.80 (1H, dd, J = 12.3, 4.3 Hz), 2.48 (3H, s). |
| 122 | 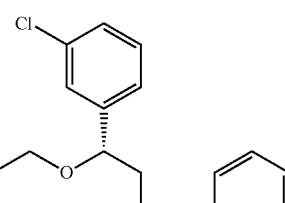 | (CDCl3) δ: 8.01-7.95 (2H, m), 7.37-7.14 (15H, m), 4.53 (1H, dd, J = 8.8, 3.8 Hz), 4.47 (1H, d, J = 11.4 Hz), 4.27 (1H, d, J = 11.4 Hz), 3.91 (3H, s), 3.83 (1H, d, J = 14.0 Hz), 3.78 (1H, d, J = 14.0 Hz), 2.91 (4H, s), 2.91 (1H, dd, J = 12.5, 8.8 Hz), 2.71 (1H, dd, J = 12.5, 3.8 Hz). |
| 123 | 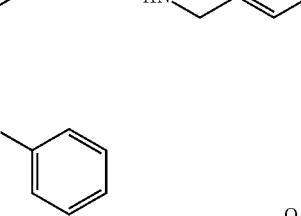 | (CDCl3) δ: 7.99-7.96 (2H, m), 7.36-7.20 (9H, m), 7.15-7.09 (1H, m), 4.54 (1H, dd, J = 8.9, 3.8 Hz), 4.50 (1H, d, J = 11.6 Hz), 4.30 (1H, d, J = 11.6 Hz), 3.91 (3H, s), 3.84 (1H, d, J = 14.3 Hz), 3.79 (1H, d, J = 14.3 Hz), 2.92 (1H, dd, J = 12.4, 8.9 Hz), 2.71 (1H, dd, J = 12.4, 3.8 Hz), 1.30 (9H, s). |
| 124 | 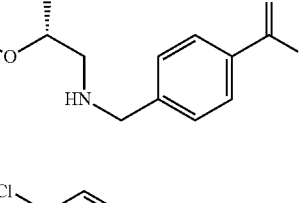 | (CDCl3) δ: 7.98 (2H, dt, J = 8.4, 1.5 Hz), 7.36-7.20 (10H, m), 7.11 (1H, tt, J = 7.3, 1.5 Hz), 7.02-6.94 (4H, m), 4.54 (1H, dd, J = 8.9, 3.8 Hz), 4.46 (1H, d, J = 11.4 Hz), 4.28 (1H, d, J = 11.4 Hz), 3.91 (3H, s), 3.85 (1H, d, J = 13.9 Hz), 3.79 (1H, d, J = 13.9 Hz), 2.92 (1H, dd, J = 12.4, 8.9 Hz), 2.71 (1H, dd, J = 12.4, 3.8 Hz). |
| 125 | 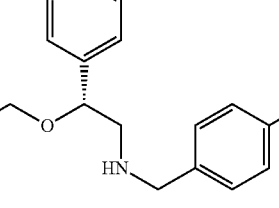 | (CDCl3) δ: 7.97 (2H, d, J = 8.4 Hz), 7.45-7.23 (7H, m), 7.21 (2H, d, J = 7.5 Hz), 7.14 (2H, d, J = 7.5 Hz), 4.57 (1H, dd, J = 8.8, 3.7 Hz), 4.45 (1H, d, J = 11.4 Hz), 4.25 (1H, d, J = 11.4 Hz), 3.91 (3H, s), 3.84 (1H, d, J = 13.2 Hz), 3.78 (1H, d, J = 13.2 Hz), 2.94 (1H, dd, J = 12.2, 8.8 Hz), 2.72 (1H, dd, J = 12.2, 3.7 Hz), 2.65-2.55 (2H, m), 1.83-1.57 (4H, m), 1.55-1.42 (2H, m), 1.33-1.09 (5H, m), 1.03-0.81 (2H, m). |

TABLE 19

| Reference Example | Structural formula | ¹H-NMR |
|---|---|---|
| 126 | | (CDCl$_3$) δ: 7.97 (2H, d, J = 8.2 Hz), 7.45-7.23 (7H, m), 7.21 (2H, d, J = 7.7 Hz), 7.15 (2H, d, J = 7.7 Hz), 4.58 (1H, dd, J = 9.0, 3.7 Hz), 4.46 (1H, d, J = 11.4 Hz), 4.26 (1H, d, J = 11.4 Hz), 3.91 (3H, s), 3.84 (1H, d, J = 13.7 Hz), 3.79 (1H, d, J = 13.7 Hz), 2.94 (1H, dd, J = 12.3, 9.0 Hz), 2.72 (1H, dd, J = 12.3, 3.7 Hz), 2.66-2.55 (2H, m), 1.88-1.41 (9H, m), 1.21-1.05 (2H, m). |
| 127 | | (CDCl$_3$) δ: 7.97 (2H, d, J = 8.1 Hz), 7.48-7.10 (15H, m), 4.57 (1H, dd, J = 8.9, 3.9 Hz), 4.46 (1H, d, J = 11.4 Hz), 4.26 (1H, d, J = 11.4 Hz), 3.90 (3H, s), 3.84 (1H, d, J = 11.9 Hz), 3.79 (1H, d, J = 11.9 Hz), 2.95 (1H, dd, J = 12.4, 8.9 Hz), 2.91 (4H, s), 2.73 (1H, dd, J = 12.4, 3.9 Hz). |
| 128 | | (CDCl$_3$) δ: 7.97 (2H, d, J = 8.1 Hz), 7.56-7.20 (13H, m), 7.13 (2H, d, J = 7.9 Hz), 4.57 (1H, dd, J = 8.8, 3.8 Hz), 4.46 (1H, d, J = 11.4 Hz), 4.27 (1H, d, J = 11.4 Hz), 3.90 (3H, s), 3.85 (1H, d, J = 13.0 Hz), 3.80 (1H, d, J = 13.0 Hz), 3.05-2.86 (5H, m), 2.73 (1H, dd, J = 12.3, 3.8 Hz). |
| 129 | | (CDCl$_3$) δ: 7.98 (2H, d, J = 8.2 Hz), 7.43-7.21 (11H, m), 6.95 (2H, d, J = 8.2 Hz), 6.93 (2H, d, J = 8.2 Hz), 4.58 (1H, dd, J = 8.8, 3.7 Hz), 4.45 (1H, d, J = 11.4 Hz), 4.28 (1H, d, J = 11.4 Hz), 3.90 (3H, s), 3.86 (1H, d, J = 14.0 Hz), 3.80 (1H, d, J = 14.0 Hz), 2.96 (1H, dd, J = 12.3, 8.8 Hz), 2.74 (1H, dd, J = 12.3, 3.7 Hz). |
| 130 | | (CDCl$_3$) δ: 7.98 (2H, d, J = 8.4 Hz), 7.38-7.19 (12H, m), 6.71 (1H, d, J = 3.5 Hz), 6.61 (1H, d, J = 3.5 Hz), 4.60 (1H, dd, J = 8.8, 3.7 Hz), 4.58 (1H, d, J = 12.3 Hz), 4.38 (1H, d, J = 12.3 Hz), 3.89 (3H, s), 3.82 (2H, s), 3.11-3.04 (2H, m), 2.99-2.90 (2H, m), 2.93 (1H, dd, J = 12.5, 8.8 Hz), 2.72 (1H, dd, J = 12.5, 3.7 Hz). |

TABLE 20

| Reference Example | Structural formula | ¹H-NMR |
|---|---|---|
| 131 | 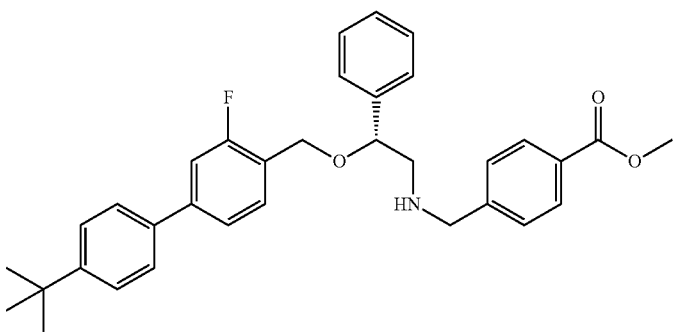 [SMILES: COC(=O)c1ccc(CNC[C@H](OCc2ccc(-c3ccc(C(C)(C)C)cc3)cc2F)c2ccccc2)cc1] | (CDCl$_3$) δ: 8.07-7.94 (2H, m), 7.57-7.18 (14H, m), 4.62 (1H, dd, J = 8.9, 3.4 Hz), 4.55 (1H, d, J = 12.0 Hz), 4.43 (1H, d, J = 12.0 Hz), 3.92 (3H, s), 3.90-3.78 (2H, m), 2.96 (1H, dd, J = 12.5, 8.9 Hz), 2.75 (1H, dd, J = 12.5, 3.4 Hz), 1.36 (9H, s). |
| 132 | 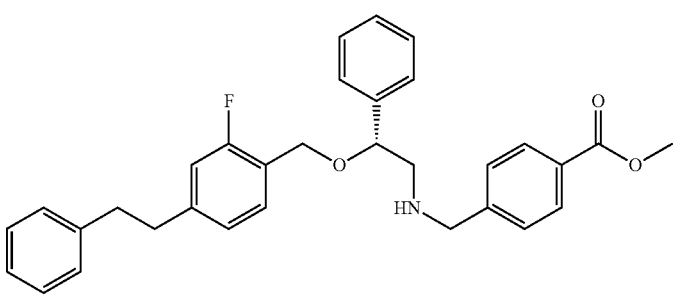 [SMILES: COC(=O)c1ccc(CNC[C@H](OCc2ccc(CCc3ccccc3)cc2F)c2ccccc2)cc1] | (CDCl$_3$) δ: 7.97 (2H, d, J = 8.2 Hz), 7.47-7.14 (11H, m), 6.93 (2H, dd, J = 7.7, 1.4 Hz), 6.86 (2H, dd, J = 11.0, 1.4 Hz), 4.58 (1H, dd, J = 9.1, 3.6 Hz), 4.49 (1H, d, J = 11.7 Hz), 4.36 (1H, d, J = 11.7 Hz), 3.90 (3H, s), 3.89-3.75 (2H, m), 2.94 (1H, dd, J = 12.2, 9.1 Hz), 2.90 (4H, s), 2.73 (1H, dd, J = 12.2, 3.6 Hz). |
| 133 | 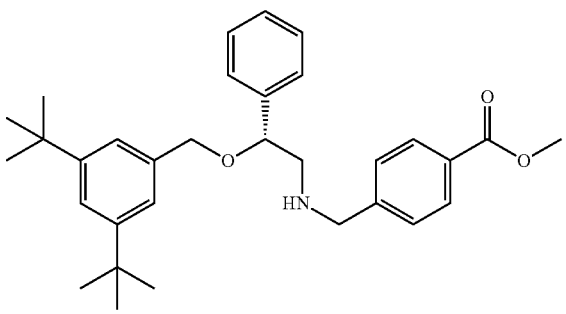 [SMILES: COC(=O)c1ccc(CNC[C@H](OCc2cc(C(C)(C)C)cc(C(C)(C)C)c2)c2ccccc2)cc1] | (CDCl$_3$) δ: 7.96 (2H, d, J = 8.2 Hz), 7.43-7.24 (8H, m), 7.13 (2H, d, J = 1.6 Hz), 4.59 (1H, dd, J = 9.2, 3.7 Hz), 4.49 (1H, d, J = 11.4 Hz), 4.29 (1H, d, J = 11.4 Hz), 3.91 (3H, s), 3.82 (2H, s), 2.96 (1H, dd, J = 12.3, 9.2 Hz), 2.74 (1H, dd, J = 12.3, 3.7 Hz), 1.30 (18H, s). |
| 134 | 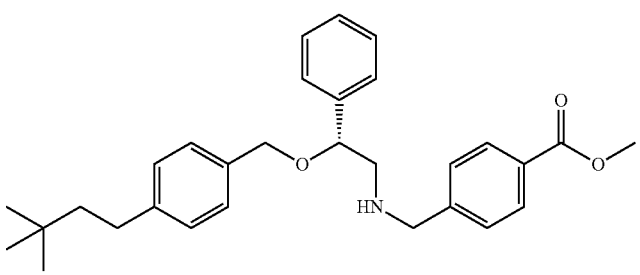 [SMILES: COC(=O)c1ccc(CNC[C@H](OCc2ccc(CCC(C)(C)C)cc2)c2ccccc2)cc1] | (CDCl$_3$) δ: 7.97 (2H, d, J = 8.2 Hz), 7.39-7.29 (7H, m), 7.21 (2H, d, J = 8.1 Hz), 7.15 (2H, d, J = 8.1 Hz), 4.57 (1H, dd, J = 9.1, 3.8 Hz), 4.46 (1H, d, J = 11.4 Hz), 4.25 (1H, d, J = 11.4 Hz), 3.90 (3H, s), 3.84 (1H, d, J = 14.1 Hz), 3.78 (1H, d, J = 14.1 Hz), 2.94 (1H, dd, J = 12.4, 9.1 Hz), 2.72 (1H, dd, J = 12.4, 3.8 Hz), 2.62-2.49 (2H, m), 1.54-1.42 (2H, m), 0.95 (9H, s). |
| 135 | 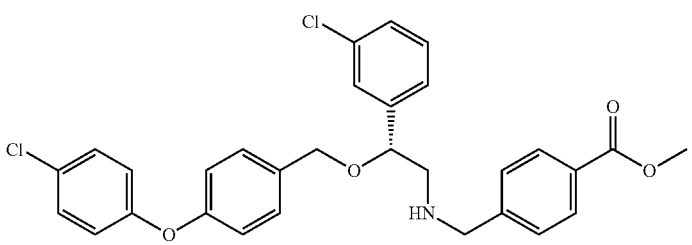 [SMILES: COC(=O)c1ccc(CNC[C@H](OCc2ccc(Oc3ccc(Cl)cc3)cc2)c2cccc(Cl)c2)cc1] | (CDCl$_3$) δ: 7.98 (2H, d, J = 6.6 Hz), 7.36-7.20 (11H, m), 6.98-6.90 (4H, m), 4.54 (1H, dd, J = 8.8, 3.8 Hz), 4.45 (1H, d, J = 11.4 Hz), 4.28 (1H, d, J = 11.4 Hz), 3.91 (3H, s), 3.85 (1H, d, J = 14.1 Hz), 3.80 (1H, d, J = 14.1 Hz), 2.93 (1H, dd, J = 12.5, 8.8 Hz), 2.72 (1H, dd, J = 12.5, 3.8 Hz). |

TABLE 21

| Reference Example | Structural formula | ¹H-NMR |
|---|---|---|
| 136 | 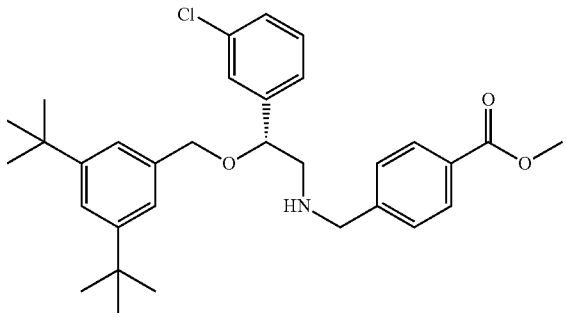 [SMILES: COC(=O)c1ccc(CNC[C@H](OCc2cc(C(C)(C)C)cc(C(C)(C)C)c2)c2cccc(Cl)c2)cc1] | (CDCl$_3$) δ: 7.97 (2H, d, J = 8.4 Hz), 7.38-7.32 (4H, m), 7.31-7.20 (3H, m), 7.12 (2H, d, J = 1.8 Hz), 4.54 (1H, dd, J = 9.0, 3.7 Hz), 4.49 (1H, d, J = 11.4 Hz), 4.31 (1H, d, J = 11.4 Hz), 3.91 (3H, s), 3.82 (2H, s), 2.92 (1H, dd, J = 12.3, 9.0 Hz), 2.72 (1H, dd, J = 12.3, 3.7 Hz), 1.30 (18H, s). |
| 137 | 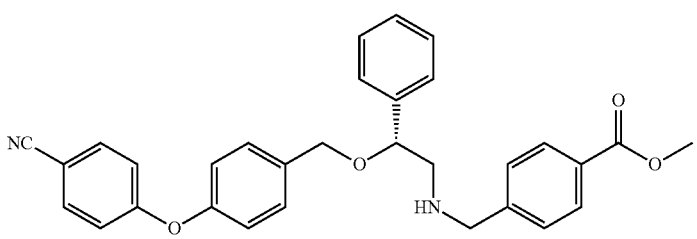 [SMILES: COC(=O)c1ccc(CNC[C@H](OCc2ccc(Oc3ccc(C#N)cc3)cc2)c2ccccc2)cc1] | (CDCl$_3$) δ: 7.98 (2H, d, J = 8.2 Hz), 7.59 (2H, d, J = 8.8 Hz), 7.44-7.28 (9H, m), 7.02 (2H, d, J = 6.4 Hz), 6.99 (2H, d, J = 6.4 Hz), 4.59 (1H, dd, J = 8.9, 3.9 Hz), 4.48 (1H, d, J = 11.5 Hz), 4.32 (1H, d, J = 11.5 Hz), 3.91 (3H, s), 3.85 (2H, d, J = 2.6 Hz), 2.99 (1H, dd, J = 12.3, 8.9 Hz), 2.76 (1H, dd, J = 12.3, 3.9 Hz). |
| 138 | 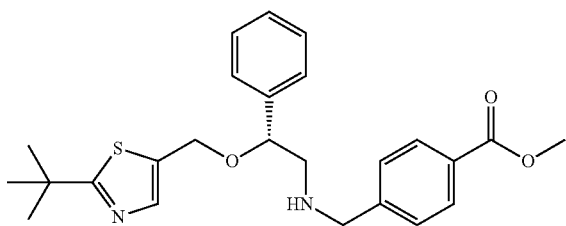 [SMILES: COC(=O)c1ccc(CNC[C@H](OCc2cnc(C(C)(C)C)s2)c2ccccc2)cc1] | (CDCl$_3$) δ: 7.98 (2H, d, J = 8.2 Hz), 7.45-7.28 (8H, m), 4.61 (1H, d, J = 12.3 Hz), 4.58 (1H, dd, J = 8.8, 3.6 Hz), 4.46 (1H, d, J = 12.3 Hz), 3.91 (3H, s), 3.83 (2H, s), 2.95 (1H, dd, J = 12.5, 8.8 Hz), 2.73 (1H, dd, J = 12.5, 3.6 Hz), 1.42 (9H, s). |
| 139 | 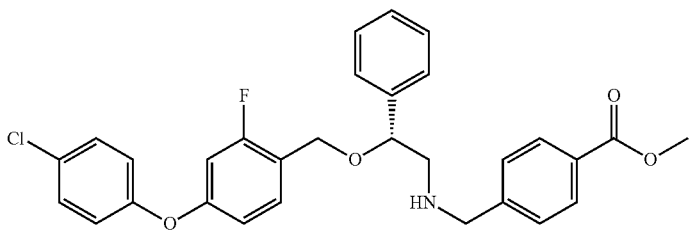 [SMILES: COC(=O)c1ccc(CNC[C@H](OCc2ccc(Oc3ccc(Cl)cc3)cc2F)c2ccccc2)cc1] | (CDCl$_3$) δ: 7.97 (2H, d, J = 8.4 Hz), 7.39-7.28 (10H, m), 6.95 (2H, d, J = 9.0 Hz), 6.73 (1H, ddd, J = 8.4, 2.2, 0.7 Hz), 6.66 (1H, dd, J = 11.0, 2.2 Hz), 4.58 (1H, dd, J = 9.0, 3.7 Hz), 4.47 (1H, d, J = 11.6 Hz), 4.36 (1H, d, J = 11.6 Hz), 3.91 (3H, s), 3.84 (2H, s), 2.94 (1H, dd, J = 12.4, 9.0 Hz), 2.74 (1H, dd, J = 12.4, 3.7 Hz). |
| 140 | 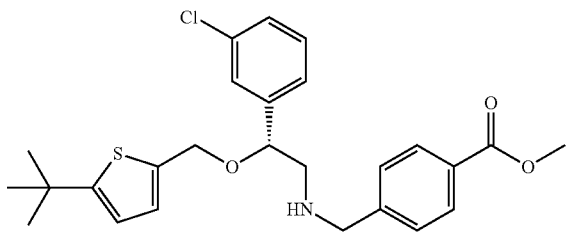 [SMILES: COC(=O)c1ccc(CNC[C@H](OCc2ccc(C(C)(C)C)s2)c2cccc(Cl)c2)cc1] | (CDCl$_3$) δ: 7.98 (2H, dt, J = 8.3, 1.8 Hz), 7.38-7.33 (3H, m), 7.30-7.20 (3H, m), 6.72 (1H, d, J = 3.5 Hz), 6.66 (1H, d, J = 3.5 Hz), 4.59 (1H, d, J = 12.3 Hz), 4.57 (1H, dd, J = 9.0, 3.6 Hz), 4.39 (1H, d, J = 12.3 Hz), 3.91 (3H, s), 3.81 (2H, s), 2.90 (1H, dd, J = 12.6, 9.0 Hz), 2.70 (1H, dd, J = 12.6, 3.6 Hz), 1.36 (9H, s). |

TABLE 22

| Reference Example | Structural formula | ¹H-NMR |
|---|---|---|
| 141 | (structure: 6-cyclopropyl-benzothiophene-CH₂-O-CH(3-chlorophenyl)-CH₂-NH-CH₂-(4-methoxycarbonylphenyl)) | (CDCl$_3$) δ: 7.96 (2H, d, J = 8.2 Hz), 7.59 (1H, d, J = 8.1 Hz), 7.50 (1H, s), 7.37-7.20 (6H, m), 7.09-7.05 (2H, m), 4.74 (1H, d, J = 12.6 Hz), 4.60 (1H, dd, J = 8.7, 3.6 Hz), 4.51 (1H, d, J = 12.6 Hz), 3.91 (3H, s), 3.80 (2H, s), 2.93 (1H, dd, J = 12.6, 8.7 Hz), 2.71 (1H, dd, J = 12.6, 3.6 Hz), 2.06-1.97 (1H, m), 1.04-0.98 (2H, m), 0.78-0.72 (2H, m). |
| 142 | (structure: 6-chloro-benzothiophene-CH₂-O-CH(3-chlorophenyl)-CH₂-NH-CH₂-(4-methoxycarbonylphenyl)) | (CDCl$_3$) δ: 7.97 (2H, d, J = 8.1 Hz), 7.78-7.78 (1H, m), 7.62 (1H, d, J = 8.4 Hz), 7.37-7.27 (6H, m), 7.25-7.20 (1H, m), 7.09 (1H, s), 4.72 (1H, d, J = 12.6 Hz), 4.59 (1H, dd, J = 8.7, 3.6 Hz), 4.53 (1H, d, J = 12.6 Hz), 3.91 (3H, s), 3.83 (2H, s), 2.94 (1H, dd, J = 12.6, 8.7 Hz), 2.73 (1H, dd, J = 12.6, 3.6 Hz). |

Reference Example 143

Methyl 4-{[N-[2-(4-tert-butylbenzyloxy-2-phenyl-ethyl]-N-(4-methoxycarbonylbutyl)amino]methyl}benzoate Reference Example 101 (240 mg) was dissolved in acetonitrile (1.0 mL), and potassium carbonate (154 mg), methyl 5-bromovalerate (0.12 mL) and sodium iodide (8 mg) were added, and the reaction solution was stirred and heated under reflux for 23 hours. The reaction solution was cooled to room temperature, and the solvent was evaporated under reduced pressure. Then, the residue was suspended in water, and the suspension was extracted with ethyl acetate. The combined organic layer was washed with water, and saturated brine, and then dried over anhydrous sodium sulfate, and the solvent was evaporated under reduced pressure. The residue was purified by silica gel column chromatography (2 to 20% ethyl acetate/hexane) to yield the title compound (276 mg) as a colorless oil.

¹H-NMR(CDCl$_3$) δ: 7.91 (2H, d, J=8.2 Hz), 7.38-7.19 (11H, m), 4.49 (1H, dd, J=7.1, 4.9 Hz), 4.41 (1H, d, J=11.5 Hz), 4.25 (1H, d, J=11.5 Hz), 3.91 (3H, s), 3.76 (1H, d, J=14.3 Hz), 3.64 (3H, s), 3.62 (1H, d, J=14.3 Hz), 2.88 (1H, dd, J=13.9, 7.1 Hz), 2.67 (1H, dd, J=13.9, 4.9 Hz), 2.53-2.42 (2H, m), 2.18 (2H, t, J=7.2 Hz), 1.57-1.33 (4H, m), 1.31 (9H, s).

The compounds of Reference Examples 144 to 190 manufactured with a similar method to that of Reference Example 143 using the corresponding Reference Example compounds are shown in Tables 23 to 34.

TABLE 23

| Reference Example | Structural formula | ¹H-NMR |
|---|---|---|
| 144 | (structure with phenethyl-phenyl-CH₂-O-CH(phenyl)-CH₂-N(CH₂-4-methoxycarbonylphenyl)(CH₂CH₂CH₂CH₂C(O)OEt)) | (CDCl$_3$) δ: 7.91 (2H, d, J = 8.2 Hz), 7.34-7.27 (9H, m), 7.20-7.14 (7H, m), 4.48 (1H, dd, J = 7.1, 5.0 Hz), 4.42 (1H, d, J = 11.7 Hz), 4.24 (1H, d, J = 11.7 Hz), 4.09 (2H, q, J = 7.1 Hz), 3.90 (3H, s), 3.76 (1H, d, J = 14.4 Hz), 3.62 (1H, d, J = 14.4 Hz), 2.91 (4H, s), 2.89 (1H, dd, J = 13.7, 7.1 Hz), 2.67 (1H, dd, J = 13.7, 5.0 Hz), 2.50-2.44 (2H, m), 2.17 (2H, t, J = 7.2 Hz), 1.49-1.42 (4H, m), 1.23 (3H, t, J = 7.1 Hz). |

TABLE 23-continued

| Reference Example | Structural formula | $^1$H-NMR |
|---|---|---|
| 145 | 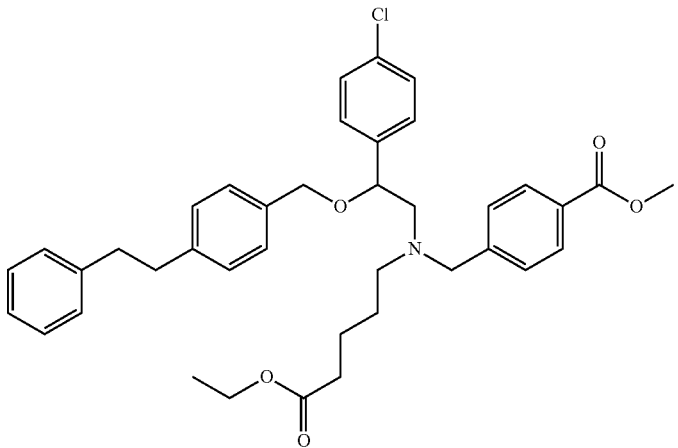 [SMILES: CCOC(=O)CCCCN(Cc1ccc(C(=O)OC)cc1)CC(OCc1ccc(CCc2ccccc2)cc1)c1ccc(Cl)cc1] | CDCl$_3$) δ: 7.91 (2H, d, J = 8.2 Hz), 7.29-7.25 (6H, m), 7.20-7.12 (9H, m), 4.43 (1H, dd, J = 7.1, 5.2 Hz), 4.39 (1H, d, J = 11.5 Hz), 4.22 (1H, d, J = 11.5 Hz), 4.10 (2H, q, J = 7.1 Hz), 3.91 (3H, s), 3.74 (1H, d, J = 14.5 Hz), 3.59 (1H, d, J = 14.5 Hz), 2.91 (4H, s), 2.84 (1H, dd, J = 13.9, 7.1 Hz), 2.63 (1H, dd, J = 13.9, 5.2 Hz), 2.50-2.44 (2H, m), 2.18 (2H, t, J = 7.2 Hz), 1.46-1.41 (4H, m), 1.23 (3H, t, J = 7.1 Hz). |
| 146 | 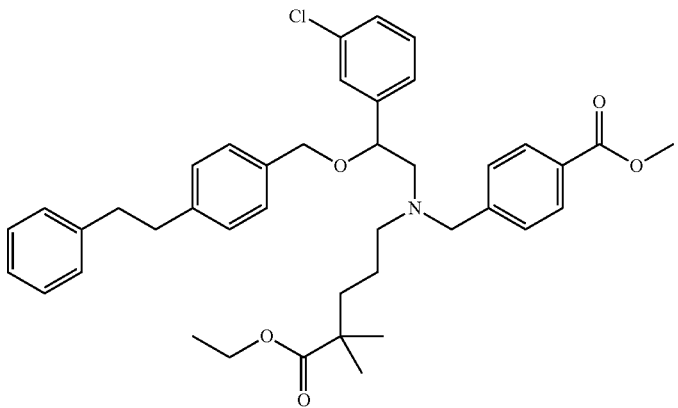 [SMILES: CCOC(=O)C(C)(C)CCCN(Cc1ccc(C(=O)OC)cc1)CC(OCc1ccc(CCc2ccccc2)cc1)c1cccc(Cl)c1] | (CDCl$_3$) δ: 7.91 (2H, d, J = 8.4 Hz), 7.32-7.26 (6H, m), 7.25-7.08 (9H, m), 4.41 (1H, dd, J = 6.7, 5.3 Hz), 4.41 (1H, d, J = 11.7 Hz), 4.23 (1H, d, J = 11.7 Hz), 4.07 (2H, q, J = 7.1 Hz), 3.91 (3H, s), 3.73 (1H, d, J = 14.5 Hz), 3.57 (1H, d, J = 14.5 Hz), 2.91 (4H, s), 2.83 (1H, dd, J = 13.7, 6.7 Hz), 2.63 (1H, dd, J = 13.7, 5.3 Hz), 2.48-2.41 (2H, m), 1.40-1.24 (4H, m), 1.19 (3H, t, J = 7.1 Hz), 1.10 (6H, s). |
| 147 | 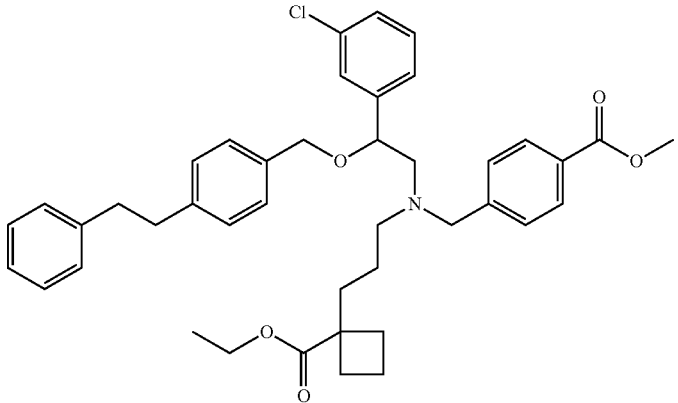 [SMILES: CCOC(=O)C1(CCCN(Cc2ccc(C(=O)OC)cc2)CC(OCc2ccc(CCc3ccccc3)cc2)c2cccc(Cl)c2)CCC1] | (CDCl$_3$) δ: 7.91 (2H, d, J = 8.2 Hz), 7.31-7.10 (15H, m), 4.42 (1H, dd, J = 7.1, 5.5 Hz), 4.42 (1H, d, J = 11.5 Hz), 4.23 (1H, d, J = 11.5 Hz), 4.10 (2H, q, J = 7.1 Hz), 3.91 (3H, s), 3.73 (1H, d, J = 14.5 Hz), 3.57 (1H, d, J = 14.5 Hz), 2.91 (4H, s), 2.83 (1H, dd, J = 13.8, 7.1 Hz), 2.62 (1H, dd, J = 13.8, 5.5 Hz), 2.50-2.35 (4H, m), 1.89-1.75 (4H, m), 1.67-1.62 (2H, m), 1.33-1.24 (2H, m), 1.20 (3H, t, J = 7.1 Hz). |

TABLE 24

| Reference Example | Structural formula | $^1$H-NMR |
|---|---|---|
| 148 | 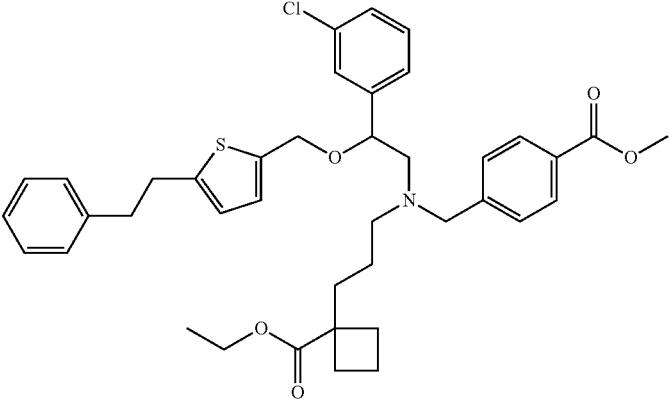 [SMILES: CCOC(=O)C1(CCCN(Cc2ccc(C(=O)OC)cc2)CC(OCc2ccc(CCc3ccccc3)s2)c2cccc(Cl)c2)CCC1] | (CDCl$_3$) δ: 7.92 (2H, d, J = 8.1 Hz), 7.32-7.16 (10H, m), 7.14-7.08 (1H, m), 6.68 (1H, d, J = 3.3 Hz), 6.60 (1H, d, J = 3.3 Hz), 4.52 (1H, d, J = 12.5 Hz), 4.46 (1H, dd, J = 7.0, 5.3 Hz), 4.33 (1H, d, J = 12.5 Hz), 4.10 (2H, q, J = 7.1 Hz), 3.90 (3H, s), 3.73 (1H, d, J = 14.1 Hz), 3.57 (1H, d, J = 14.1 Hz), 3.12-3.06 (2H, m), 2.97-2.90 (2H, m), 2.81 (1H, dd, J = 13.7, 7.0 Hz), 2.61 (1H, dd, J = 13.7, 5.3 Hz), 2.49-2.34 (4H, m), 1.87-1.80 (4H, m), 1.68-1.62 (2H, m), 1.32-1.24 (2H, m), 1.20 (3H, t, J = 7.1 Hz). |
| 149 | 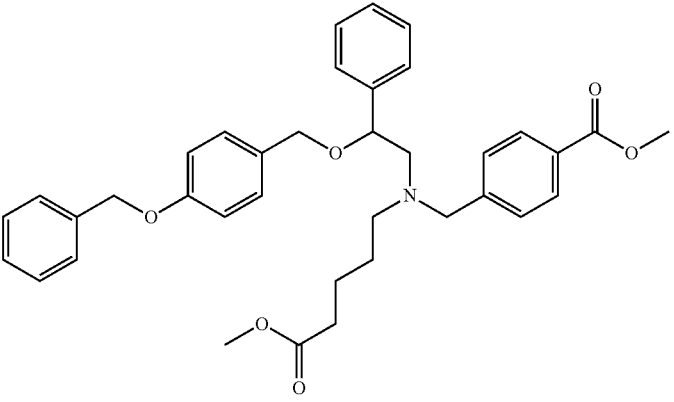 [SMILES: COC(=O)CCCCN(Cc1ccc(C(=O)OC)cc1)CC(OCc1ccc(OCc2ccccc2)cc1)c1ccccc1] | (CDCl$_3$) δ: 7.91 (2H, d, J = 8.4 Hz), 7.46-7.23 (12H, m), 7.20 (2H, d, J = 8.8 Hz), 6.92 (2H, d, J = 8.8 Hz), 5.06 (2H, s), 4.46 (1H, dd, J = 7.1, 5.1 Hz), 4.38 (1H, d, J = 11.4 Hz), 4.19 (1H, d, J = 11.4 Hz), 3.90 (3H, s), 3.75 (1H, d, J = 14.1 Hz), 3.63 (3H, s), 3.60 (1H, d, J = 14.1 Hz), 2.86 (1H, dd, J = 13.7, 7.1 Hz), 2.65 (1H, dd, J = 13.7, 5.1 Hz), 2.49-2.43 (2H, m), 2.17 (2H, t, J = 7.2 Hz), 1.57-1.33 (4H, m). |
| 150 | 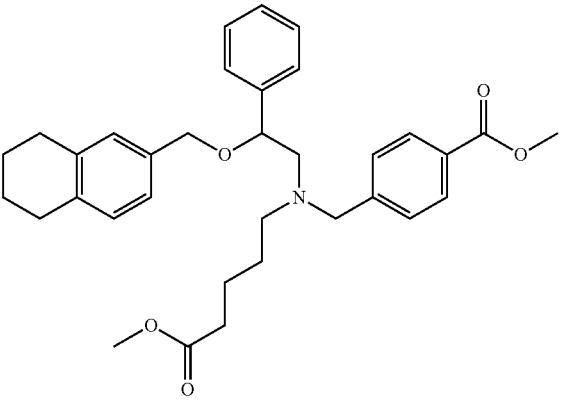 [SMILES: COC(=O)CCCCN(Cc1ccc(C(=O)OC)cc1)CC(OCc1ccc2c(c1)CCCC2)c1ccccc1] | (CDCl$_3$) δ: 7.91 (2H, d, J = 8.2 Hz), 7.37-7.24 (7H, m), 7.01-6.96 (3H, m), 4.49 (1H, dd, J = 7.1, 5.0 Hz), 4.37 (1H, d, J = 11.4 Hz), 4.20 (1H, d, J = 11.4 Hz), 3.91 (3H, s), 3.78 (1H, d, J = 14.5 Hz), 3.64 (3H, s), 3.61 (1H, d, J = 14.5 Hz), 2.88 (1H, dd, J = 13.9, 7.1 Hz), 2.79-2.69 (4H, m), 2.67 (1H, dd, J = 13.9, 5.0 Hz), 2.53-2.41 (2H, m), 2.18 (2H, t, J = 7.2 Hz), 1.82-1.74 (4H, m), 1.58-1.33 (4H, m). |

TABLE 24-continued

| Reference Example | Structural formula | ¹H-NMR |
|---|---|---|
| 151 | 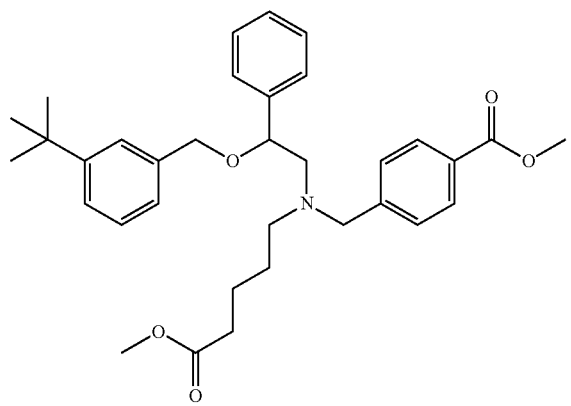 [SMILES: COC(=O)CCCCN(Cc1ccc(C(=O)OC)cc1)CC(OCc1cccc(C(C)(C)C)c1)c1ccccc1] | (CDCl₃) δ: 7.93-7.86 (2H, m), 7.38-7.19 (10H, m), 7.14-7.08 (1H, m), 4.49 (1H, dd, J = 7.4, 4.9 Hz), 4.45 (1H, d, J = 11.7 Hz), 4.27 (1H, d, J = 11.7 Hz), 3.90 (3H, s), 3.77 (1H, d, J = 14.3 Hz), 3.63 (1H, d, J = 14.3 Hz), 3.63 (3H, s), 2.89 (1H, dd, J = 13.8, 7.4 Hz), 2.68 (1H, dd, J = 13.8, 4.9 Hz), 2.54-2.42 (2H, m), 2.17 (2H, t, J = 7.3 Hz), 1.54-1.34 (4H, m), 1.29 (9H, s). |

TABLE 25

| Reference Example | Structural formula | ¹H-NMR |
|---|---|---|
| 152 | 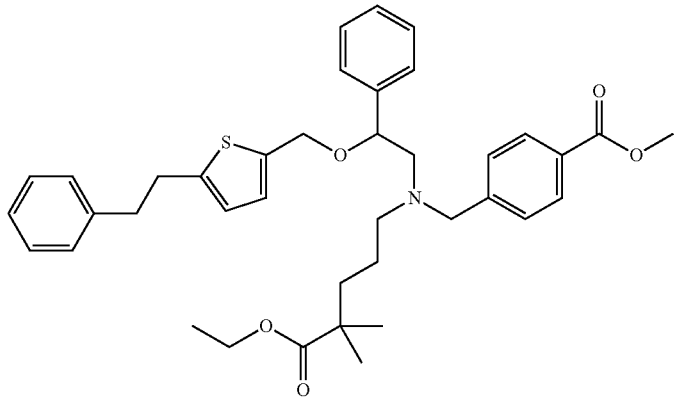 [SMILES: CCOC(=O)C(C)(C)CCCN(Cc1ccc(C(=O)OC)cc1)CC(OCc1ccc(CCc2ccccc2)s1)c1ccccc1] | (CDCl₃) δ: 7.91 (2H, d, J = 8.2 Hz), 7.35-7.27 (9H, m), 7.24-7.13 (3H, m), 6.68 (1H, d, J = 3.5 Hz), 6.60 (1H, d, J = 3.5 Hz), 4.52 (1H, dd, J = 7.3, 5.1 Hz), 4.52 (1H, d, J = 12.3 Hz), 4.33 (1H, d, J = 12.3 Hz), 4.06 (2H, q, J = 7.1 Hz), 3.90 (3H, s), 3.76 (1H, d, J = 14.5 Hz), 3.61 (1H, d, J = 14.5 Hz), 3.12-3.05 (2H, m), 2.98-2.91 (2H, m), 2.85 (1H, dd, J = 13.9, 7.3 Hz), 2.65 (1H, dd, J = 13.9, 5.1 Hz), 2.47-2.41 (2H, m), 1.40-1.23 (4H, m), 1.18 (3H, t, J = 7.1 Hz), 1.10 (6H, s). |
| 153 | 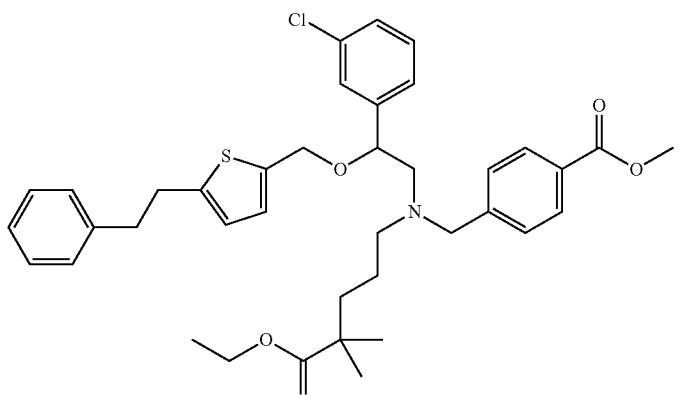 | (CDCl₃) δ: 7.91 (2H, d, J = 8.1 Hz), 7.31-7.10 (11H, m), 6.68 (1H, d, J = 3.1 Hz), 6.60 (1H, d, J = 3.1 Hz), 4.52 (1H, d, J = 12.3 Hz), 4.46 (1H, dd, J = 7.0, 5.5 Hz), 4.33 (1H, d, J = 12.3 Hz), 4.07 (2H, q, J = 7.1 Hz), 3.90 (3H, s), 3.73 (1H, d, J = 14.5 Hz), 3.57 (1H, d, J = 14.5 Hz), 3.12-3.06 (2H, m), 2.99-2.92 (2H, m), 2.81 (1H, dd, J = 13.7, 7.0 Hz), 2.62 (1H, dd, J = 13.7, 5.5 Hz), 2.47-2.41 (2H, m), 1.41-1.30 (4H, m), 1.19 (3H, t, J = 7.1 Hz), 1.11 (6H, s). |

TABLE 25-continued

| Reference Example | Structural formula | ¹H-NMR |
|---|---|---|
| 154 | | (CDCl₃) δ: 7.92 (2H, d, J = 8.2 Hz), 7.37-7.28 (9H, m), 7.24-7.15 (3H, m), 6.68 (1H, d, J = 3.5 Hz), 6.60 (1H, d, J = 3.5 Hz), 4.52 (1H, dd, J = 7.2, 4.9 Hz), 4.52 (1H, d, J = 12.3 Hz), 4.33 (1H, d, J = 12.3 Hz), 4.09 (2H, q, J = 7.1 Hz), 3.90 (3H, s), 3.76 (1H, d, J = 14.5 Hz), 3.61 (1H, d, J = 14.5 Hz), 3.12-3.05 (2H, m), 2.99-2.93 (2H, m), 2.85 (1H, dd, J = 13.9, 7.2 Hz), 2.64 (1H, dd, J = 13.9, 4.9 Hz), 2.52-2.32 (4H, m), 1.86-1.75 (4H, m), 1.68-1.61 (2H, m), 1.33-1.24 (2H, m), 1.19 (3H, t, J = 7.1 Hz). |
| 155 | | (CDCl₃) δ 7.90 (2H, dd, J = 6.6, 1.8 Hz), 7.37-7.26 (9H, m), 7.20-7.14 (7H, m), 4.48 (1H, dd, J = 5.6, 4.9 Hz), 4.42 (1H, d, J = 11.7 Hz), 4.24 (1H, d, J = 11.7 Hz), 4.10 (2H, q, J = 7.1 Hz), 3.90 (3H, s), 3.76 (1H, d, J = 14.4 Hz), 3.61 (1H, d, J = 14.4 Hz), 2.91 (4H, s), 2.89 (1H, dd, J = 13.7, 5.6 Hz), 2.67 (1H, dd, J = 13.7, 4.9 Hz), 2.47-2.43 (2H, m), 2.20 (2H, t, J = 7.5 Hz), 1.48-1.34 (4H, m), 1.23 (3H, t, J = 7.1 Hz), 1.19-1.13 (2H, m). |

TABLE 26

| Reference Example | Structural formula | ¹H-NMR |
|---|---|---|
| 156 | | (CDCl₃) δ: 7.91 (2H, d, J = 8.2 Hz), 7.37-7.11 (16H, m), 4.48 (1H, dd, J = 6.8, 5.1 Hz), 4.42 (1H, d, J = 11.5 Hz), 4.23 (1H, d, J = 11.5 Hz), 4.06 (2H, q, J = 7.1 Hz), 3.91 (3H, s), 3.76 (1H, d, J = 14.5 Hz), 3.61 (1H, d, J = 14.5 Hz), 2.87 (4H, s), 2.87 (1H, dd, J = 13.7, 6.8 Hz), 2.66 (1H, dd, J = 13.7, 5.1 Hz), 2.49-2.41 (2H, m), 1.40-1.23 (4H, m), 1.18 (3H, t, J = 7.1 Hz), 1.09 (6H, s). |

TABLE 26-continued

| Reference Example | Structural formula | ¹H-NMR |
|---|---|---|
| 157 | 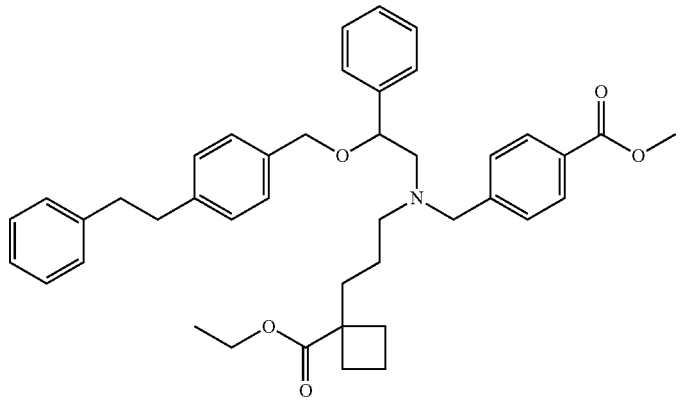 [SMILES: CCOC(=O)C1(CCCN(Cc2ccc(C(=O)OC)cc2)CC(OCc2ccc(CCc3ccccc3)cc2)c2ccccc2)CCC1] | (CDCl₃) δ: 7.91 (2H, d, J = 8.1 Hz), 7.36-7.13 (16H, m), 4.49 (1H, dd, J = 7.2, 4.9 Hz), 4.42 (1H, d, J = 11.7 Hz), 4.24 (1H, d, J = 11.7 Hz), 4.09 (2H, q, J = 7.1 Hz), 3.91 (3H, s), 3.76 (1H, d, J = 14.1 Hz), 3.61 (1H, d, J = 14.1 Hz), 2.87 (4H, s), 2.87 (1H, dd, J = 13.9, 7.2 Hz), 2.65 (1H, dd, J = 13.9, 4.9 Hz), 2.51-2.42 (2H, m), 2.40-2.32 (2H, m), 1.85-1.75 (4H, m), 1.64 (2H, dd, J = 11.1, 4.9 Hz), 1.31-1.26 (2H, m), 1.19 (3H, t, J = 7.1 Hz). |
| 158 | 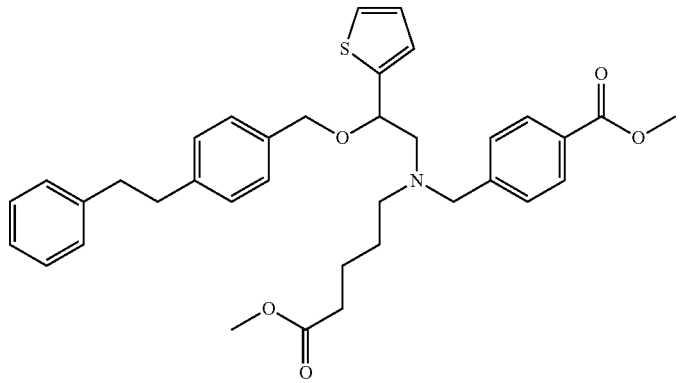 [SMILES: COC(=O)CCCCN(Cc1ccc(C(=O)OC)cc1)CC(OCc1ccc(CCc2ccccc2)cc1)c1cccs1] | (CDCl₃) δ: 7.92 (2H, d, J = 8.2 Hz), 7.32-7.11 (12H, m), 6.98 (1H, dd, J = 4.9, 3.5 Hz), 6.94 (1H, dd, J = 3.5, 1.1 Hz), 4.71 (1H, dd, J = 7.0, 5.5 Hz), 4.51 (1H, d, J = 11.5 Hz), 4.29 (1H, d, J = 11.5 Hz), 3.90 (3H, s), 3.76 (1H, d, J = 14.0 Hz), 3.63 (3H, s), 3.62 (1H, d, J = 14.0 Hz), 2.96 (1H, dd, J = 14.0, 7.0 Hz), 2.91 (4H, s), 2.78 (1H, dd, J = 14.0, 5.5 Hz), 2.51-2.42 (2H, m), 2.18 (2H, t, J = 7.0 Hz), 1.58-1.35 (4H, m). |
| 159 | 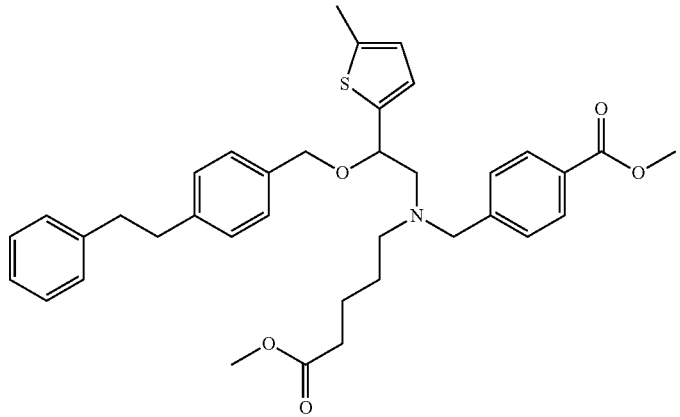 [SMILES: COC(=O)CCCCN(Cc1ccc(C(=O)OC)cc1)CC(OCc1ccc(CCc2ccccc2)cc1)c1ccc(C)s1] | (CDCl₃) δ: 7.92 (2H, d, J = 8.4 Hz), 7.32-7.11 (11H, m), 6.72 (1H, d, J = 3.3 Hz), 6.61 (1H, dd, J = 3.3, 1.1 Hz), 4.61 (1H, dd, J = 6.7, 5.5 Hz), 4.52 (1H, d, J = 11.5 Hz), 4.28 (1H, d, J = 11.5 Hz), 3.90 (3H, s), 3.75 (1H, d, J = 14.5 Hz), 3.63 (3H, s), 3.61 (1H, d, J = 14.5 Hz), 2.94 (1H, dd, J = 13.0, 6.7 Hz), 2.90 (4H, s), 2.75 (1H, dd, J = 13.0, 5.5 Hz), 2.50-2.44 (5H, m), 2.19 (2H, t, J = 7.3 Hz), 1.58-1.36 (4H, m). |

TABLE 27

| Reference Example | Structural formula | ¹H-NMR |
|---|---|---|
| 160 | | (CDCl$_3$) δ: 7.90 (2H, d, J = 8.3 Hz), 7.37-7.08 (16H, m), 4.48 (1H, dd, J = 7.0, 5.1 Hz), 4.43 (1H, d, J = 11.6 Hz), 4.25 (1H, d, J = 11.6 Hz), 3.90 (3H, s), 3.78 (1H, d, J = 14.4 Hz), 3.63 (3H, s), 3.62 (1H, d, J = 14.4 Hz), 2.89 (1H, dd, J = 13.8, 7.0 Hz), 2.88 (4H, s), 2.68 (1H, dd, J = 13.8, 5.1 Hz), 2.52-2.43 (2H, m), 2.17 (2H, t, J = 7.3 Hz), 1.54-1.40 (4H, m). |
| 161 | | (CDCl$_3$) δ: 7.94-7.87 (2H, m), 7.39-7.09 (16H, m), 4.48 (1H, dd, J = 7.1, 5.0 Hz), 4.42 (1H, d, J = 11.7 Hz), 4.24 (1H, d, J = 11.7 Hz), 3.90 (3H, s), 3.76 (1H, d, J = 14.3 Hz), 3.63 (3H, s), 3.62 (1H, d, J = 14.3 Hz), 2.91 (4H, s), 2.88 (1H, dd, J = 13.8, 7.1 Hz), 2.67 (1H, dd, J = 13.8, 5.0 Hz), 2.52-2.40 (2H, m), 2.18 (2H, t, J = 7.2 Hz), 1.58-1.33 (4H, m). |
| 162 | | (CDCl$_3$) δ: 7.95-7.86 (2H, m), 7.39-7.09 (16H, m), 4.48 (1H, dd, J = 7.1, 4.9 Hz), 4.42 (1H, d, J = 11.7 Hz), 4.24 (1H, d, J = 11.7 Hz), 3.90 (3H, s), 3.76 (1H, d, J = 14.5 Hz), 3.63 (3H, s), 3.62 (1H, d, J = 14.5 Hz), 2.91 (4H, s), 2.88 (1H, dd, J = 13.9, 7.1 Hz), 2.67 (1H, dd, J = 13.9, 4.9 Hz), 2.51-2.43 (2H, m), 2.18 (2H, t, J = 7.2 Hz), 1.56-1.34 (4H, m). |

TABLE 27-continued

| Reference Example | Structural formula | ¹H-NMR |
|---|---|---|
| 163 | | (CDCl₃) δ: 7.90 (2H, d, J = 8.2 Hz), 7.31-7.23 (4H, m), 7.21-7.15 (6H, m), 7.12-6.96 (6H, m), 4.10 (2H, q, J = 7.1 Hz), 3.90 (3H, s), 3.51 (2H, s), 2.88 (4H, s), 2.74 (1H, s), 2.59-2.54 (2H, m), 2.45-2.31 (4H, m), 2.17-2.11 (3H, m), 1.80-1.74 (1H, m), 1.47-1.35 (4H, m), 1.23 (3H, t, J = 7.1 Hz). |
| 164 | | (CDCl₃) δ: 7.91 (2H, dd, J = 8.2, 1.6 Hz), 7.31-7.11 (15H, m), 4.42 (1H, dd, J = 6.9, 5.4 Hz), 4.42 (1H, d, J = 11.5 Hz), 4.24 (1H, d, J = 11.5 Hz), 4.24 (2H, q, J = 7.1 Hz), 3.91 (3H, s), 3.74 (1H, d, J = 14.3 Hz), 3.59 (1H, d, J = 14.3 Hz), 2.91 (4H, s), 2.85 (1H, dd, J = 13.8, 6.9 Hz), 2.64 (1H, dd, J = 13.8, 5.4 Hz), 2.46 (2H, t, J = 6.2 Hz), 2.18 (2H, t, J = 7.1 Hz), 1.52-1.38 (4H, m), 1.23 (3H, t, J = 7.1 Hz). |

TABLE 28

| Reference Example | Structural formula | ¹H-NMR |
|---|---|---|
| 165 | 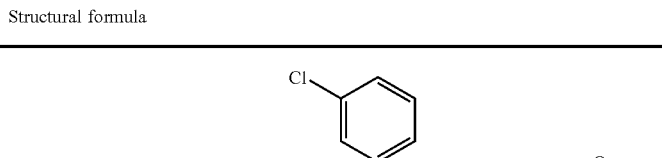 | (CDCl₃) δ: 7.91 (2H, d, J = 8.1 Hz), 7.31-7.18 (10H, m), 7.14-7.11 (1H, m), 6.68 (1H, d, J = 3.3 Hz), 6.60 (1H, d, J = 3.3 Hz), 4.53 (1H, d, J = 12.3 Hz), 4.47 (1H, dd, J = 6.9, 5.4 Hz), 4.34 (1H, d, J = 12.3 Hz), 4.10 (2H, q, J = 7.1 Hz), 3.90 (3H, s), 3.74 (1H, d, J = 14.3 Hz), 3.59 (1H, d, J = 14.3 Hz), 3.12-3.06 (2H, m), 2.99-2.92 (2H, m), 2.82 (1H, dd, J = 13.8, 6.9 Hz), 2.63 (1H, dd, J = 13.8, 5.4 Hz), 2.49-2.42 (2H, m), 2.18 (2H, t, J = 7.2 Hz), 1.55-1.39 (4H, m), 1.23 (3H, t, J = 7.1 Hz). |

TABLE 28-continued

| Reference Example | Structural formula | ¹H-NMR |
|---|---|---|
| 166 | | (CDCl₃) δ: 7.91 (2H, d, J = 8.2 Hz), 7.37-7.26 (9H, m), 7.22-7.17 (3H, m), 6.68 (1H, d, J = 3.3 Hz), 6.60 (1H, d, J = 3.3 Hz), 4.53 (1H, dd, J = 7.4, 4.9 Hz), 4.53 (1H, d, J = 12.3 Hz), 4.34 (1H, d, J = 12.3 Hz), 4.09 (2H, q, J = 7.1 Hz), 3.89 (3H, s), 3.77 (1H, d, J = 14.2 Hz), 3.62 (1H, d, J = 14.2 Hz), 3.13-3.05 (2H, m), 2.98-2.92 (2H, m), 2.86 (1H, dd, J = 13.9, 7.4 Hz), 2.66 (1H, dd, J = 13.9, 4.9 Hz), 2.52-2.42 (2H, m), 2.17 (2H, t, J = 7.3 Hz), 1.52-1.40 (4H, m), 1.22 (3H, t, J = 7.1 Hz). |
| 167 | | (CDCl₃) δ 7.92 (2H, d, J = 8.2 Hz), 7.33-7.09 (13H, m), 7.00 (1H, dd, J = 5.0, 1.0 Hz), 4.58 (1H, dd, J = 8.0, 5.5 Hz), 4.45 (1H, d, J = 11.5 Hz), 4.26 (1H, d, J = 11.5 Hz), 3.91 (3H, s), 3.74 (1H, d, J = 14.3 Hz), 3.64 (3H, s), 3.60 (1H, d, J = 14.3 Hz), 2.91 (4H, s), 2.90 (1H, dd, J = 13.7, 8.0 Hz), 2.71 (1H, dd, J = 13.7, 5.5 Hz), 2.53-2.38 (2H, m), 2.19 (2H, t, J = 7.2 Hz), 1.60-1.34 (4H, m). |
| 168 | | (CDCl₃) δ 7.93 (2H, d, J = 8.2 Hz), 7.32-7.11 (11H, m), 6.77 (1H, d, J = 3.7 Hz), 6.69 (1H, d, J = 3.7 Hz), 4.54 (1H, dd, J = 7.0, 5.7 Hz), 4.53 (1H, d, J = 11.4 Hz), 4.29 (1H, d, J = 11.4 Hz), 3.91 (3H, s), 3.73 (1H, d, J = 14.3 Hz), 3.64 (3H, s), 3.62 (1H, d, J = 14.3 Hz), 2.91 (4H, s), 2.89 (1H, dd, J = 13.7, 7.0 Hz), 2.74 (1H, dd, J = 13.7, 5.7 Hz), 2.46 (2H, t, J = 6.9 Hz), 2.20 (2H, t, J = 7.2 Hz), 1.60-1.33 (4H, m). |

TABLE 29

| Reference Example | Structural formula | ¹H-NMR |
|---|---|---|
| 169 | 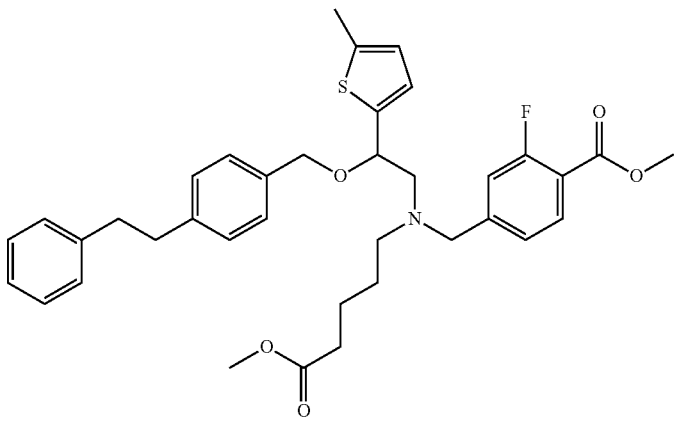 [SMILES: COC(=O)CCCCN(Cc1ccc(C(=O)OC)c(F)c1)CC(OCc1ccc(CCc2ccccc2)cc1)c1ccc(C)s1] | (CDCl$_3$) δ: 7.85-7.76 (1H, m), 7.31-7.10 (9H, m), 7.07-6.99 (2H, m), 6.73 (1H, d, J = 3.3 Hz), 6.61 (1H, dd, J = 3.3, 1.1 Hz), 4.61 (1H, dd, J = 6.6, 5.7 Hz), 4.52 (1H, d, J = 11.5 Hz), 4.27 (1H, d, J = 11.5 Hz), 3.92 (3H, s), 3.73 (1H, d, J = 14.8 Hz), 3.64 (3H, s), 3.59 (1H, d, J = 14.8 Hz), 2.93 (1H, dd, J = 13.7, 6.6 Hz), 2.90 (4H, s), 2.75 (1H, dd, J = 13.7, 5.7 Hz), 2.51-2.40 (5H, m), 2.21 (2H, t, J = 7.3 Hz), 1.59-1.35 (4H, m). |
| 170 | 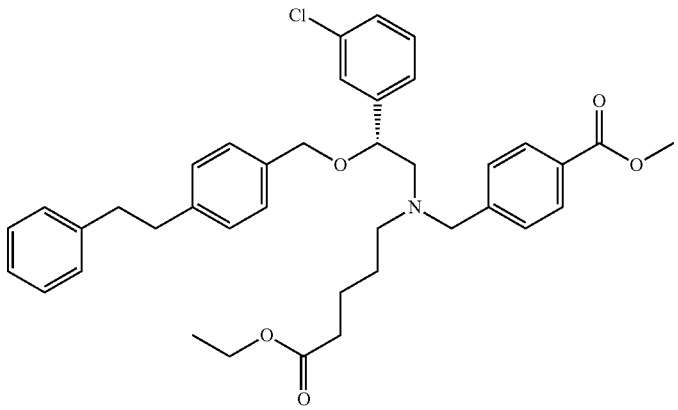 [SMILES: CCOC(=O)CCCCN(Cc1ccc(C(=O)OC)cc1)C[C@H](OCc1ccc(CCc2ccccc2)cc1)c1cccc(Cl)c1] | (CDCl$_3$) δ: 7.91 (2H, d, J = 8.4 Hz), 7.31-7.23 (7H, m), 7.21-7.12 (8H, m), 4.42 (1H, dd, J = 6.9, 5.4 Hz), 4.42 (1H, d, J = 11.5 Hz), 4.24 (1H, d, J = 11.5 Hz), 4.10 (2H, q, J = 7.3 Hz), 3.91 (3H, s), 3.74 (1H, d, J = 14.3 Hz), 3.59 (1H, d, J = 14.3 Hz), 2.91 (4H, s), 2.85 (1H, dd, J = 13.8, 6.9 Hz), 2.64 (1H, dd, J = 13.8, 5.4 Hz), 2.49-2.41 (2H, m), 2.18 (2H, t, J = 7.2 Hz), 1.51-1.38 (4H, m), 1.23 (3H, t, J = 7.3 Hz). |
| 171 | 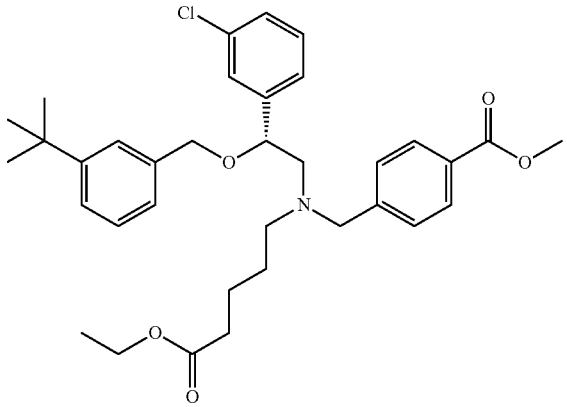 [SMILES: CCOC(=O)CCCCN(Cc1ccc(C(=O)OC)cc1)C[C@H](OCc1cccc(C(C)(C)C)c1)c1cccc(Cl)c1] | (CDCl$_3$) δ: 7.90 (2H, d, J = 8.4 Hz), 7.33-7.21 (8H, m), 7.16-7.09 (2H, m), 4.45 (1H, d, J = 11.5 Hz), 4.43 (1H, dd, J = 6.9, 5.3 Hz), 4.27 (1H, d, J = 11.5 Hz), 4.10 (2H, q, J = 7.1 Hz), 3.91 (3H, s), 3.75 (1H, d, J = 14.3 Hz), 3.60 (1H, d, J = 14.3 Hz), 2.86 (1H, dd, J = 14.0, 6.9 Hz), 2.66 (1H, dd, J = 14.0, 5.3 Hz), 2.50-2.43 (2H, m), 2.17 (2H, t, J = 7.2 Hz), 1.53-1.30 (4H, m), 1.29 (9H, s), 1.23 (3H, t, J = 7.1 Hz). |

TABLE 29-continued

| Reference Example | Structural formula | ¹H-NMR |
|---|---|---|
| 172 | 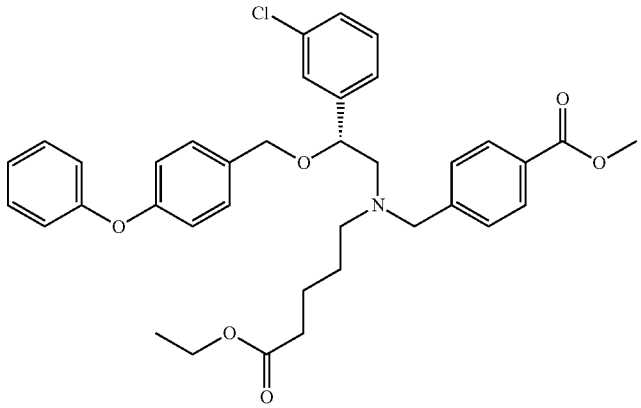 [SMILES: CCOC(=O)CCCCN(Cc1ccc(C(=O)OC)cc1)C[C@H](OCc1ccc(Oc2ccccc2)cc1)c1cccc(Cl)c1] | (CDCl₃) δ: 7.91 (2H, d, J = 8.2 Hz), 7.36-7.21 (9H, m), 7.15-7.07 (2H, m), 7.02-6.94 (4H, m), 4.43 (1H, dd, J = 7.0, 5.3 Hz), 4.41 (1H, d, J = 11.4 Hz), 4.24 (1H, d, J = 11.4 Hz), 4.10 (2H, q, J = 7.1 Hz), 3.91 (3H, s), 3.74 (1H, d, J = 14.3 Hz), 3.59 (1H, d, J = 14.3 Hz), 2.85 (1H, dd, J = 13.7, 7.0 Hz), 2.64 (1H, dd, J = 13.7, 5.3 Hz), 2.47 (2H, td, J = 6.9, 3.3 Hz), 2.19 (2H, t, J = 7.1 Hz), 1.55-1.39 (4H, m), 1.23 (3H, t, J = 7.1 Hz). |

TABLE 30

| Reference Example | Structural formula | ¹H-NMR |
|---|---|---|
| 173 | 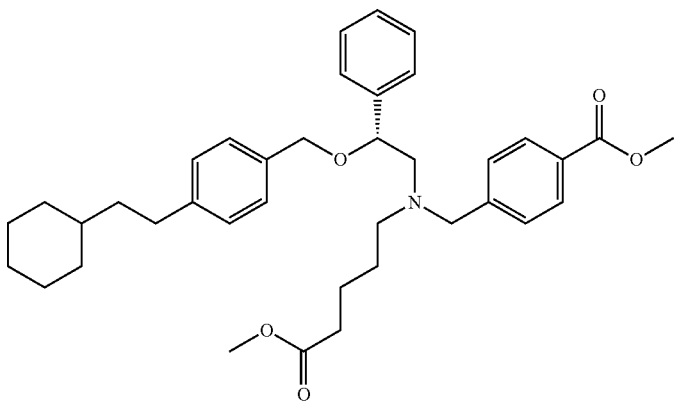 [SMILES: COC(=O)CCCCN(Cc1ccc(C(=O)OC)cc1)C[C@H](OCc1ccc(CCC2CCCCC2)cc1)c1ccccc1] | (CDCl₃) δ: 7.91 (2H, d, J = 8.4 Hz), 7.39-7.22 (7H, m), 7.19 (2H, d, J = 8.2 Hz), 7.12 (2H, d, J = 8.2 Hz), 4.48 (1H, dd, J = 7.0, 5.1 Hz), 4.41 (1H, d, J = 11.5 Hz), 4.23 (1H, d, J = 11.5 Hz), 3.91 (3H, s), 3.76 (1H, d, J = 14.3 Hz), 3.63 (3H, s), 3.61 (1H, d, J = 14.3 Hz), 2.88 (1H, dd, J = 13.8, 7.0 Hz), 2.66 (1H, dd, J = 13.8, 5.1 Hz), 2.64-2.53 (2H, m), 2.51-2.40 (2H, m), 2.17 (2H, t, J = 7.2 Hz), 1.81-1.59 (5H, m), 1.58-1.34 (5H, m), 1.31-1.09 (5H, m), 1.02-0.81 (2H, m). |
| 174 | 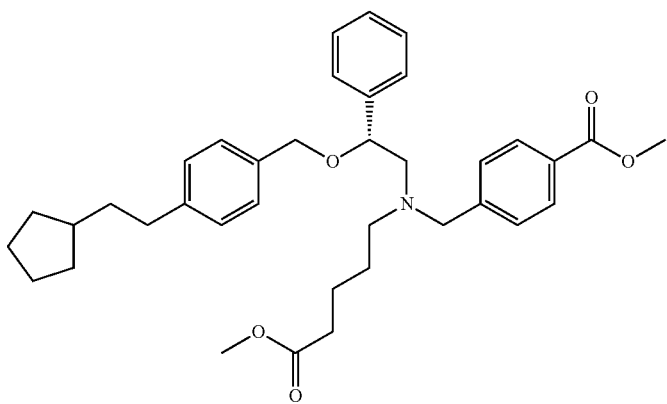 [SMILES: COC(=O)CCCCN(Cc1ccc(C(=O)OC)cc1)C[C@H](OCc1ccc(CCC2CCCC2)cc1)c1ccccc1] | (CDCl₃) δ: 7.91 (2H, d, J = 8.2 Hz), 7.38-7.22 (7H, m), 7.19 (2H, d, J = 8.1 Hz), 7.13 (2H, d, J = 8.1 Hz), 4.48 (1H, dd, J = 6.9, 4.9 Hz), 4.41 (1H, d, J = 11.5 Hz), 4.23 (1H, d, J = 11.5 Hz), 3.91 (3H, s), 3.76 (1H, d, J = 14.5 Hz), 3.64 (3H, s), 3.61 (1H, d, J = 14.5 Hz), 2.88 (1H, dd, J = 14.0, 6.9 Hz), 2.66 (1H, dd, J = 14.0, 4.9 Hz), 2.64-2.55 (2H, m), 2.54-2.39 (2H, m), 2.17 (2H, t, J = 7.2 Hz), 1.87-1.68 (3H, m), 1.68-1.32 (10H, m), 1.21-1.01 (2H, m). |

TABLE 30-continued

| Reference Example | Structural formula | ¹H-NMR |
|---|---|---|
| 175 | 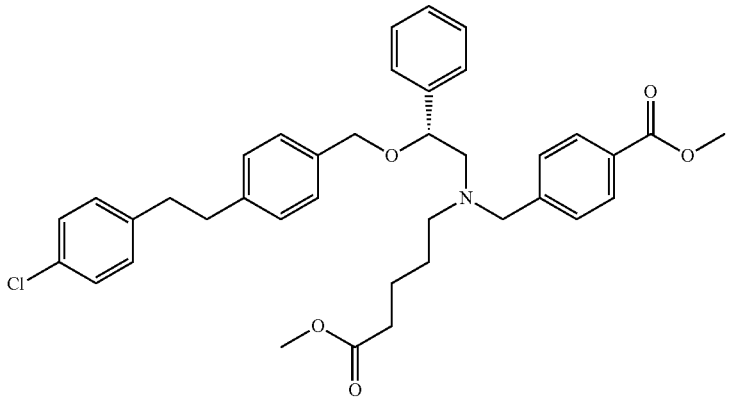 [SMILES: COC(=O)CCCCN(Cc1ccc(C(=O)OC)cc1)C[C@H](OCc1ccc(CCc2ccc(Cl)cc2)cc1)c1ccccc1] | (CDCl₃) δ: 7.91 (2H, d, J = 8.2 Hz), 7.38-7.23 (8H, m), 7.23-7.11 (7H, m), 4.48 (1H, dd, J = 7.0, 5.5 Hz), 4.42 (1H, d, J = 11.7 Hz), 4.24 (1H, d, J = 11.7 Hz), 3.90 (3H, s), 3.76 (1H, d, J = 14.3 Hz), 3.63 (3H, s), 3.61 (1H, d, J = 14.3 Hz), 2.91 (4H, s), 2.88 (1H, dd, J = 13.9, 7.0 Hz), 2.67 (1H, dd, J = 13.9, 5.5 Hz), 2.52-2.42 (2H, m), 2.18 (2H, t, J = 7.2 Hz), 1.60-1.33 (4H, m). |
| 176 | 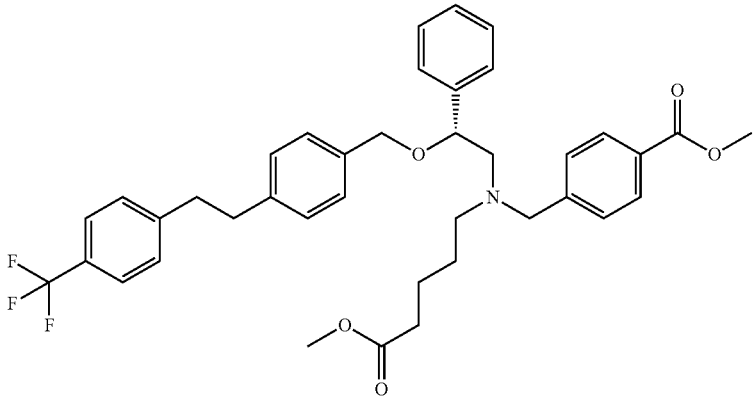 [SMILES: COC(=O)CCCCN(Cc1ccc(C(=O)OC)cc1)C[C@H](OCc1ccc(CCc2ccc(C(F)(F)F)cc2)cc1)c1ccccc1] | (CDCl₃) δ: 7.91 (2H, d, J = 8.2 Hz), 7.52 (2H, d, J = 8.2 Hz), 7.38-7.24 (9H, m), 7.21 (2H, d, J = 8.1 Hz), 7.11 (2H, d, J = 8.1 Hz), 4.48 (1H, dd, J = 7.1, 5.0 Hz), 4.42 (1H, d, J = 11.5 Hz), 4.24 (1H, d, J = 11.5 Hz), 3.90 (3H, s), 3.76 (1H, d, J = 14.3 Hz), 3.64 (3H, s), 3.61 (1H, d, J = 14.3 Hz), 3.03-2.88 (4H, m), 2.88 (1H, dd, J = 14.3, 7.1 Hz), 2.67 (1H, dd, J = 14.3, 5.0 Hz), 2.56-2.40 (2H, m), 2.18 (2H, t, J = 7.2 Hz), 1.63-1.33 (4H, m). |

TABLE 31

| Reference Example | Structural formula | ¹H-NMR |
|---|---|---|
| 177 | 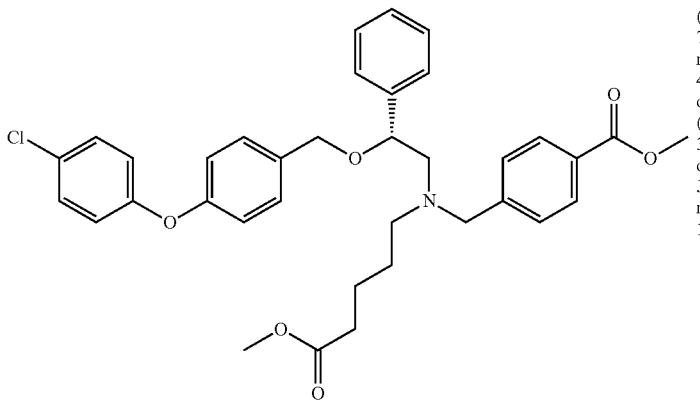 | (CDCl₃) δ: 7.91 (2H, d, J = 8.4 Hz), 7.38-7.23 (11H, m), 6.96-6.90 (4H, m), 4.48 (1H, dd, J = 7.1, 4.9 Hz), 4.41 (1H, d, J = 11.5 Hz), 4.25 (1H, d, J = 11.5 Hz), 3.91 (3H, s), 3.76 (1H, d, J = 14.5 Hz), 3.63 (3H, s), 3.61 (1H, d, J = 14.5 Hz), 2.89 (1H, dd, J = 13.9, 7.1 Hz), 2.67 (1H, dd, J = 13.9, 4.9 Hz), 2.53-2.42 (2H, m), 2.18 (2H, t, J = 7.3 Hz), 1.59-1.34 (4H, m). |

TABLE 31-continued

| Reference Example | Structural formula | $^1$H-NMR |
|---|---|---|
| 178 | 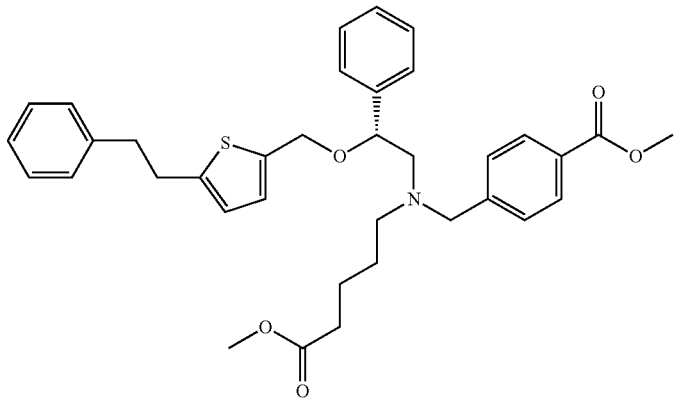 [SMILES: COC(=O)CCCCN(Cc1ccc(C(=O)OC)cc1)C[C@H](OCc1ccc(CCc2ccccc2)s1)c1ccccc1] | (CDCl$_3$) δ: 7.91 (2H, d, J = 8.4 Hz), 7.37-7.17 (12H, m), 6.68 (1H, d, J = 3.5 Hz), 6.60 (1H, d, J = 3.5 Hz), 4.52 (1H, dd, J = 7.2, 4.9 Hz), 4.52 (1H, d, J = 12.3 Hz), 4.34 (1H, d, J = 12.3 Hz), 3.89 (3H, s), 3.76 (1H, d, J = 14.3 Hz), 3.62 (3H, s), 3.61 (1H, d, J = 14.3 Hz), 3.11-3.04 (2H, m), 2.99-2.92 (2H, m), 2.86 (1H, dd, J = 13.8, 7.2 Hz), 2.66 (1H, dd, J = 13.8, 4.9 Hz), 2.54-2.40 (2H, m), 2.18 (2H, t, J = 7.3 Hz), 1.53-1.35 (4H, m). |
| 179 | 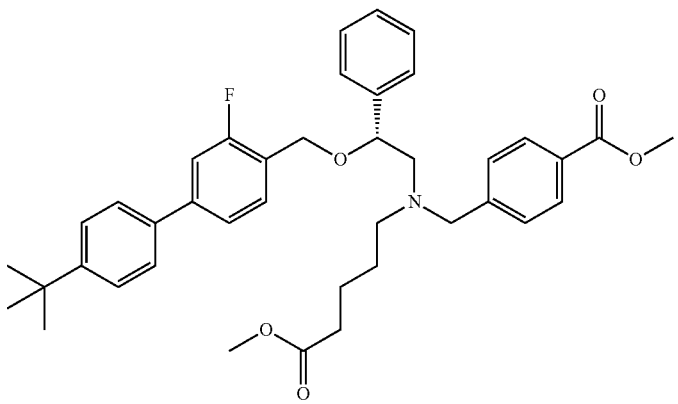 [SMILES: COC(=O)CCCCN(Cc1ccc(C(=O)OC)cc1)C[C@H](OCc1ccc(-c2ccc(C(C)(C)C)cc2)cc1F)c1ccccc1] | (CDCl$_3$) δ: 7.91 (2H, d, J = 8.2 Hz), 7.55-7.18 (14H, m), 4.54 (1H, dd, J = 7.5, 4.9 Hz), 4.50 (1H, d, J = 11.9 Hz), 4.40 (1H, d, J = 11.9 Hz), 3.89 (3H, s), 3.77 (1H, d, J = 14.3 Hz), 3.64 (1H, d, J = 14.3 Hz), 3.62 (3H, s), 2.90 (1H, dd, J = 13.9, 7.5 Hz), 2.68 (1H, dd, J = 13.9, 4.9 Hz), 2.56-2.38 (2H, m), 2.18 (2H, t, J = 7.2 Hz), 1.58-1.28 (4H, m), 1.36 (9H, s). |
| 180 | 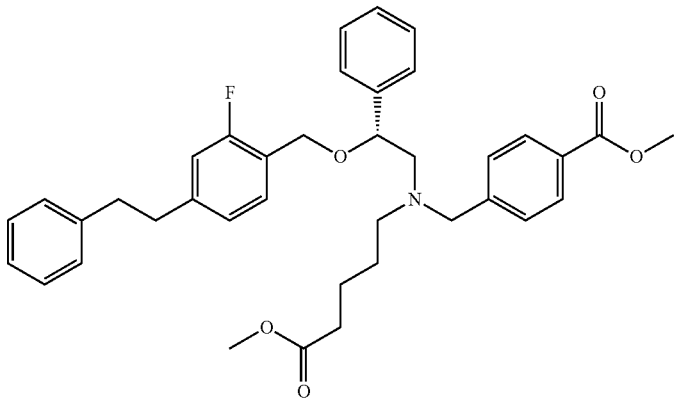 [SMILES: COC(=O)CCCCN(Cc1ccc(C(=O)OC)cc1)C[C@H](OCc1ccc(CCc2ccccc2)cc1F)c1ccccc1] | (CDCl$_3$) δ: 7.91 (2H, d, J = 8.2 Hz), 7.38-7.12 (13H, m), 6.92 (1H, dd, J = 8.0, 1.3 Hz), 6.84 (1H, dd, J = 10.8, 1.3 Hz), 4.51 (1H, dd, J = 7.1, 0 4.9 Hz), 4.44 (1H, d, J = 11.9 Hz), 4.33 (1H, d, J = 11.9 Hz), 3.90 (3H, s), 3.76 (1H, d, J = 14.3 Hz), 3.63 (3H, s), 3.61 (1H, d, J = 14.3 Hz), 2.90 (4H, s), 2.87 (1H, dd, J = 14.0, 7.1 Hz), 2.66 (1H, dd, J = 14.0, 4.9 Hz), 2.55-2.38 (2H, m), 2.18 (2H, t, J = 7.2 Hz), 1.62-1.32 (4H, m). |

TABLE 32
| Reference Example | Structural formula | ¹H-NMR |
|---|---|---|
| 181 | 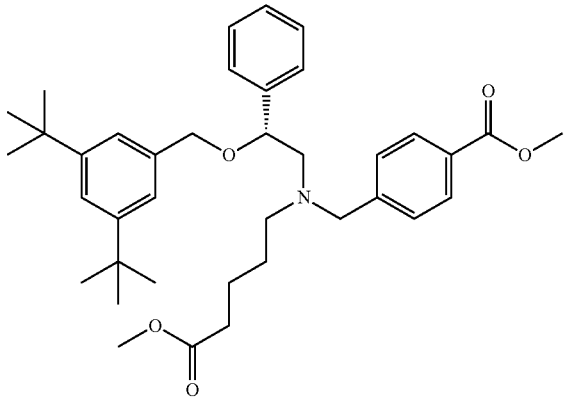 [SMILES: COC(=O)CCCCN(Cc1ccc(C(=O)OC)cc1)C[C@H](OCc1cc(C(C)(C)C)cc(C(C)(C)C)c1)c1ccccc1] | (CDCl₃) δ: 7.90 (2H, d, J = 8.2 Hz), 7.40-7.20 (8H, m), 7.13 (2H, d, J = 1.8 Hz), 4.52 (1H, dd, J = 7.1, 5.1 Hz), 4.44 (1H, d, J = 11.4 Hz), 4.28 (1H, d, J = 11.4 Hz), 3.90 (3H, s), 3.80 (1H, d, J = 14.5 Hz), 3.65 (1H, d, J = 14.5 Hz), 3.63 (3H, s), 2.90 (1H, dd, J = 13.9, 7.1 Hz), 2.70 (1H, dd, J = 13.9, 5.1 Hz), 2.57-2.40 (2H, m), 2.17 (2H, t, J = 7.2 Hz), 1.57-1.08 (4H, m), 1.29 (18H, s). |
| 182 | 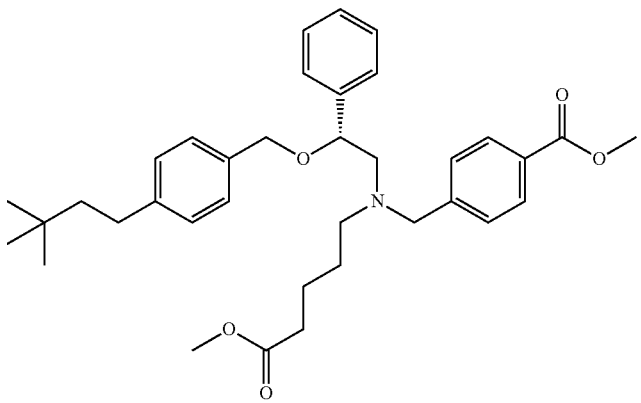 [SMILES: COC(=O)CCCCN(Cc1ccc(C(=O)OC)cc1)C[C@H](OCc1ccc(CCC(C)(C)C)cc1)c1ccccc1] | (CDCl₃) δ: 7.91 (2H, d, J = 8.2 Hz), 7.38-7.24 (7H, m), 7.20 (2H, d, J = 8.1 Hz), 7.13 (2H, d, J = 8.1 Hz), 4.48 (1H, dd, J = 7.1, 5.1 Hz), 4.41 (1H, d, J = 11.5 Hz), 4.23 (1H, d, J = 11.5 Hz), 3.91 (3H, s), 3.76 (1H, d, J = 14.5 Hz), 3.63 (3H, s), 3.61 (1H, d, J = 14.5 Hz), 2.87 (1H, dd, J = 13.8, 7.1 Hz), 2.66 (1H, dd, J = 13.8, 5.1 Hz), 2.61-2.39 (4H, m), 2.18 (2H, t, J = 7.2 Hz), 1.65-1.31 (6H, m), 0.93 (9H, d, J = 13.2 Hz). |
| 183 | 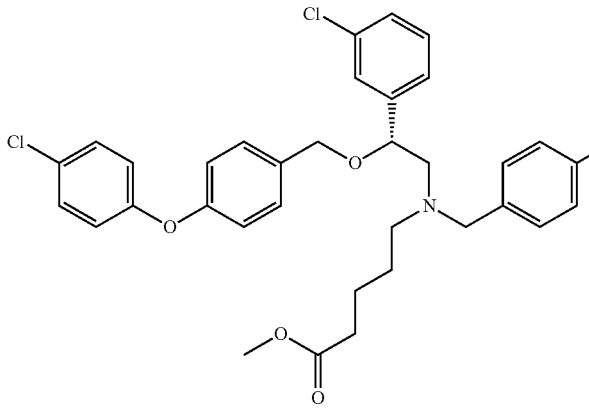 | (CDCl₃) δ: 7.91 (2H, d, J = 8.2 Hz), 7.31-7.22 (9H, m), 7.17-7.10 (1H, m), 6.97-6.90 (4H, m), 4.42 (2H, dd, J = 7.0, 5.2 Hz), 4.40 (2H, d, J = 11.5 Hz), 4.25 (1H, d, J = 11.5 Hz), 3.91 (3H, s), 3.74 (1H, d, J = 14.5 Hz), 3.64 (3H, s), 3.59 (1H, d, J = 14.5 Hz), 2.85 (1H, dd, J = 13.8, 7.0 Hz), 2.64 (1H, dd, J = 13.8, 5.2 Hz), 2.47 (2H, td, J = 6.7, 2.5 Hz), 2.20 (2H, t, J = 7.2 Hz), 1.61-1.34 (6H, m). |

TABLE 32-continued

| Reference Example | Structural formula | ¹H-NMR |
|---|---|---|
| 184 | 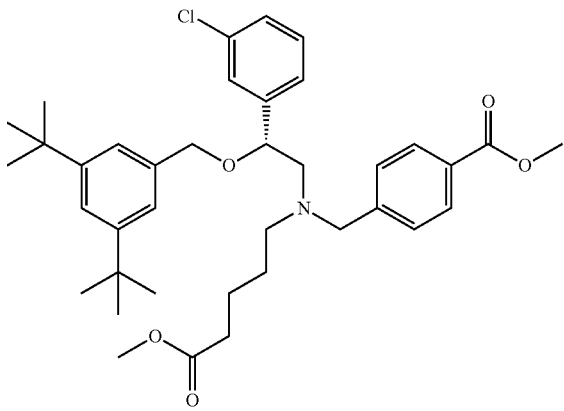 [SMILES: COC(=O)CCCCN(Cc1ccc(C(=O)OC)cc1)C[C@H](OCc1cc(C(C)(C)C)cc(C(C)(C)C)c1)c1cccc(Cl)c1] | (CDCl₃) δ: 7.90 (2H, d, J = 8.2 Hz), 7.37-7.32 (1H, m), 7.29-7.21 (5H, m), 7.17-7.08 (3H, m), 4.48-4.40 (1H, m), 4.44 (1H, d, J = 11.5 Hz), 4.29 (1H, d, J = 11.5 Hz), 3.90 (3H, s), 3.77 (1H, d, J = 14.3 Hz), 3.63 (3H, s), 3.62 (1H, d, J = 14.3 Hz), 2.86 (1H, dd, J = 14.0, 7.0 Hz), 2.67 (1H, dd, J = 14.0, 5.4 Hz), 2.53-2.43 (2H, m), 2.18 (2H, t, J = 7.0 Hz), 1.49-1.23 (4H, m), 1.29 (18H, s). |

TABLE 33

| Reference Example | Structural formula | ¹H-NMR |
|---|---|---|
| 185 | 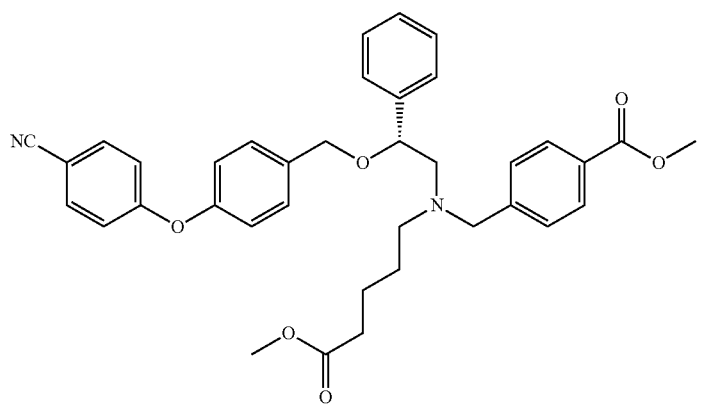 [SMILES: COC(=O)CCCCN(Cc1ccc(C(=O)OC)cc1)C[C@H](OCc1ccc(Oc2ccc(C#N)cc2)cc1)c1ccccc1] | (CDCl₃) δ: 7.91 (2H, d, J = 8.2 Hz), 7.59 (2H, d, J = 9.0 Hz), 7.38-7.26 (9H, m), 7.04-6.96 (4H, m), 4.49 (1H, dd, J = 7.3, 4.9 Hz), 4.43 (1H, d, J = 11.5 Hz), 4.29 (1H, d, J = 11.5 Hz), 3.91 (3H, s), 3.77 (1H, d, J = 14.5 Hz), 3.63 (3H, s), 3.63 (1H, d, J = 14.5 Hz), 2.90 (1H, dd, J = 14.0, 7.3 Hz), 2.68 (1H, dd, J = 14.0, 4.9 Hz), 2.49 (2H, td, J = 6.8, 2.7 Hz), 2.19 (2H, t, J = 7.3 Hz), 1.58-1.36 (4H, m). |
| 186 | 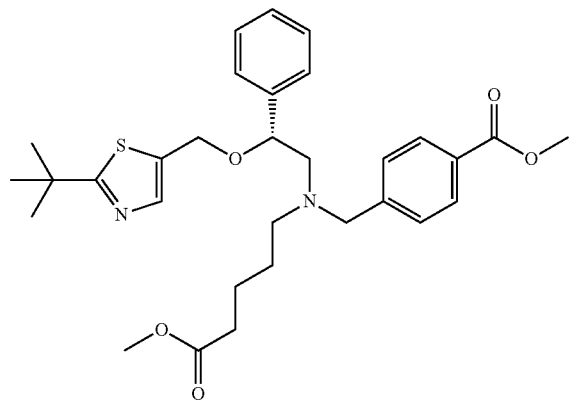 [SMILES: COC(=O)CCCCN(Cc1ccc(C(=O)OC)cc1)C[C@H](OCc1cnc(C(C)(C)C)s1)c1ccccc1] | (CDCl₃) δ: 7.92 (2H, d, J = 8.2 Hz), 7.43-7.19 (8H, m), 4.55 (1H, dd, J = 12.3, 0.7 Hz), 4.50 (1H, dd, J = 6.9, 4.7 Hz), 4.41 (1H, d, J = 12.3 Hz), 3.91 (3H, s), 3.76 (1H, d, J = 14.3 Hz), 3.64 (3H, s), 3.62 (1H, d, J = 14.3 Hz), 2.86 (1H, dd, J = 13.9, 7.3 Hz), 2.66 (1H, dd, J = 13.9, 4.8 Hz), 2.48 (2H, td, J = 6.8, 2.7 Hz), 2.20 (2H, t, J = 7.3 Hz), 1.59-1.34 (4H, m), 1.42 (9H, s). |

TABLE 33-continued

| Reference Example | Structural formula | ¹H-NMR |
|---|---|---|
| 187 | | (CDCl$_3$) δ: 7.91 (2H, d, J = 8.2 Hz), 7.38-7.24 (10H, m), 6.95 (2H, d, J = 8.8 Hz), 6.73 (1H, dd, J = 8.2, 2.4 Hz), 6.65 (1H, dd, J = 10.8, 2.4 Hz), 4.50 (1H, dd, J = 7.5, 4.8 Hz), 4.41 (1H, d, J = 11.7 Hz), 4.32 (1H, d, J = 11.7 Hz), 3.91 (3H, s), 3.76 (1H, d, J = 14.3 Hz), 3.63 (3H, s), 3.62 (1H, d, J = 14.3 Hz), 2.87 (1H, dd, J = 13.8, 7.5 Hz), 2.66 (1H, dd, J = 13.8, 4.8 Hz), 2.48 (2H, td, J = 6.7, 3.6 Hz), 2.18 (2H, t, J = 7.1 Hz), 1.57-1.37 (4H, m). |
| 188 | | (CDCl$_3$) δ: 7.91 (2H, d, J = 8.4 Hz), 7.29-7.23 (5H, m), 7.16-7.10 (1H, m), 6.66 (2H, dd, J = 10.5, 3.6 Hz), 4.53 (1H, d, J = 12.1 Hz), 4.47 (1H, dd, J = 7.2, 5.4 Hz), 4.34 (1H, d, J = 12.1 Hz), 4.10 (2H, q, J = 7.1 Hz), 3.91 (3H, s), 3.75 (1H, d, J = 14.2 Hz), 3.59 (1H, d, J = 14.2 Hz), 2.83 (1H, dd, J = 13.8, 7.2 Hz), 2.63 (1H, dd, J = 13.8, 5.4 Hz), 2.47 (2H, td, J = 6.9, 2.9 Hz), 2.19 (2H, t, J = 7.2 Hz), 1.53-1.38 (4H, m), 1.36 (9H, s), 1.24 (3H, t, J = 7.1 Hz). |

TABLE 34

| Reference Example | Structural formula | ¹H-NMR |
|---|---|---|
| 189 | | (CDCl$_3$) δ: 7.88 (2H, d, J = 8.4 Hz), 7.57 (1H, d, J = 8.2 Hz), 7.51 (1H, s), 7.28-7.21 (5H, m), 7.16-7.02 (3H, m), 4.67 (1H, d, J = 12.5 Hz), 4.51 (1H, dd, J = 6.3, 5.4 Hz), 4.47 (1H, d, J = 12.5 Hz), 4.09 (2H, q, J = 7.1 Hz), 3.91 (3H, s), 3.74 (1H, d, J = 14.4 Hz), 3.60 (1H, d, J = 14.4 Hz), 2.86 (1H, dd, J = 14.0, 6.3 Hz), 2.65 (1H, dd, J = 14.0, 5.4 Hz), 2.47 (2H, t, J = 6.6 Hz), 2.16 (2H, t, J = 7.2 Hz), 2.05-1.97 (1H, m), 1.53-1.37 (4H, m), 1.23 (3H, t, J = 7.1 Hz), 1.03-0.96 (2H, m), 0.79-0.72 (2H, m). |

TABLE 34-continued

| Reference Example | Structural formula | ¹H-NMR |
|---|---|---|
| 190 | 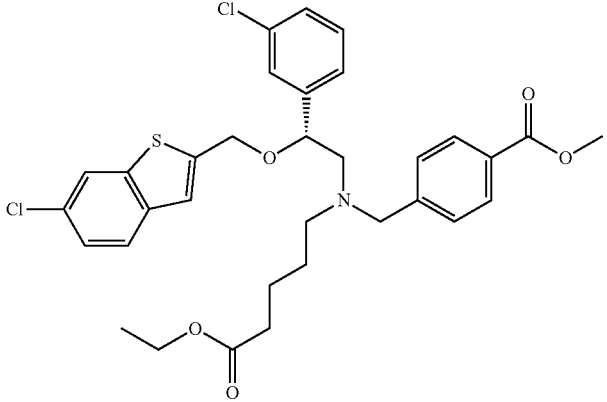 [SMILES: CCOC(=O)CCCCN(Cc1ccc(C(=O)OC)cc1)C[C@H](OCc1cc2ccc(Cl)cc2s1)c1cccc(Cl)c1] | (CDCl₃) δ: 7.87 (2H, d, J = 8.1 Hz), 7.79 (1H, d, J = 1.8 Hz), 7.61 (1H, d, J = 8.4 Hz), 7.32-7.22 (6H, m), 7.15-7.12 (1H, m), 7.06 (1H, s), 4.66 (1H, d, J = 12.8 Hz), 4.48 (1H, d, J = 12.8 Hz), 4.48 (1H, dd, J = 6.6, 5.1 Hz), 4.10 (2H, q, J = 7.1 Hz), 3.91 (3H, s), 3.74 (1H, d, J = 14.1 Hz), 3.61 (1H, d, J = 14.1 Hz), 2.87 (1H, dd, J = 13.8, 6.6 Hz), 2.66 (1H, dd, J = 13.8, 5.1 Hz), 2.48 (2H, t, J = 6.3 Hz), 2.17 (2H, t, J = 7.1 Hz), 1.53-1.39 (4H, m), 1.23 (3H, t, J = 7.1 Hz). |

Reference Example 191

Methyl 4-{[N-[(2R)-2-(3-chlorophenyl)-2-[5-(4-methylphenyloxy)thiophen-2-ylmethoxy]ethyl]-N-(4-ethoxycarbonylbutyl)amino]methyl}benzoate Reference Example 84 (37 mg) was dissolved in THF (1.0 mL), tri-n-butylphosphine (25 μL) was added, and the reaction solution was stirred at room temperature for 30 minutes. Then, methyl terephthalaldehydate (15 mg) was added and the reaction solution was stirred at the same temperature for 18 hours. Then, sodium borohydride (5 mg) and methanol (374 μL) was added, and then the reaction solution was stirred at the same temperature for 2 hours. A 1 mol/L aqueous solution of hydrochloric acid was added and the reaction solution was stirred, and then neutralized with a saturated aqueous solution of sodium hydrogen carbonate, and extracted with ethyl acetate. The combined organic layer was dried over anhydrous sodium sulfate, and then the solvent was evaporated under reduced pressure, and the residue was purified by silica gel column chromatography (20 to 40% ethyl acetate/hexane) to yield a crude product (a pale yellow oil). The crude product was dissolved in acetonitrile (1.0 mL), and potassium carbonate (12 mg) and methyl 5-bromovalerate (11 μL) were added, and the reaction solution was stirred and heated under reflux for 20 hours. The reaction solution was cooled to room temperature, quenched with water, and extracted with ethyl acetate, and then the solvent was evaporated under reduced pressure. The residue was purified by silica gel column chromatography (10 to 30% ethyl acetate/hexane) to yield the title compound (24 mg) as a colorless oil.

¹H-NMR(CDCl₃) δ: 7.91 (2H, d, J=8.2 Hz), 7.27-7.23 (5H, m), 7.14-7.07 (3H, m), 6.98 (2H, d, J=8.6 Hz), 6.58 (1H, d, J=3.7 Hz), 6.32 (1H, d, J=3.7 Hz), 4.47 (1H, d, J=12.3 Hz), 4.47 (1H, dd, J=6.7, 5.3 Hz), 4.29 (1H, d, J=12.3 Hz), 4.10 (2H, q, J=7.1 Hz), 3.91 (3H, s), 3.74 (1H, d, J=14.2 Hz), 3.60 (1H, d, J=14.2 Hz), 2.82 (1H, dd, J=13.9, 6.7 Hz), 2.63 (1H, dd, J=13.9, 5.3 Hz), 2.46 (2H, td, J=6.8, 2.9 Hz), 2.32 (3H, s), 2.18 (2H, t, J=7.1 Hz), 1.53-1.34 (4H, m), 1.23 (3H, t, J=7.1 Hz).

Reference Example 192

Methyl 4-{[N-(4-methoxycarbonylbutyl)-N-[2-[4-(2-phenylethyl)benzyloxy]-2-phenylethyl]amino]methyl}-2-fluorobenzoate Reference Example 86 (309 mg), and methyl 2-fluoro-4-formylbenzoate (164 mg) were dissolved in THF (3.0 mL), acetic acid (126 μL) was added, and the reaction solution was stirred at room temperature for 30 minutes. Then, sodium triacetoxyborohydride (474 mg) was added, and then the reaction solution was stirred at the same temperature for 17 hours. A saturated aqueous solution of sodium hydrogen carbonate was added and the reaction solution was stirred, and then extracted with chloroform. The combined organic layer was dried over anhydrous sodium sulfate, and then the solvent was evaporated under reduced pressure, and the residue was purified by silica gel column chromatography (10 to 60% ethyl acetate/hexane) to yield a product (156 mg) as a colorless oil. The product (150 mg) was dissolved in acetonitrile (2.0 mL), potassium carbonate (83 mg) and methyl 5-bromovalerate (67 μL) were added, and the reaction solution was stirred and heated under reflux for 2 days. The reaction solution was cooled to room temperature, quenched with water, and extracted with ethyl acetate. The combined organic layer was dried over anhydrous sodium sulfate, and then the solvent was evaporated under reduced pressure. The residue was purified by silica gel column chromatography (6 to 40% ethyl acetate/hexane) to yield the title compound (120 mg) as a colorless oil.

¹H-NMR(CDCl₃): 7.83-7.76 (1H, m), 7.39-7.24 (7H, m), 7.22-7.12 (7H, m), 7.05-6.98 (2H, m), 4.49 (1H, dd, J=7.1, 4.9 Hz), 4.42 (1H, d, J=11.5 Hz), 4.23 (1H, d, J=11.5 Hz), 3.92 (3H, s), 3.74 (1H, d, J=14.7 Hz), 3.64 (3H, s), 3.59 (1H, d, J=14.7H z), 2.91 (4H, s), 2.87 (1H, dd, J=13.5, 7.1 Hz), 2.66 (1H, dd, J=13.5, 4.9 Hz), 2.55-2.40 (2H, m), 2.20 (2H, t, J=7.2 Hz), 1.60-1.34 (4H, m).

Reference Example 193

Methyl 4-{[N-(4-benzyloxycarbonyl-3,3-dimethyl-butyl)-N-[2-[4-(2-phenylethyl)benzyloxy]-2-phenylethyl]amino]methyl}benzoate The title compound (303 mg) was manufactured as a colorless oil from Reference Example 102 (215 mg) and Reference Example 8 (105 mg) with a similar method to that of Reference Example 101.

¹H-NMR(CDCl₃) δ: 7.90 (2H, d, J=8.4 Hz), 7.37-7.27 (13H, m), 7.25-7.15 (6H, m), 7.12 (2H, d, J=8.2 Hz), 5.05 (2H, s), 4.46 (1H, dd, J=6.0, 4.9 Hz), 4.41 (1H, d, J=11.7 Hz), 4.22 (1H, d, J=11.7 Hz), 3.90 (3H, s), 3.72 (1H, d, J=14.5 Hz), 3.59 (1H, d, J=14.5 Hz), 2.89 (4H, s), 2.86 (1H, dd, J=13.7, 6.0 Hz), 2.63 (1H, dd, J=13.7, 4.9 Hz), 2.54-2.48 (2H, m), 2.15 (2H, s), 1.45 (2H, t, J=8.2 Hz), 0.89 (6H, s).

Reference Example 194

Methyl 4-{[N-(4-ethoxycarbonylbutyl)-N-[2-(3-methylphenyl)-2-[4-(2-phenylethyl)benzyloxy]ethyl]amino]methyl}benzoate Reference Example 164 (257 mg) was dissolved in 1,4-dioxane (4.0 mL), and methyl boronic acid (72 mg), tris(dibenzylideneacetone)dipalladium (37 mg), 2-dicyclohexyl phosphino-2',4',6'-triisopropyl biphenyl (38 mg) and potassium carbonate (166 mg) were added under argon atmosphere, and the reaction solution was stirred and heated under reflux for 18 hours. The reaction solution was cooled to room temperature, and filtered with Celite, and washed with ethyl acetate, and then the solvent was evaporated under reduced pressure. The residue was purified by silica gel column chromatography (5 to 50% ethyl acetate/hexane) to yield the title compound (201 mg) as a pale yellow oil.

¹H-NMR(CDCl₃) δ: 7.91 (2H, d, J=8.1 Hz), 7.30-7.25 (5H, m), 7.23-7.06 (10H, m), 4.45 (1H, dd, J=7.5, 4.6 Hz), 4.43 (1H, d, J=11.7 Hz), 4.24 (1H, d, J=11.7 Hz), 4.10 (2H, q, J=7.1 Hz), 3.90 (3H, s), 3.76 (1H, d, J=14.3 Hz), 3.61 (1H, d, J=14.3 Hz), 2.91 (4H, s), 2.87 (1H, dd, J=13.9, 7.5 Hz), 2.65 (1H, dd, J=13.9, 4.6 Hz), 2.50-2.45 (2H, m), 2.34 (3H, s), 2.17 (2H, t, J=7.2 Hz), 1.56-1.40 (4H, m), 1.23 (3H, t, J=7.1 Hz).

Reference Example 195

Ethyl 4-{[N-(4-ethoxycarbonylbutyl)-N-[2-(4-methylphenyl)-2-[4-(2-phenylethyl)benzyloxy]ethyl]amino]methyl}benzoate The title compound (155 mg) was manufactured as a pale yellow oil from Reference Example 145 (230 mg) with a similar method to that of Reference Example 194.

¹H-NMR(CDCl₃) δ: 7.90 (2H, d, J=8.2 Hz), 7.28-7.26 (3H, m), 7.21-7.12 (12H, m), 4.45 (1H, dd, J=7.1, 4.9 Hz), 4.41 (1H, d, J=11.5 Hz), 4.22 (1H, d, J=11.5 Hz), 4.09 (2H, q, J=7.1 Hz), 3.90 (3H, s), 3.76 (1H, d, J=14.5 Hz), 3.61 (1H, d, J=14.5 Hz), 2.90 (4H, s), 2.87 (1H, dd, J=13.6, 7.1 Hz), 2.64 (1H, dd, J=13.6, 4.9 Hz), 2.50-2.45 (2H, m), 2.36 (3H, s), 2.17 (2H, t, J=7.1 Hz), 1.48-1.40 (2H, m), 1.23 (3H, t, J=7.1 Hz).

Reference Example 196

Methyl 4-{[N-[(2R)-2-(3-cyanophenyl)-2-[4-(2-phenylethyl)benzyloxy]ethyl]-N-(4-ethoxycarbonyl-butyl)amino]methyl}benzoate Reference Example 170 (200 mg) was dissolved in DMF (3.0 mL), and tris(dibenzylideneacetone)dipalladium (57 mg), zinc cyanide (73 mg) and 2-dicyclohexylphosphino-2',4',6'-triisopropylbiphenyl (37 mg) were added under argon atmosphere, and the reaction solution was stirred at 130° C. under microwave radiation for 2 hours. The reaction solution was cooled to room temperature, quenched with a 28% aqueous solution of ammonium, and then extracted with diethyl ether. The combined organic layer was washed with saturated brine, and then dried over anhydrous sodium sulfate, and the solvent was evaporated under reduced pressure. The residue was purified by silica gel column chromatography (15 to 50% ethyl acetate/hexane) to yield the title compound (167 mg) as a pale yellow oil.

¹H-NMR(CDCl₃) δ: 7.90 (2H, d, J=8.4 Hz), 7.61-7.53 (2H, m), 7.49-7.39 (2H, m), 7.33-7.26 (2H, m), 7.23-7.13 (9H, m), 4.45 (1H, dd, J=6.7, 5.7 Hz), 4.40 (1H, d, J=11.5 Hz), 4.24 (1H, d, J=11.5 Hz), 4.11 (2H, q, J=7.1 Hz), 3.91 (3H, s), 3.73 (1H, d, J=14.2 Hz), 3.57 (1H, d, J=14.2 Hz), 2.91 (4H, s), 2.84 (1H, dd, J=13.9, 6.7 Hz), 2.63 (1H, dd, J=13.9, 5.7 Hz), 2.48 (2H, td, J=6.8, 3.1 Hz), 2.19 (2H, t, J=7.2 Hz), 1.54-1.38 (4H, m), 1.24 (3H, t, J=7.1 Hz).

The compounds of Reference Examples 197 and 198 manufactured with a similar method to that of Reference Example 196 using the compounds of Reference Examples 171 and 172 are shown in Table 35.

TABLE 35

| Reference Example | Structural formula | ¹H-NMR |
|---|---|---|
| 197 | 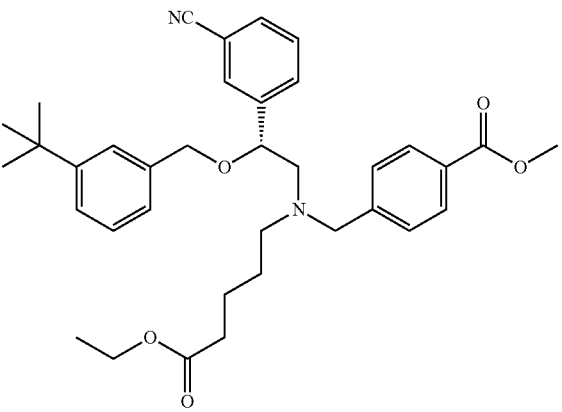 [SMILES: CCOC(=O)CCCCN(Cc1ccc(C(=O)OC)cc1)C[C@H](OCc1cccc(C(C)(C)C)c1)c1cccc(C#N)c1] | (CDCl₃) δ: 7.89 (2H, d, J = 8.4 Hz), 7.61-7.53 (2H, m), 7.49-7.38 (2H, m), 7.35-7.25 (3H, m), 7.20 (2H, d, J = 8.2 Hz), 7.08 (1H, d, J = 7.1 Hz), 4.46 (1H, dd, J = 6.7, 5.7 Hz), 4.43 (1H, d, J = 11.5 Hz), 4.29 (1H, d, J = 11.5 Hz), 4.11 (2H, q, J = 7.1 Hz), 3.91 (3H, s), 3.74 (1H, d, J = 14.0 Hz), 3.59 (1H, d, J = 14.0 Hz), 2.85 (1H, dd, J = 13.9, 6.7 Hz), 2.64 (1H, dd, J = 13.9, 5.7 Hz), 2.49 (2H, td, J = 6.8, 1.7 Hz), 2.19 (2H, t, J = 7.2 Hz), 1.52-1.37 (4H, m), 1.29 (9H, s), 1.24 (3H, t, J = 7.1 Hz). |

TABLE 35-continued

| Reference Example | Structural formula | $^1$H-NMR |
|---|---|---|
| 198 | (structure) | (CDCl$_3$) δ: 7.90 (2H, dd, J = 6.6, 1.8 Hz), 7.61-7.53 (2H, m), 7.49-7.39 (2H, m), 7.37-7.30 (2H, m), 7.24-7.19 (4H, m), 7.11 (1H, tt, J = 7.4, 1.3 Hz), 7.02-6.94 (4H, m), 4.45 (1H, dd, J = 6.7, 5.6 Hz), 4.38 (1H, d, J = 11.5 Hz), 4.25 (1H, d, J = 11.5 Hz), 4.11 (2H, q, J = 7.1 Hz), 3.91 (3H, s), 3.73 (1H, d, J = 14.1 Hz), 3.57 (1H, d, J = 14.1 Hz), 2.85 (1H, dd, J = 13.8, 6.7 Hz), 2.63 (1H, dd, J = 13.8, 5.6 Hz), 2.49 (2H, td, J = 6.8, 3.2 Hz), 2.20 (2H, t, J = 7.3 Hz), 1.55-1.41 (4H, m), 1.24 (3H, t, J = 7.1 Hz). |

Example 1

4-{[N-[2-(4-tert-Butylbenzyloxy)-2-phenylethyl]-N-(4-carboxybutyl)amino]methyl}benzoic acid Reference Example 143 (270 mg) was dissolved in methanol (3.0 mL), a 2 mol/L aqueous solution of sodium hydroxide (0.9 mL) was added, and the reaction solution was stirred at 50° C. at 3 hours. The reaction solution was cooled to room temperature, and the solvent was evaporated under reduced pressure. The residue was adjusted to pH 4 with 2 mol/L hydrochloric acid, and then extracted with a mixed solution of methanol and chloroform (1:9), and dried over anhydrous sodium sulfate. The solvent was evaporated under reduced pressure, and then the residue was purified by silica gel column chromatography (2% to 10% methanol/chloroform) to yield the title compound (234 mg) as a white amorphous.

$^1$H-NMR(CD$_3$OD) δ: 7.99 (2H, d, J=8.2 Hz), 7.49-7.32 (9H, m), 7.25 (2H, d, J=8.2 Hz), 4.69 (1H, dd, J=9.8, 4.9 Hz), 4.45 (1H, d, J=11.4 Hz), 4.23 (1H, d, J=11.4 Hz), 4.15 (2H, s), 3.22 (1H, dd, J=13.7, 9.8 Hz), 3.02 (1H, dd, J=13.7, 4.9 Hz), 2.95-2.81 (2H, m), 2.25 (2H, t, J=7.0 Hz), 1.76-1.60 (2H, m), 1.57-1.44 (2H, m), 1.30 (9H, s). ESI-MS Found: m/z 518 (M+H)$^+$ The compounds of Examples 2 to 56 manufactured with a similar method to that of Example 1 using the compounds of corresponding Reference Examples are shown in Tables 36 to 56.

TABLE 36

| Example | Structural formula | $^1$H-NMR | ESI-MS (M + H)+ |
|---|---|---|---|
| 2 | (structure) | (DMSO-D$_6$) δ: 7.80 (2H, d, J = 8.2 Hz), 7.34-7.15 (16H, m), 4.54 (1H, dd, J = 7.2, 4.6 Hz), 4.31 (1H, d, J = 11.7 Hz), 4.24 (1H, d, J = 11.7 Hz), 3.70 (1H, d, J = 14.5 Hz), 3.63 (1H, d, J = 14.5 Hz), 2.85 (4H, s), 2.78 (1H, dd, J = 13.7, 7.2 Hz), 2.55 (1H, dd, J = 13.7, 4.6 Hz), 2.44-2.41 (2H, m), 2.12-2.04 (2H, m), 1.40-1.33 (4H, m). | 566 |

TABLE 36-continued
| Example | Structural formula | ¹H-NMR | ESI-MS (M + H)+ |
|---|---|---|---|
| 3 | 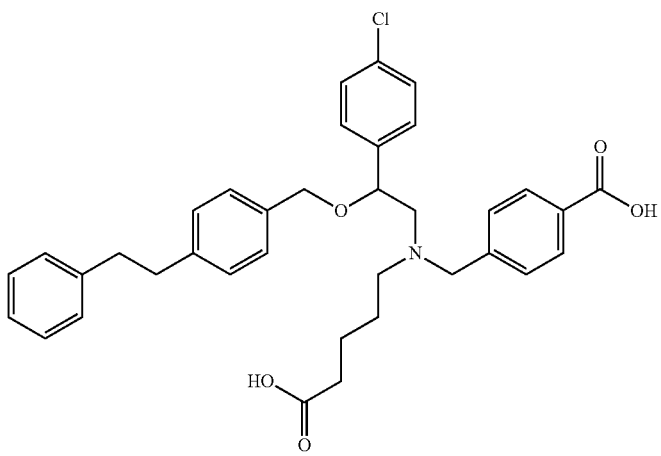 [SMILES: O=C(O)CCCCN(Cc1ccc(C(=O)O)cc1)CC(OCc1ccc(CCc2ccccc2)cc1)c1ccc(Cl)cc1] | (DMSO-D₆) δ: 7.80 (2H, d, J = 8.1 Hz), 7.40-7.15 (15H, m), 4.55 (1H, dd, J = 7.1, 5.3 Hz), 4.30 (1H, d, J = 11.8 Hz), 4.24 (1H, d, J = 11.8 Hz), 3.69 (1H, d, J = 14.4 Hz), 3.61 (1H, d, J = 14.4 Hz), 2.85 (4H, s), 2.77 (1H, dd, J = 13.7, 7.1 Hz), 2.54 (1H, dd, J = 13.7, 5.3 Hz), 2.45-2.38 (2H, m), 2.12-2.04 (2H, m), 1.31-1.28 (4H, m). | 601 |
| 4 | 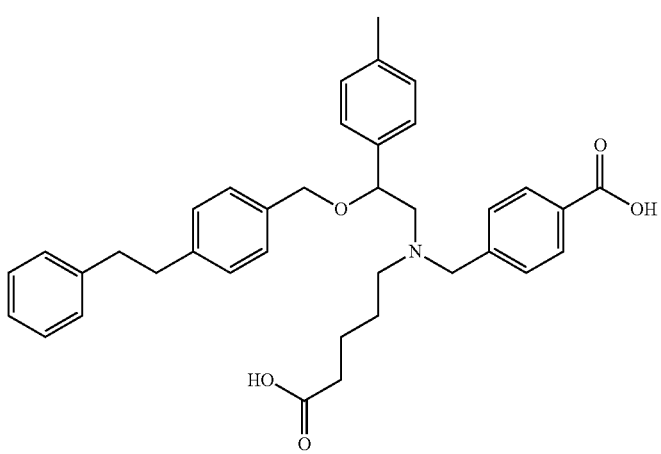 [SMILES: Cc1ccc(C(CN(CCCCC(=O)O)Cc2ccc(C(=O)O)cc2)OCc2ccc(CCc3ccccc3)cc2)cc1] | (DMSO-D₆) δ: 7.80 (2H, d, J = 7.5 Hz), 7.26-7.20 (15H, m), 4.50-4.47 (1H, m), 4.28 (1H, d, J = 11.6 Hz), 4.21 (1H, d, J = 11.6 Hz), 3.69 (1H, d, J = 14.3 Hz), 3.62 (1H, d, J = 14.3 Hz), 2.85 (4H, s), 2.76 (1H, dd, J = 14.1, 8.2 Hz), 2.56-2.48 (1H, m), 2.45-2.40 (2H, m), 2.28 (3H, s), 2.12-2.04 (2H, m), 1.38-1.35 (4H, m). | 580 |
| 5 | 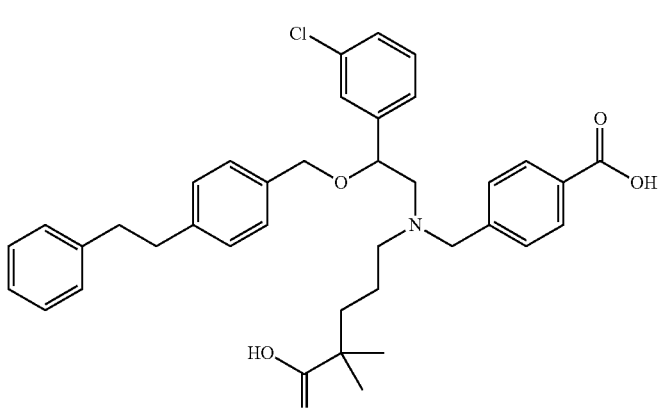 | (DMSO-D₆) δ: 7.80 (2H, d, J = 7.9 Hz), 7.42-7.33 (2H, m), 7.29-7.14 (13H, m), 4.56 (1H, dd, J = 6.6, 5.1 Hz), 4.33 (1H, d, J = 11.7 Hz), 4.27 (1H, d, J = 11.7 Hz), 3.69 (1H, d, J = 14.5 Hz), 3.60 (1H, d, J = 14.5 Hz), 2.86 (4H, s), 2.76 (1H, dd, J = 13.7, 6.6 Hz), 2.56 (1H, dd, J = 13.7, 5.1 Hz), 2.44-2.35 (2H, m), 1.33-1.25 (4H, m), 1.00 (6H, s). | 629 |

TABLE 37
| Example | Structural formula | ¹H-NMR | ESI-MS (M + H)+ |
|---|---|---|---|
| 6 | 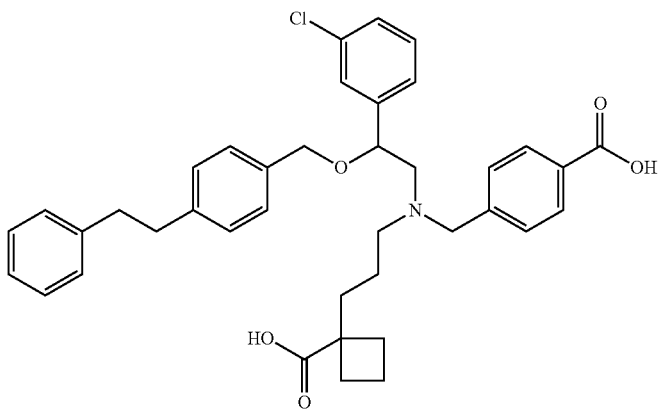 [SMILES: O=C(O)c1ccc(CN(CCCC2(C(=O)O)CCC2)CC(OCc2ccc(CCc3ccccc3)cc2)c2cccc(Cl)c2)cc1] | (DMSO-D$_6$) δ: 7.80 (2H, d, J = 8.1 Hz), 7.40-7.14 (15H, m), 4.57 (1H, dd, J = 7.1, 6.8 Hz), 4.33 (1H, d, J = 11.4 Hz), 4.27 (1H, d, J = 11.4 Hz), 3.69 (1H, d, J = 14.5 Hz), 3.60 (1H, d, J = 14.5 Hz), 2.86 (4H, s), 2.77 (1H, dd, J = 14.0, 7.1 Hz), 2.56 (1H, dd, J = 14.0, 6.8 Hz), 2.47-2.40 (2H, m), 2.28-2.20 (2H, m), 1.75-1.67 (4H, m), 1.59-1.51 (2H, m), 1.27-1.18 (2H, m). | 641 |
| 7 | 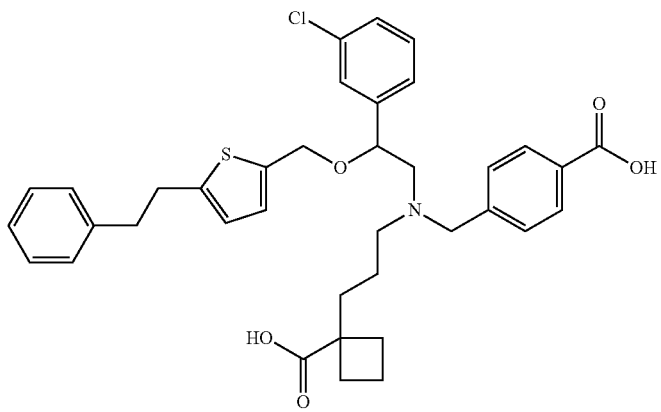 [SMILES: O=C(O)c1ccc(CN(CCCC2(C(=O)O)CCC2)CC(OCc2ccc(CCc3ccccc3)s2)c2cccc(Cl)c2)cc1] | (DMSO-D$_6$) δ: 7.81 (2H, d, J = 8.1 Hz), 7.32-7.24 (11H, m), 6.76 (1H, d, J = 3.3 Hz), 6.68 (1H, d, J = 3.3 Hz), 4.59 (1H, dd, J = 7.3, 6.0 Hz), 4.44 (1H, d, J = 12.1 Hz), 4.38 (1H, d, J = 12.1 Hz), 3.68 (1H, d, J = 14.8 Hz), 3.59 (1H, d, J = 14.8 Hz), 3.10-3.02 (2H, m), 2.94-2.85 (2H, m), 2.73 (1H, dd, J = 13.4, 7.3 Hz), 2.54 (1H, dd, J = 13.4, 6.0 Hz), 2.47-2.40 (2H, m), 2.29-2.20 (2H, m), 1.80-1.65 (4H, m), 1.60-1.50 (2H, m), 1.27-1.17 (2H, m). | 647 |
| 8 | 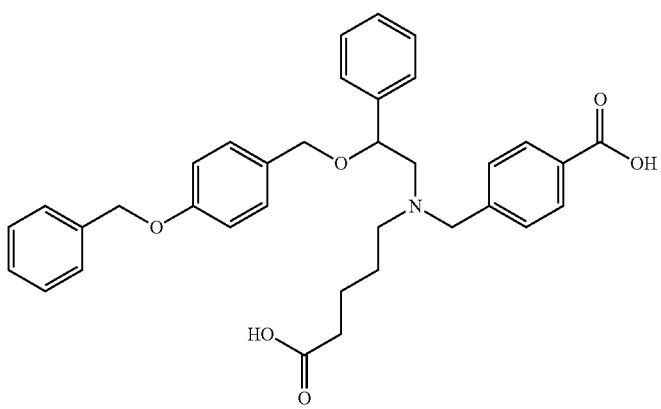 [SMILES: O=C(O)CCCCN(Cc1ccc(C(=O)O)cc1)CC(OCc1ccc(OCc2ccccc2)cc1)c1ccccc1] | (CD$_3$OD) δ: 7.98 (2H, d, J = 8.2 Hz), 7.47-7.26 (12H, m), 7.23 (2H, d, J = 8.6 Hz), 6.98 (2H, d, J = 8.6 Hz), 5.07 (2H, s), 4.65 (1H, dd, J = 9.3, 3.8 Hz), 4.40 (1H, d, J = 11.4 Hz), 4.18 (1H, d, J = 11.4 Hz), 4.10 (2H, s), 3.16 (1H, dd, J = 13.8, 9.3 Hz), 2.97 (1H, dd, J = 13.8, 3.8 Hz), 2.88-2.78 (2H, m), 2.24 (2H, t, J = 7.0 Hz), 1.73-1.57 (2H, m), 1.57-1.43 (2H, m). | 568 |

TABLE 38
| Example | Structural formula | ¹H-NMR | ESI-MS (M + H)+ |
|---|---|---|---|
| 9 | 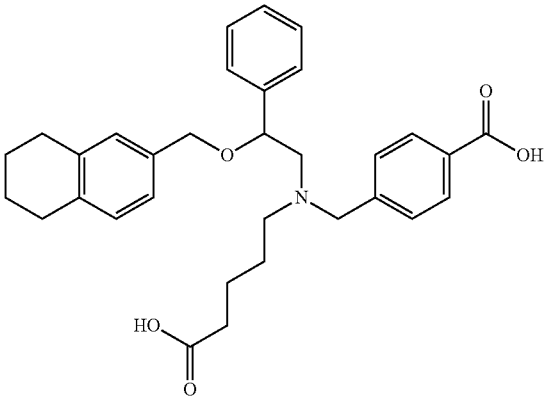 [SMILES: O=C(O)CCCCN(Cc1ccc(C(=O)O)cc1)CC(OCc1ccc2c(c1)CCCC2)c1ccccc1] | (CD$_3$OD) δ: 7.94 (2H, d, J = 8.4 Hz), 7.43-7.28 (7H, m), 7.04-6.96 (3H, m), 4.62 (1H, dd, J = 9.0, 4.0 Hz), 4.39 (1H, d, J = 11.4 Hz), 4.16 (1H, d, J = 11.4 Hz), 4.04 (1H, d, J = 13.9 Hz), 3.98 (1H, d, J = 13.9 Hz), 3.09 (1H, dd, J = 13.7, 9.0 Hz), 2.89 (1H, dd, J = 13.7, 4.0 Hz), 2.81-2.68 (6H, m), 2.20 (2H, t, J = 7.1 Hz), 1.83-1.72 (4H, m), 1.67-1.41 (4H, m). | 516 |
| 10 | 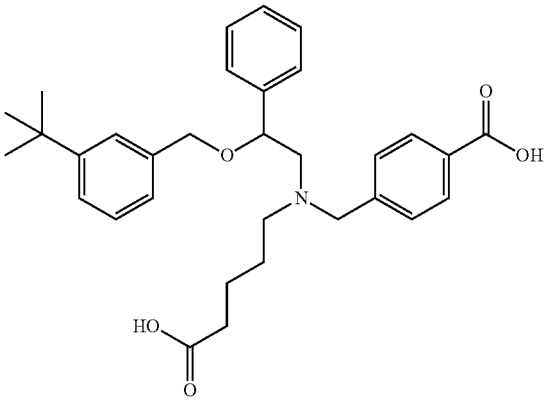 [SMILES: CC(C)(C)c1cccc(COC(CN(CCCCC(=O)O)Cc2ccc(C(=O)O)cc2)c2ccccc2)c1] | (CD$_3$OD) δ: 7.97-7.90 (2H, m), 7.46-7.22 (10H, m), 7.15-7.08 (1H, m), 4.62 (1H, dd, J = 9.0, 4.0 Hz), 4.44 (1H, d, J = 11.4 Hz), 4.28 (1H, d, J = 11.4 Hz), 4.03 (1H, d, J = 13.2 Hz), 3.98 (1H, d, J = 13.2 Hz), 3.09 (1H, dd, J = 13.7, 9.0 Hz), 2.89 (1H, dd, J = 13.7, 4.0 Hz), 2.82-2.68 (2H, m), 2.20 (2H, t, J = 6.9 Hz), 1.66-1.44 (4H, m), 1.29 (9H, s). | 518 |
| 11 | 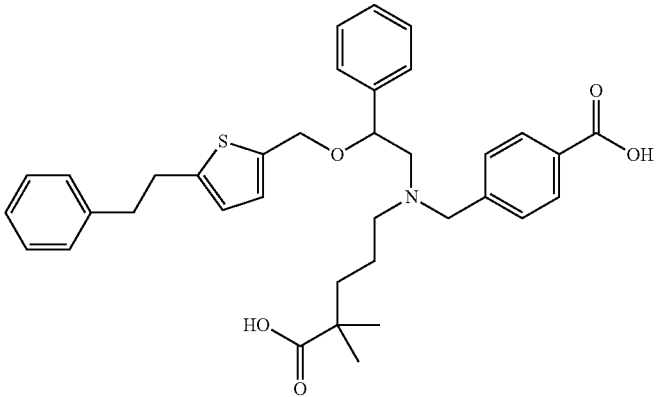 [SMILES: CC(C)(CCCN(Cc1ccc(C(=O)O)cc1)CC(OCc1ccc(CCc2ccccc2)s1)c1ccccc1)C(=O)O] | (DMSO-D$_6$) δ: 7.82 (2H, d, J = 8.1 Hz), 7.38-7.15 (12H, m), 6.74 (1H, d, J = 3.3 Hz), 6.68 (1H, d, J = 3.3 Hz), 4.57 (1H, dd, J = 7.3, 4.5 Hz), 4.43 (1H, d, J = 12.3 Hz), 4.34 (1H, d, J = 12.3 Hz), 3.71 (1H, d, J = 14.4 Hz), 3.62 (1H, d, J = 14.4 Hz), 3.09-3.03 (2H, m), 2.93-2.85 (2H, m), 2.75 (1H, dd, J = 13.4, 7.3 Hz), 2.54 (1H, dd, J = 13.4, 4.5 Hz), 2.44-2.37 (2H, m), 1.35-1.28 (4H, m), 1.01 (6H, s). | 600 |

TABLE 39
| Example | Structural formula | ¹H-NMR | ESI-MS (M + H)+ |
|---|---|---|---|
| 12 | 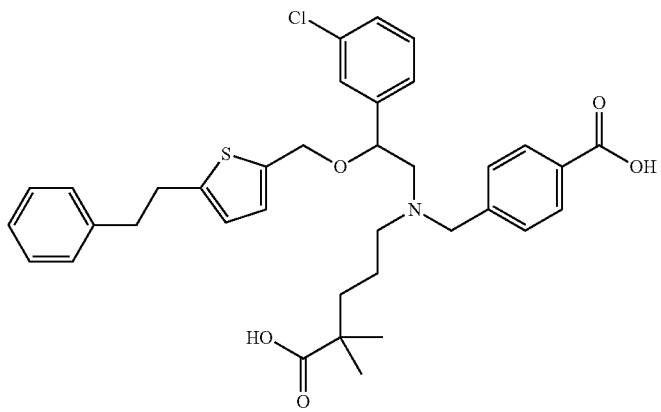 | (DMSO-D$_6$) δ: 7.81 (2H, d, J = 7.9 Hz), 7.41-7.13 (11H, m), 6.75 (1H, d, J = 3.0 Hz), 6.68 (1H, d, J = 3.0 Hz), 4.58 (1H, dd, J = 7.0, 5.8 Hz), 4.44 (1H, d, J = 12.5 Hz), 4.38 (1H, d, J = 12.5 Hz), 3.69 (1H, d, J = 14.3 Hz), 3.59 (1H, d, J = 14.3 Hz), 3.09-3.03 (2H, m), 2.93-2.86 (2H, m), 2.72 (1H, dd, J = 13.6, 7.0 Hz), 2.55 (1H, dd, J = 13.6, 5.8 Hz), 2.43-2.35 (2H, m), 1.32-1.25 (4H, m), 1.01 (6H, s). | 635 |
| 13 | 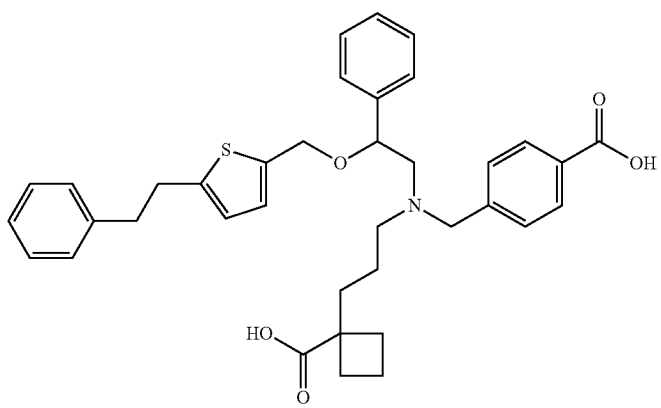 [SMILES: O=C(O)c1ccc(CN(CCCC2(C(=O)O)CCC2)CC(OCc2ccc(CCc3ccccc3)s2)c2ccccc2)cc1] | (DMSO-D$_6$) δ: 7.83 (2H, d, J = 8.2 Hz), 7.39-7.15 (12H, m), 6.74 (1H, d, J = 3.3 Hz), 6.68 (1H, d, J = 3.3 Hz), 4.58 (1H, dd, J = 7.4, 4.8 Hz), 4.43 (1H, d, J = 12.5 Hz), 4.35 (1H, d, J = 12.5 Hz), 3.71 (1H, d, J = 14.7 Hz), 3.63 (1H, d, J = 14.7 Hz), 3.09-3.03 (2H, m), 2.93-2.87 (2H, m), 2.75 (1H, dd, J = 13.8, 7.4 Hz), 2.53 (1H, dd, J = 13.8, 4.8 Hz), 2.47-2.40 (2H, m), 2.29-2.20 (2H, m), 1.79-1.67 (4H, m), 1.62-1.53 (2H, m), 1.27-1.18 (2H, m). | 612 |
| 14 | 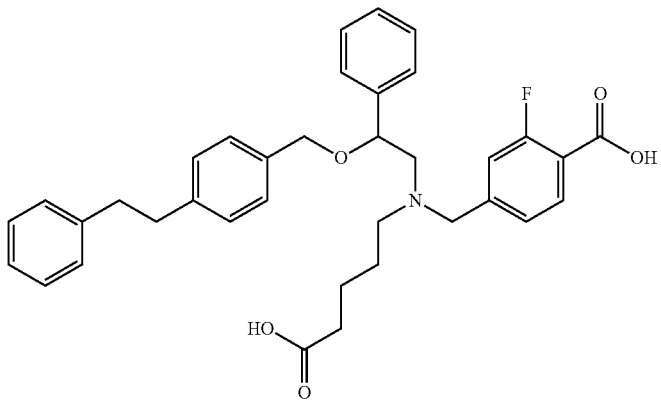 [SMILES: O=C(O)CCCCN(Cc1ccc(C(=O)O)c(F)c1)CC(OCc1ccc(CCc2ccccc2)cc1)c1ccccc1] | (CD$_3$OD) δ: 7.74 (1H, t, J = 7.8 Hz), 7.43-7.30 (5H, m), 7.23-7.09 (11H, m), 4.64 (1H, dd, J = 8.8, 3.8 Hz), 4.42 (1H, d, J = 11.2 Hz), 4.22 (1H, d, J = 11.2 Hz), 3.99 (2H, s), 3.11 (1H, dd, J = 13.7, 8.8 Hz), 2.91 (1H, dd, J = 13.7, 3.8 Hz), 2.88 (4H, s), 2.77 (2H, t, J = 7.0 Hz), 2.23 (2H, t, J = 7.0 Hz), 1.67-1.43 (4H, m). | 584 |

TABLE 40
| Example | Structural formula | ¹H-NMR | ESI-MS (M + H)+ |
|---|---|---|---|
| 15 | 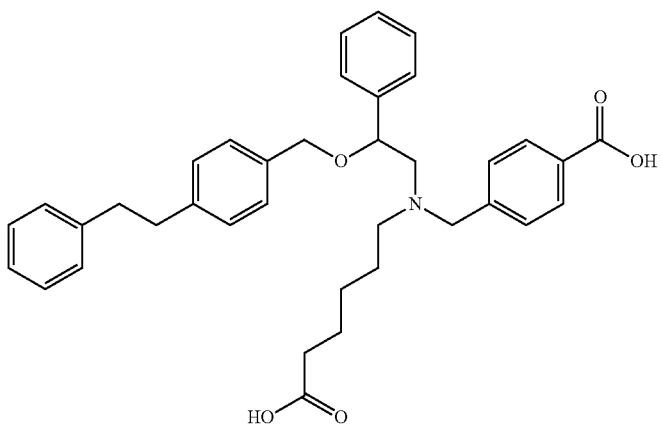 [SMILES: O=C(O)CCCCCN(Cc1ccc(C(=O)O)cc1)CC(OCc1ccc(CCc2ccccc2)cc1)c1ccccc1] | (DMSO-D$_6$) δ: 7.80 (2H, d, J = 8.4 Hz), 7.34-7.28 (8H, m), 7.21-7.14 (8H, m), 4.53 (1H, dd, J = 7.5, 4.8 Hz), 4.31 (1H, d, J = 11.4 Hz), 4.23 (1H, d, J = 11.4 Hz), 3.71 (1H, d, J = 14.4 Hz), 3.63 (1H, d, J = 14.4 Hz), 2.85 (4H, s), 2.79 (1H, dd, J = 13.6, 7.5 Hz), 2.56 (1H, dd, J = 13.6, 4.8 Hz), 2.41 (2H, t, J = 6.7 Hz), 2.10 (2H, t, J = 7.5 Hz), 1.39-1.11 (6H, m). | 580 |
| 16 | 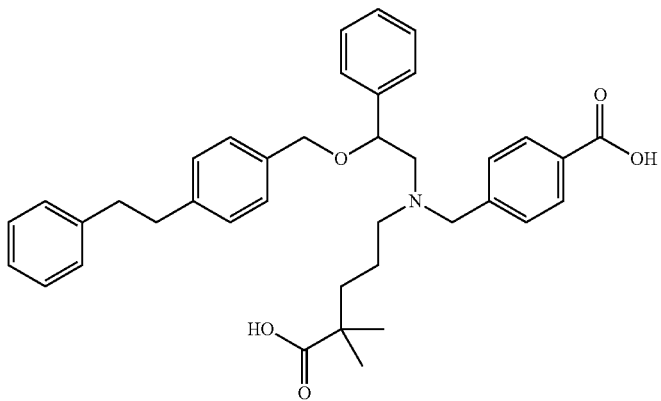 [SMILES: CC(C)(CCCN(Cc1ccc(C(=O)O)cc1)CC(OCc1ccc(CCc2ccccc2)cc1)c1ccccc1)C(=O)O] | (DMSO-D$_6$) δ: 7.81 (2H, d, J = 8.1 Hz), 7.38-7.13 (16H, m), 4.54 (1H, dd, J = 6.5, 5.2 Hz), 4.32 (1H, d, J = 11.7 Hz), 4.24 (1H, d, J = 11.7 Hz), 3.71 (1H, d, J = 14.3 Hz), 3.63 (1H, d, J = 14.3 Hz), 2.86 (4H, s), 2.79 (1H, dd, J = 13.7, 6.5 Hz), 2.56 (1H, dd, J = 13.7, 5.2 Hz), 2.45-2.38 (2H, m), 1.35-1.27 (4H, m), 1.01 (6H, s). | 594 |
| 17 | 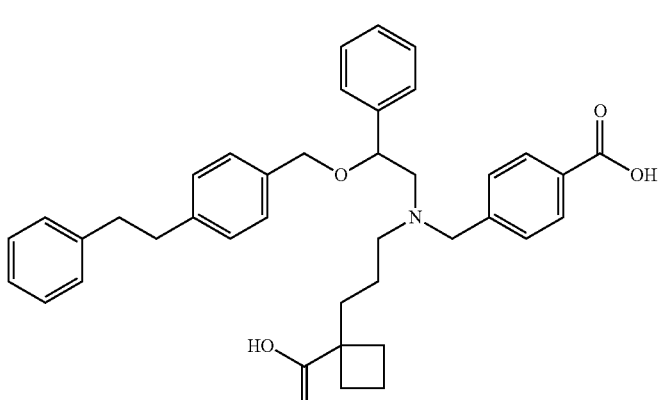 | (DMSO-D$_6$) δ: 7.82 (2H, d, J = 8.2 Hz), 7.39-7.14 (16H, m), 4.55 (1H, dd, J = 7.2, 4.8 Hz), 4.32 (1H, d, J = 11.7 Hz), 4.24 (1H, d, J = 11.7 Hz), 3.71 (1H, d, J = 14.1 Hz), 3.64 (1H, d, J = 14.1 Hz), 2.86 (4H, s), 2.79 (1H, dd, J = 13.5, 7.2 Hz), 2.55 (1H, dd, J = 13.5, 4.8 Hz), 2.48-2.41 (2H, m), 2.27-2.18 (2H, m), 1.77-1.54 (6H, m), 1.29-1.21 (2H, m). | 606 |

TABLE 40-continued

| Example | Structural formula | $^1$H-NMR | ESI-MS (M + H)+ |
|---|---|---|---|
| 18 | 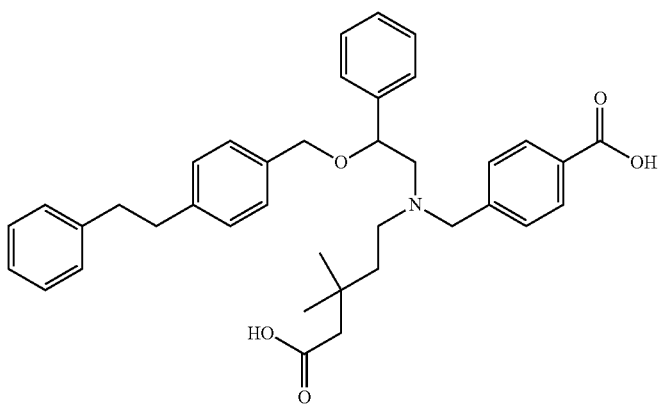 [SMILES: CC(C)(CCN(Cc1ccc(C(=O)O)cc1)CC(OCc1ccc(CCc2ccccc2)cc1)c1ccccc1)CC(=O)O] | (DMSO-D$_6$) δ: 7.81 (2H, d, J = 7.7 Hz), 7.36-7.14 (16H, m), 4.54 (1H, dd, J = 8.3, 4.9 Hz), 4.32 (1H, d, J = 12.0 Hz), 4.24 (1H, d, J = 12.0 Hz), 3.72 (1H, d, J = 14.9 Hz), 3.65 (1H, d, J = 14.9 Hz), 2.85 (4H, s), 2.76 (1H, dd, J = 15.3, 8.3 Hz), 2.55 (1H, dd, J = 15.3, 4.9 Hz), 2.48-2.42 (2H, m), 2.01 (2H, s), 1.48-1.40 (2H, m), 0.85 (6H, s). | 594 |

TABLE 41

| Example | Structural formula | $^1$H-NMR | ESI-MS (M + H)+ |
|---|---|---|---|
| 19 | 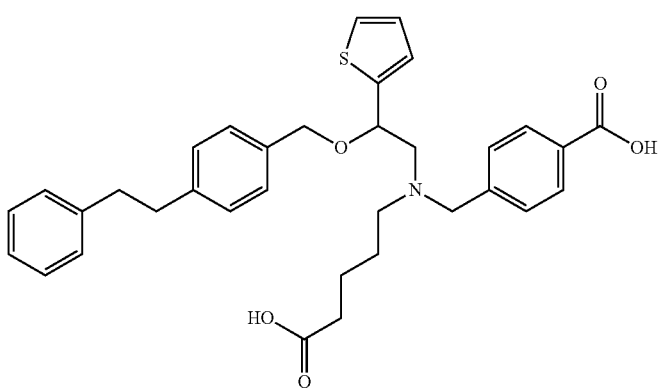 [SMILES: O=C(O)CCCCN(Cc1ccc(C(=O)O)cc1)CC(OCc1ccc(CCc2ccccc2)cc1)c1cccs1] | (CD$_3$OD) δ: 7.93 (2H, d, J = 8.2 Hz), 7.41 (1H, dd, J = 4.9, 1.2 Hz), 7.36 (2H, d, J = 8.2 Hz), 7.24-7.08 (9H, m), 7.05 (1H, dd, J = 3.6, 1.2 Hz), 7.01 (1H, dd, J = 4.9, 3.6 Hz), 4.86 (1H, dd, J = 9.3, 5.4 Hz), 4.47 (1H, d, J = 11.4 Hz), 4.27 (1H, d, J = 11.4 Hz), 3.92 (1H, d, J = 13.9 Hz), 3.85 (1H, d, J = 13.9 Hz), 3.10 (1H, dd, J = 13.9, 9.3 Hz), 2.90 (1H, dd, J = 13.9, 5.4 Hz), 2.88 (4H, s), 2.65 (2H, t, J = 6.9 Hz), 2.19 (2H, t, J = 6.8 Hz), 1.63-1.42 (4H, m). | 572 |
| 20 | 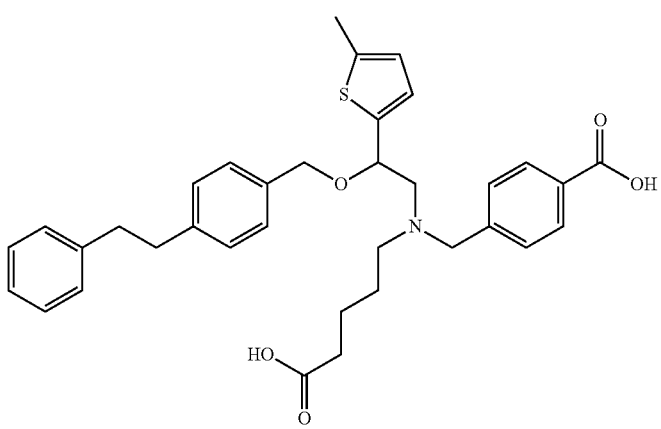 [SMILES: Cc1ccc(C(CN(CCCCC(=O)O)Cc2ccc(C(=O)O)cc2)OCc2ccc(CCc3ccccc3)cc2)s1] | (CD$_3$OD) δ: 7.95 (2H, d, J = 8.3 Hz), 7.38 (2H, d, J = 8.3 Hz), 7.24-7.08 (9H, m), 6.83 (1H, d, J = 3.5 Hz), 6.67 (1H, dd, J = 3.5, 1.1 Hz), 4.76 (1H, dd, J = 8.4, 4.6 Hz), 4.48 (1H, d, J = 11.4 Hz), 4.26 (1H, d, J = 11.4 Hz), 3.98 (1H, d, J = 13.7 Hz), 3.93 (1H, d, J = 13.7 Hz), 3.12 (1H, dd, J = 13.7, 8.4 Hz), 2.95 (1H, dd, J = 13.7, 4.6 Hz), 2.88 (4H, s), 2.71 (2H, t, J = 7.1 Hz), 2.46 (3H, d, J = 1.1 Hz), 2.21 (2H, t, J = 7.0 Hz), 1.65-1.43 (4H, m). | 586 |

TABLE 41-continued
| Example | Structural formula | ¹H-NMR | ESI-MS (M + H)+ |
|---|---|---|---|
| 21 | 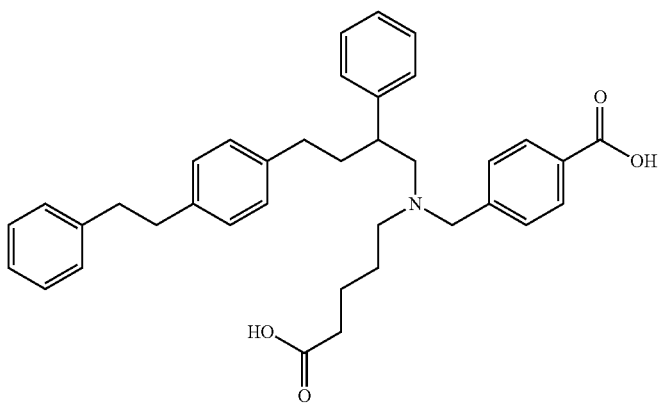 [SMILES: O=C(O)CCCCN(Cc1ccc(C(=O)O)cc1)CC(CCc1ccc(CCc2ccccc2)cc1)c1ccccc1] | (CD₃OD) δ: 7.90 (2H, d, J = 8.2 Hz), 7.35-7.08 (12H, m), 7.03 (2H, d, J = 7.8 Hz), 6.94 (2H, d, J = 7.8 Hz), 3.71 (2H, s), 2.84 (4H, s), 2.82-2.77 (3H, m), 2.51 (2H, t, J = 6.0 Hz), 2.45-2.23 (2H, m), 2.15 (2H, t, J = 6.5 Hz), 2.10-1.97 (1H, m), 1.84-1.72 (1H, m), 1.51-1.38 (4H, m). | 564 |
TABLE 42
| Example | Structural formula | ¹H-NMR | ESI-MS (M + H)+ |
|---|---|---|---|
| 22 | 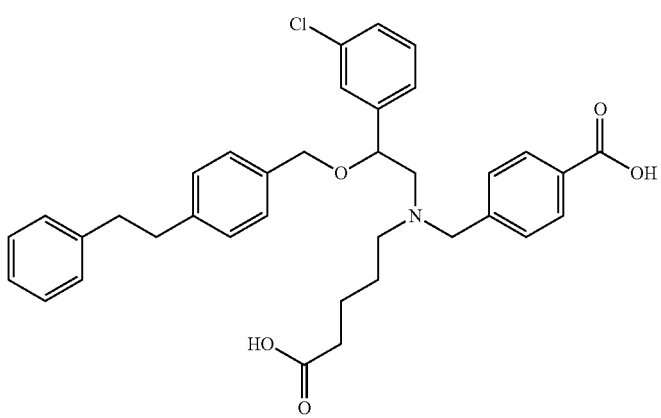 [SMILES: O=C(O)CCCCN(Cc1ccc(C(=O)O)cc1)CC(OCc1ccc(CCc2ccccc2)cc1)c1cccc(Cl)c1] | (DMSO-D₆) δ: 7.79 (2H, d, J = 8.1 Hz), 7.40-7.13 (15H, m), 4.56 (1H, dd, J = 6.8, 6.0 Hz), 4.32 (1H, d, J = 11.7 Hz), 4.26 (1H, d, J = 11.7 Hz), 3.69 (1H, d, J = 14.5 Hz), 3.60 (1H, d, J = 14.5 Hz), 2.85 (4H, s), 2.76 (1H, dd, J = 13.2, 6.8 Hz), 2.55 (1H, dd, J = 13.2, 6.0 Hz), 2.44-2.37 (2H, m), 2.10-2.05 (2H, m), 1.38-1.31 (4H, m). | 601 |
| 23 | 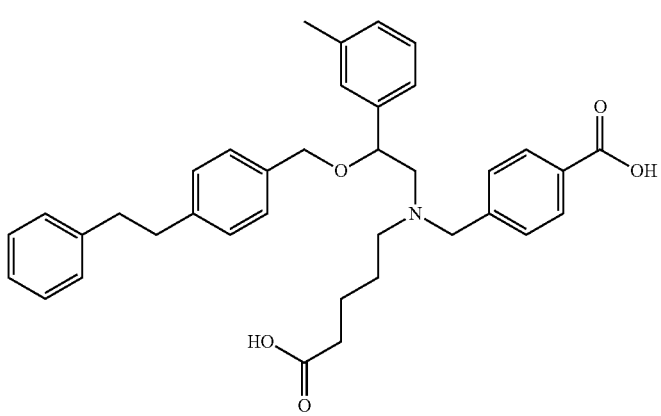 [SMILES: Cc1cccc(C(CN(CCCCC(=O)O)Cc2ccc(C(=O)O)cc2)OCc2ccc(CCc3ccccc3)cc2)c1] | (DMSO-D₆) δ: 7.80 (2H, d, J = 7.9 Hz), 7.30-7.05 (15H, m), 4.49 (1H, dd, J = 7.8, 6.8 Hz), 4.30 (1H, d, J = 11.9 Hz), 4.22 (1H, d, J = 11.9 Hz), 3.69 (1H, d, J = 14.1 Hz), 3.61 (1H, d, J = 14.1 Hz), 2.85 (4H, s), 2.76 (1H, dd, J = 14.0, 7.8 Hz), 2.52 (1H, dd, J = 14.0, 6.8 Hz), 2.46-2.38 (2H, m), 2.28 (3H, s), 2.12-2.05 (2H, m), 1.40-1.33 (4H, m). | 580 |

TABLE 42-continued

| Example | Structural formula | $^1$H-NMR | ESI-MS (M + H)+ |
|---|---|---|---|
| 24 | 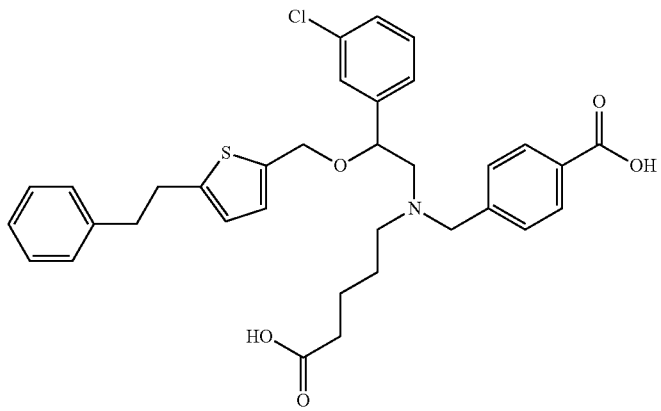 [SMILES: O=C(O)CCCCN(Cc1ccc(C(=O)O)cc1)CC(OCc1ccc(CCc2ccccc2)s1)c1cccc(Cl)c1] | (DMSO-D$_6$) δ: 7.81 (2H, d, J = 8.1 Hz), 7.43-7.14 (11H, m), 6.76 (1H, d, J = 3.3 Hz), 6.68 (1H, d, J = 3.3 Hz), 4.60 (1H, dd, J = 6.9, 5.4 Hz), 4.45 (1H, d, J = 12.5 Hz), 4.39 (1H, d, J = 12.5 Hz), 3.70 (1H, d, J = 14.5 Hz), 3.61 (1H, d, J = 14.5 Hz), 3.09-3.02 (2H, m), 2.94-2.85 (2H, m), 2.74 (1H, dd, J = 13.3, 6.9 Hz), 2.55 (1H, dd, J = 13.3, 5.4 Hz), 2.45-2.38 (2H, m), 2.13-2.05 (2H, m), 1.39-1.31 (4H, m). | 607 |

TABLE 43

| Example | Structural formula | $^1$H-NMR | ESI-MS (M + H)+ |
|---|---|---|---|
| 25 | 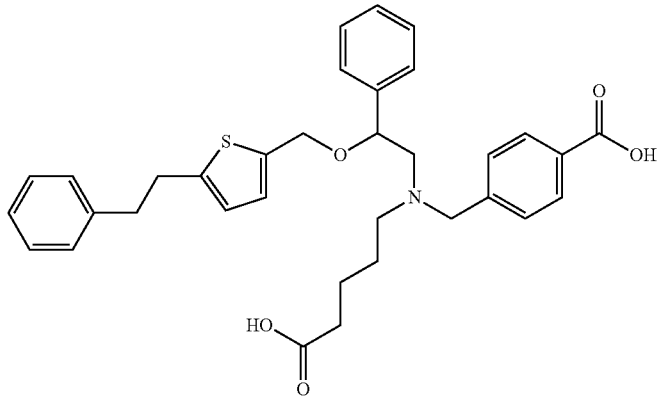 [SMILES: O=C(O)CCCCN(Cc1ccc(C(=O)O)cc1)CC(OCc1ccc(CCc2ccccc2)s1)c1ccccc1] | (DMSO-D$_6$) δ: 7.81 (2H, d, J = 8.1 Hz), 7.37-7.12 (12H, m), 6.73 (1H, d, J = 3.3 Hz), 6.66 (1H, d, J = 3.3 Hz), 4.57 (1H, dd, J = 7.1, 5.4 Hz), 4.42 (1H, d, J = 12.3 Hz), 4.34 (1H, d, J = 12.3 Hz), 3.71 (1H, d, J = 14.6 Hz), 3.62 (1H, d, J = 14.6 Hz), 3.09-3.01 (2H, m), 2.93-2.84 (2H, m), 2.75 (1H, dd, J = 13.9, 7.1 Hz), 2.54 (1H, dd, J = 13.9, 5.4 Hz), 2.46-2.38 (2H, m), 2.13-2.03 (2H, m), 1.41-1.32 (4H, m). | 572 |
| 26 | 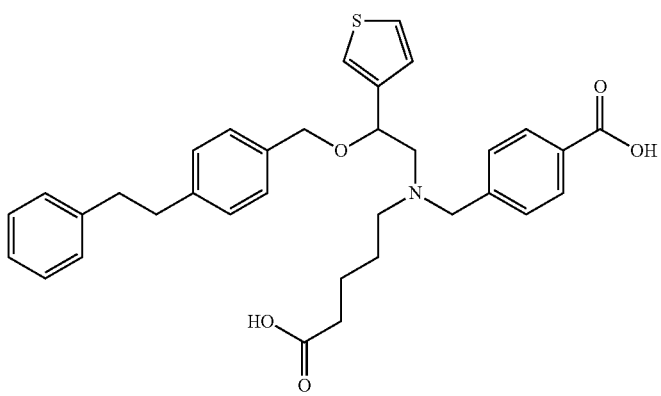 [SMILES: O=C(O)CCCCN(Cc1ccc(C(=O)O)cc1)CC(OCc1ccc(CCc2ccccc2)cc1)c1ccsc1] | (CD$_3$OD) δ: 7.96 (2H, d, J = 8.2 Hz), 7.48-7.35 (4H, m), 7.25-7.04 (10H, m), 4.76 (1H, dd, J = 9.0, 3.9 Hz), 4.43 (1H, d, J = 11.5 Hz), 4.24 (1H, d, J = 11.5 Hz), 4.02 (2H, s), 3.19 (1H, dd, J = 14.0, 9.0 Hz), 2.95 (1H, dd, J = 14.0, 3.9 Hz), 2.89 (4H, s), 2.82-2.71 (2H, m), 2.23 (2H, t, J = 7.1 Hz), 1.69-1.43 (4H, m). | 572 |

TABLE 43-continued

| Example | Structural formula | ¹H-NMR | ESI-MS (M + H)+ |
|---|---|---|---|
| 27 | | (CD₃OD) δ: 7.91 (2H, d, J = 8.2 Hz), 7.33 (2H, d, J = 8.2 Hz), 7.25-7.08 (9H, m), 6.85 (1H, d, J = 3.8 Hz), 6.82 (1H, d, J = 3.8 Hz), 4.67 (1H, dd, J = 7.0, 5.5 Hz), 4.50 (1H, d, J = 11.5 Hz), 4.31 (1H, d, J = 11.5 Hz), 3.81 (1H, d, J = 13.9 Hz), 3.73 (1H, d, J = 13.9 Hz), 2.94 (1H, dd, J = 13.9, 7.0 Hz), 2.89 (4H, s), 2.79 (1H, dd, J = 13.9, 5.5 Hz), 2.60-2.52 (2H, m), 2.19 (2H, t, J = 6.8 Hz), 1.57-1.43 (4H, m). | 606 |

TABLE 44

| Example | Structural formula | ¹H-NMR | ESI-MS (M + H)+ |
|---|---|---|---|
| 28 | | (CD₃OD) δ: 7.76 (1H, t, J = 7.8 Hz), 7.25-7.17 (4H, m), 7.17-7.05 (7H, m), 6.83 (1H, d, J = 3.4 Hz), 6.67 (1H, dd, J = 3.4, 1.2 Hz), 4.74 (1H, dd, J = 7.8, 5.0 Hz), 4.48 (1H, d, J = 11.4 Hz), 4.27 (1H, d, J = 11.4 Hz), 3.89 (1H, d, J = 14.1 Hz), 3.82 (1H, d, J = 14.1 Hz), 3.06 (1H, dd, J = 13.6, 7.8 Hz), 2.89 (1H, dd, J = 13.6, 5.0 Hz), 2.89 (4H, s), 2.65 (2H, t, J = 6.8 Hz), 2.46 (3H, d, J = 1.2 Hz), 2.21 (2H, t, J = 6.7 Hz), 1.62-1.43 (4H, m). | 604 |

TABLE 45

| Example | Structural formula | ¹H-NMR | ESI-MS (M + H)+ | Angle of rotation [α]_D |
|---|---|---|---|---|
| 29 | | (DMSO-D₆) δ: 7.81 (2H, d, J = 8.1 Hz), 7.41-7.14 (15H, m), 4.58 (1H, dd, J = 6.6, 5.2 Hz), 4.33 (1H, d, J = 11.8 Hz), 4.28 (1H, d, J = 11.8 Hz), 3.70 (1H, d, J = 14.5 Hz), 3.62 (1H, d, J = 14.5 Hz), 2.86 (4H, s), 2.78 (1H, dd, J = 13.7, 6.6 Hz), 2.57 (1H, dd, J = 13.7, 5.2 Hz), 2.46-2.40 (2H, m), 2.13-2.05 (2H, m), 1.40-1.33 (4H, m). | 601 | −29.9 (c = 0.25, MeOH) |

TABLE 45-continued

| Example | Structural formula | ¹H-NMR | ESI-MS (M + H)+ | Angle of rotation [α]_D |
|---|---|---|---|---|
| 30 | 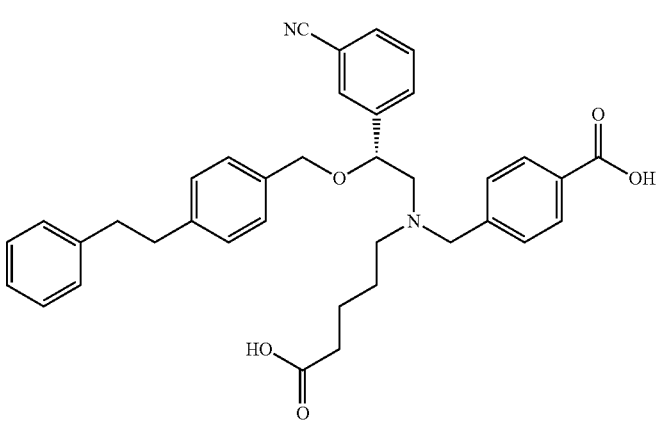 [SMILES: N#Cc1cccc([C@H](CN(CCCCC(=O)O)Cc2ccc(C(=O)O)cc2)OCc2ccc(CCc3ccccc3)cc2)c1] | (DMSO-D₆) δ: 7.82-7.68 (4H, m), 7.64 (1H, d, J = 7.9 Hz), 7.59-7.52 (1H, m), 7.29-7.14 (11H, m), 4.64 (1H, dd, J = 6.8, 5.9 Hz), 4.33 (1H, d, J = 12.0 Hz), 4.29 (1H, d, J = 12.0 Hz), 3.70 (1H, d, J = 14.5 Hz), 3.61 (1H, d, J = 14.5 Hz), 2.86 (4H, s), 2.80 (1H, dd, J = 13.7, 6.8 Hz), 2.60 (1H, dd, J = 13.7, 5.9 Hz), 2.45-2.37 (2H, m), 2.11-2.04 (2H, m), 1.37-1.30 (4H, m). | 591 | −23.9 (c = 0.26, MeOH) |
| 31 | 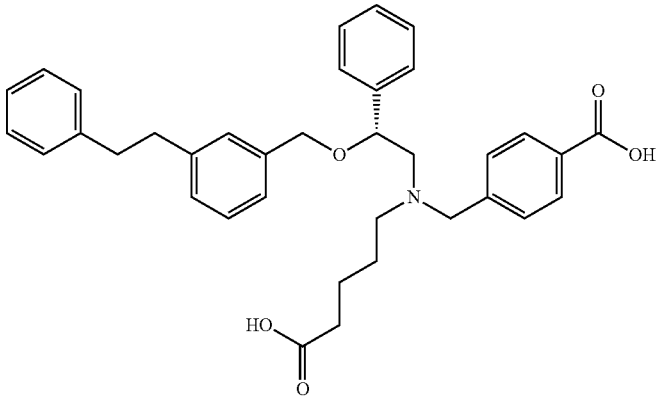 [SMILES: O=C(O)CCCCN(Cc1ccc(C(=O)O)cc1)C[C@H](OCc1cccc(CCc2ccccc2)c1)c1ccccc1] | (CD₃OD) δ: 7.95 (2H, d, J = 8.2 Hz), 7.41-7.11 (16H, m), 4.61 (1H, dd, J = 9.0, 3.8 Hz), 4.41 (1H, d, J = 11.4 Hz), 4.22 (1H, d, J = 11.4 Hz), 4.05 (1H, d, J = 14.1 Hz), 3.99 (1H, d, J = 14.1 Hz), 3.10 (1H, dd, J = 13.6, 9.0 Hz), 2.90 (1H, dd, J = 13.6, 3.8 Hz), 2.87 (4H, s), 2.76 (2H, t, J = 7.4 Hz), 2.20 (2H, t, J = 7.0 Hz), 1.67-1.43 (4H, m). | 566 | −20.8 (c = 0.25, CHCl₃) |

TABLE 46

| Example | Structural formula | ¹H-NMR | ESI-MS (M + H)+ | Angle of rotation [α]_D |
|---|---|---|---|---|
| 32 | 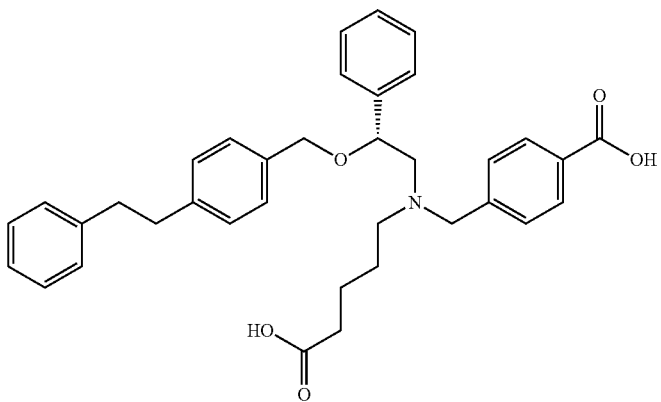 [SMILES: O=C(O)CCCCN(Cc1ccc(C(=O)O)cc1)C[C@H](OCc1ccc(CCc2ccccc2)cc1)c1ccccc1] | (CD₃OD) δ: 7.98-7.91 (2H, m), 7.42-7.27 (7H, m), 7.24-7.06 (9H, m), 4.62 (1H, dd, J = 8.9, 3.9 Hz), 4.41 (1H, d, J = 11.4 Hz), 4.21 (1H, d, J = 11.4 Hz), 4.03 (1H, d, J = 13.6 Hz), 3.98 (1H, d, J = 13.6 Hz), 3.10 (1H, dd, J = 13.8, 8.9 Hz), 2.90 (1H, dd, J = 13.8, 3.9 Hz), 2.88 (4H, s), 2.76 (2H, t, J = 7.4 Hz), 2.21 (2H, t, J = 7.0 Hz), 1.70-1.40 (4H, m). | 566 | −32.6 (c = 0.57, CHCl₃) |

TABLE 46-continued

| Example | Structural formula | ¹H-NMR | ESI-MS (M + H)+ | Angle of rotation [α]$_D$ |
|---|---|---|---|---|
| 33 | | (CD$_3$OD) δ: 8.05-7.92 (2H, m), 7.52-7.27 (7H, m), 7.27-7.05 (9H, m), 4.65 (1H, dd, J = 9.4, 3.2 Hz), 4.43 (1H, d, J = 11.4 Hz), 4.22 (1H, d, J = 11.4 Hz), 4.10 (2H, s), 3.18 (1H, dd, J = 13.7, 9.4 Hz), 2.98 (1H, dd, J = 13.7, 3.2 Hz), 2.94-2.78 (6H, m), 2.24 (2H, t, J = 7.1 Hz), 1.73-1.58 (2H, m), 1.58-1.44 (2H, m). | 566 | +34.0 (c = 0.59, CHCl$_3$) |
| 34 | | (DMSO-D$_6$) δ: 7.80 (2H, d, J = 8.2 Hz), 7.41-7.23 (9H, m), 7.09 (1H, d, J = 7.0 Hz), 4.59 (1H, dd, J = 7.0, 4.9 Hz), 4.35 (2H, s), 3.72 (1H, d, J = 14.4 Hz), 3.65 (1H, d, J = 14.4 Hz), 2.79 (1H, dd, J = 13.7, 7.0 Hz), 2.59 (1H, dd, J = 13.7, 4.9 Hz), 2.48-2.41 (2H, m), 2.12-2.05 (2H, m), 1.40-1.33 (4H, m), 1.24 (9H, s). | 553 | −23.8 (c = 0.32, MeOH) |

TABLE 47

| Example | Structural formula | ¹H-NMR | ESI-MS (M + H)+ | Angle of rotation [α]$_D$ |
|---|---|---|---|---|
| 35 | | (DMSO-D$_6$) δ: 7.81-7.53 (6H, m), 7.32-7.22 (5H, m), 7.09 (1H, d, J = 7.0 Hz), 4.66 (1H, dd, J = 7.0, 5.4 Hz), 4.36 (2H, s), 3.72 (1H, d, J = 14.8 Hz), 3.64 (1H, d, J = 14.8 Hz), 2.81 (1H, dd, J = 13.5, 7.0 Hz), 2.62 (1H, dd, J = 13.5, 5.4 Hz), 2.47-2.40 (2H, m), 2.11-2.04 (2H, m), 1.37-1.29 (4H, m), 1.24 (9H, s). | 543 | −17.4 (c = 0.14, MeOH) |

TABLE 47-continued

| Example | Structural formula | ¹H-NMR | ESI-MS (M + H)+ | Angle of rotation [α]$_D$ |
|---|---|---|---|---|
| 36 | | (DMSO-D$_6$) δ: 7.80 (2H, d, J = 8.2 Hz), 7.41-7.26 (10H, m), 7.17-7.11 (1H, m), 7.01-6.94 (4H, m), 4.61 (1H, dd, J = 6.4, 5.0 Hz), 4.33 (2H, s), 3.71 (1H, d, J = 14.2 Hz), 3.63 (1H, d, J = 14.2 Hz), 2.79 (1H, dd, J = 13.7, 6.4 Hz), 2.57 (1H, dd, J = 13.7, 5.0 Hz), 2.47-2.40 (2H, m), 2.13-2.06 (2H, m), 1.41-1.33 (4H, m). | 589 | −21.1 (c = 0.12, MeOH) |
| 37 | | (DMSO-D$_6$) δ: 7.82-7.70 (4H, m), 7.65 (1H, d, J = 8.1 Hz), 7.59-7.53 (1H, m), 7.42-7.35 (2H, m), 7.32 (2H, d, J = 8.1 Hz), 7.24 (2H, d, J = 8.1 Hz), 7.16-7.10 (1H, m), 7.00-6.95 (4H, m), 4.67 (1H, dd, J = 6.2, 5.9 Hz), 4.34 (2H, s), 3.71 (1H, d, J = 14.3 Hz), 3.62 (1H, d, J = 14.3 Hz), 2.81 (1H, dd, J = 13.8, 6.2 Hz), 2.60 (1H, dd, J = 13.8, 5.9 Hz), 2.46-2.39 (2H, m), 2.12-2.05 (2H, m), 1.38-1.31 (4H, m). | 579 | −15.5 (c = 0.17, MeOH) |

TABLE 48

| Example | Structural formula | ¹H-NMR | ESI-MS (M + H)+ | Angle of rotation [α]$_D$ |
|---|---|---|---|---|
| 38 | | (CD$_3$OD) δ: 7.95 (2H, d, J = 8.2 Hz), 7.43-7.30 (7H, m), 7.23 (2H, d, J = 8.2 Hz), 7.16 (2H, d, J = 8.2 Hz), 4.64 (1H, dd, J = 9.3, 3.9 Hz), 4.43 (1H, d, J = 11.3 Hz), 4.21 (1H, d, J = 11.3 Hz), 4.05 (1H, d, J = 13.9 Hz), 3.99 (1H, d, J = 13.9 Hz), 3.12 (1H, dd, J = 13.7, 9.3 Hz), 2.91 (1H, dd, J = 13.7, 3.9 Hz), 2.83-2.71 (2H, m), 2.64-2.58 (2H, m), 2.21 (2H, t, J = 7.0 Hz), 1.82-1.40 (11H, m), 1.31-1.09 (4H, m), 1.03-0.83 (2H, m). | 572 | −40.0 (c = 0.33, MeOH) |

TABLE 48-continued

| Example | Structural formula | $^1$H-NMR | ESI-MS (M + H)+ | Angle of rotation $[\alpha]_D$ |
|---|---|---|---|---|
| 39 | | (CD$_3$OD) δ: 7.95 (2H, d, J = 8.2 Hz), 7.44-7.30 (7H, m), 7.23 (2H, d, J = 8.2 Hz), 7.17 (2H, d, J = 8.2 Hz), 4.64 (1H, dd, J = 9.2, 3.7 Hz), 4.43 (1H, d, J = 11.3 Hz), 4.21 (1H, d, J = 11.3 Hz), 4.05 (1H, d, J = 14.6 Hz), 4.00 (1H, d, J = 14.6 Hz), 3.13 (1H, dd, J = 13.7, 9.2 Hz), 2.92 (1H, dd, J = 13.7, 3.7 Hz), 2.78 (2H, t, J = 7.3 Hz), 2.61 (2H, t, J = 7.9 Hz), 2.21 (2H, t, J = 7.0 Hz), 1.84-1.41 (13H, m), 1.22-1.02 (2H, m). | 558 | −44.0 (c = 0.23, MeOH) |

TABLE 49

| Example | Structural formula | $^1$H-NMR | ESI-MS (M + H)+ | Angle of rotation $[\alpha]_D$ |
|---|---|---|---|---|
| 40 | | (CD$_3$OD) δ: 7.95 (2H, d, J = 8.2 Hz), 7.45-7.29 (7H, m), 7.26-7.06 (8H, m), 4.62 (1H, dd, J = 8.8, 3.8 Hz), 4.42 (1H, d, J = 11.4 Hz), 4.22 (1H, d, J = 11.4 Hz), 4.04 (1H, d, J = 14.4 Hz), 3.99 (1H, d, J = 14.4 Hz), 3.11 (1H, dd, J = 13.9, 8.8 Hz), 2.90 (1H, dd, J = 13.9, 3.8 Hz), 2.89 (4H, s), 2.81-2.72 (2H, m), 2.21 (2H, t, J = 6.9 Hz), 1.71-1.41 (4H, m). | 600 | −40.3 (c = 0.25, MeOH) |
| 41 | | (CD$_3$OD) δ: 7.94 (2H, d, J = 8.4 Hz), 7.51 (2H, d, J = 7.9 Hz), 7.44-7.28 (9H, m), 7.22 (2H, d, J = 7.9 Hz), 7.17 (2H, d, J = 7.9 Hz), 4.61 (1H, dd, J = 8.6, 3.8 Hz), 4.42 (1H, d, J = 11.4 Hz), 4.22 (1H, d, J = 11.4 Hz), 4.03 (1H, d, J = 14.0 Hz), 3.98 (1H, d, J = 14.0 Hz), 3.16-2.85 (6H, m), 2.81-2.71 (2H, m), 2.21 (2H, t, J = 7.0 Hz), 1.69-1.42 (4H, m). | 634 | −30.9 (c = 0.27, MeOH) |

TABLE 49-continued

| Example | Structural formula | ¹H-NMR | ESI-MS (M + H)+ | Angle of rotation [α]$_D$ |
|---|---|---|---|---|
| 42 | (structure: 4-chlorophenyl-O-phenyl-CH₂-O-CH(Ph)-CH₂-N(CH₂-C₆H₄-COOH)(CH₂CH₂CH₂CH₂COOH)) | (CD₃OD) δ: 7.85 (2H, d, J = 8.1 Hz), 7.36-7.17 (11H, m), 6.92-6.79 (4H, m), 4.55 (1H, dd, J = 8.6, 3.8 Hz), 4.31 (1H, d, J = 11.5 Hz), 4.18 (1H, d, J = 11.5 Hz), 3.95 (1H, d, J = 13.7 Hz), 3.89 (1H, d, J = 13.7 Hz), 3.01 (1H, dd, J = 13.7, 8.6 Hz), 2.80 (1H, dd, J = 13.7, 3.8 Hz), 2.69 (2H, t, J = 7.1 Hz), 2.13 (2H, t, J = 6.9 Hz), 1.64-1.34 (4H, m). | 588 | −34.7 (c = 0.32, MeOH) |

TABLE 50

| Example | Structural formula | ¹H-NMR | ESI-MS (M + H)+ | Angle of rotation [α]$_D$ |
|---|---|---|---|---|
| 43 | (structure: phenethyl-thiophene-CH₂-O-CH(Ph)-CH₂-N(CH₂-C₆H₄-COOH)(CH₂CH₂CH₂CH₂COOH)) | (CD₃OD) δ: 8.03 (2H, d, J = 8.4 Hz), 7.49 (2H, d, J = 8.4 Hz), 7.45-7.33 (5H, m), 7.24-7.10 (5H, m), 6.76 (1H, d, J = 3.5 Hz), 6.65 (1H, d, J = 3.5 Hz), 4.76 (1H, dd, J = 9.8, 3.3 Hz), 4.57 (1H, d, J = 12.5 Hz), 4.36 (1H, d, J = 12.5 Hz), 4.20 (2H, s), 3.24 (1H, dd, J = 13.7, 9.8 Hz), 3.13-3.02 (3H, m), 2.99-2.83 (4H, m), 2.27 (2H, t, J = 7.1 Hz), 1.76-1.66 (2H, m), 1.58-1.48 (2H, m). | 572 | −57.9 (c = 0.33, MeOH) |
| 44 | (structure: 4-tert-butylphenyl-fluorophenyl-CH₂-O-CH(Ph)-CH₂-N(CH₂-C₆H₄-COOH)(CH₂CH₂CH₂CH₂COOH)) | (CD₃OD) δ: 7.94 (2H, d, J = 8.2 Hz), 7.55 (2H, d, J = 8.8 Hz), 7.47 (2H, d, J = 8.8 Hz), 7.45-7.28 (10H, m), 4.70 (1H, dd, J = 8.8, 3.8 Hz), 4.49 (1H, d, J = 11.9 Hz), 4.40 (1H, d, J = 11.9 Hz), 4.04 (1H, d, J = 13.7 Hz), 3.98 (1H, d, J = 13.7 Hz), 3.10 (1H, dd, J = 13.7, 8.8 Hz), 2.89 (1H, dd, J = 13.7, 3.8 Hz), 2.77 (2H, t, J = 7.1 Hz), 2.21 (2H, t, J = 6.9 Hz), 1.69-1.44 (4H, m), 1.34 (9H, s). | 612 | −32.8 (c = 0.29, MeOH) |

TABLE 51

| Example | Structural formula | ¹H-NMR | ESI-MS (M + H)+ | Angle of rotation [α]$_D$ |
|---|---|---|---|---|
| 45 | | (CD$_3$OD) δ: 7.94 (2H, d, J = 8.2 Hz), 7.45-7.07 (13H, m), 6.97 (1H, dd, J = 7.8, 1.5 Hz), 6.90 (1H, dd, J = 11.1, 1.5 Hz), 4.66 (1H, dd, J = 8.8, 3.8 Hz), 4.43 (1H, d, J = 11.6 Hz), 4.32 (1H, d, J = 11.6 Hz), 4.02 (1H, d, J = 14.0 Hz), 3.97 (1H, d, J = 14.0 Hz), 3.07 (1H, dd, J = 13.9, 8.8), 2.90 (4H, s), 2.88 (1H, dd, J = 13.9, 3.8 Hz), 2.75 (2H, t, J = 7.2 Hz), 2.20 (2H, t, J = 7.0 Hz), 1.69-1.42 (4H, m). | 584 | −33.5 (c = 0.33, MeOH) |
| 46 | | (CD$_3$OD) δ: 7.93 (2H, d, J = 8.4 Hz), 7.43-7.28 (8H, m), 7.14 (2H, d, J = 1.8 Hz), 4.64 (1H, dd, J = 8.8, 3.8 Hz), 4.46 (1H, d, J = 11.4 Hz), 4.28 (1H, d, J = 11.4 Hz), 4.04 (1H, d, J = 14.5 Hz), 3.99 (1H, d, J = 14.5 Hz), 3.09 (1H, dd, J = 13.8, 8.8 Hz), 2.89 (1H, dd, J = 13.8, 3.8 Hz), 2.76 (2H, t, J = 6.8 Hz), 2.19 (2H, t, J = 7.1 Hz), 1.67-1.43 (4H, m), 1.29 (18H, s). | 574 | −38.5 (c = 0.29, MeOH) |

TABLE 52

| Example | Structural formula | ¹H-NMR | ESI-MS (M + H)+ | Angle of rotation [α]$_D$ |
|---|---|---|---|---|
| 47 | | (CD$_3$OD) δ: 7.94 (2H, d, J = 8.2 Hz), 7.44-7.28 (7H, m), 7.22 (2H, d, J = 8.4 Hz), 7.16 (2H, d, J = 8.4 Hz), 4.62 (1H, dd, J = 9.0, 3.8 Hz), 4.42 (1H, d, J = 11.3 Hz), 4.21 (1H, d, J = 11.3 Hz), 4.03 (1H, d, J = 13.6 Hz), 3.97 (1H, d, J = 13.6 Hz), 3.10 (1H, dd, J = 13.6, 9.0 Hz), 2.89 (1H, dd, J = 13.6, 3.8 Hz), 2.75 (2H, t, J = 7.3 Hz), 2.63-2.51 (2H, m), 2.21 (2H, t, J = 7.0 Hz), 1.68-1.39 (6H, m), 0.96 (9H, s). | 546 | −45.2 (c = 0.38, MeOH) |

TABLE 52-continued

| Example | Structural formula | $^1$H-NMR | ESI-MS (M + H)+ | Angle of rotation $[\alpha]_D$ |
|---|---|---|---|---|
| 48 | | (CD$_3$OD) δ: 7.91 (2H, d, J = 8.2 Hz), 7.36-7.29 (9H, m), 7.22 (1H, dt, J = 6.7, 1.8 Hz), 6.98-6.91 (4H, m), 4.57 (1H, dd, J = 7.8, 4.8 Hz), 4.41 (1H, d, J = 11.5 Hz), 4.30 (1H, d, J = 11.5 Hz), 3.88 (1H, d, J = 13.8 Hz), 3.79 (1H, d, J = 13.8 Hz), 2.96 (1H, dd, J = 13.8, 7.8 Hz), 2.76 (1H, dd, J = 13.8, 4.8 Hz), 2.64 (2H, t, J = 6.8 Hz), 2.20 (2H, t, J = 6.8 Hz), 1.58-1.47 (4H, m). | 622 | −20.0 (c = 0.28, MeOH) |

TABLE 53

| Example | Structural formula | $^1$H-NMR | ESI-MS (M + H)+ | Angle of rotation $[\alpha]_D$ |
|---|---|---|---|---|
| 49 | | (CD$_3$OD) δ: 7.90 (2H, d, J = 8.2 Hz), 7.40-7.25 (6H, m), 7.20 (1H, dt, J = 6.5, 1.7 Hz), 7.12 (2H, d, J = 1.8 Hz), 4.56 (1H, dd, J = 7.7, 4.6 Hz), 4.45 (1H, d, J = 11.4 Hz), 4.31 (1H, d, J = 11.4 Hz), 3.90 (1H, d, J = 13.9 Hz), 3.81 (1H, d, J = 13.9 Hz), 2.95 (1H, dd, J = 13.6, 7.7 Hz), 2.78 (1H, dd, J = 13.6, 4.6 Hz), 2.62 (2H, t, J = 6.6 Hz), 1.55-1.44 (4H, m), 1.29 (18H, s). | 608 | −30.3 (c = 0.27, MeOH) |
| 50 | | (CD$_3$OD) δ: 7.93 (2H, d, J = 8.2 Hz), 7.68 (2H, d, J = 8.8 Hz), 7.45-7.26 (9H, m), 7.10-6.99 (4H, m), 4.62 (1H, dd, J = 8.4, 3.8 Hz), 4.42 (1H, d, J = 11.5 Hz), 4.32 (1H, d, J = 11.5 Hz), 3.99 (1H, d, J = 14.1 Hz), 3.92 (1H, d, J = 14.1 Hz), 3.07 (1H, dd, J = 13.7, 8.4 Hz), 2.84 (1H, dd, J = 13.7, 3.8 Hz), 2.74 (2H, t, J = 6.4 Hz), 2.21 (2H, t, J = 6.8 Hz), 1.68-1.46 (4H, m). | 579 | −22.6 (c = 0.36, MeOH) |

TABLE 53-continued

| Example | Structural formula | ¹H-NMR | ESI-MS (M + H)+ | Angle of rotation [α]$_D$ |
|---|---|---|---|---|
| 51 | | (CD$_3$OD) δ: 7.93 (2H, d, J = 8.2 Hz), 7.47-7.25 (8H, m), 4.64 (1H, dd, J = 8.3, 3.8 Hz), 4.57 (1H, d, J = 12.5 Hz), 4.50 (1H, d, J = 12.5 Hz), 3.95 (1H, d, J = 14.0 Hz), 3.87 (1H, d, J = 14.0 Hz), 3.00 (1H, dd, J = 13.9, 8.3 Hz), 2.79 (1H, dd, J = 13.9, 3.8 Hz), 2.69 (2H, t, J = 6.0 Hz), 2.22 (2H, t, J = 6.3 Hz), 1.61-1.49 (4H, m), 1.40 (9H, s). | 525 | −41.2 (c = 0.36, MeOH) |

TABLE 54

| Example | Structural formula | ¹H-NMR | ESI-MS (M + H)+ | Angle of rotation [α]$_D$ |
|---|---|---|---|---|
| 52 | | (CD$_3$OD) δ: 7.93 (2H, d, J = 8.2 Hz), 7.43-7.27 (10H, m), 6.99 (2H, d, J = 9.0 Hz), 6.77 (1H, dd, J = 8.2, 2.5 Hz), 6.71 (1H, dd, J = 11.0, 2.5 Hz), 4.65 (1H, dd, J = 8.7, 3.9 Hz), 4.42 (1H, d, J = 11.7 Hz), 4.35 (1H, d, J = 11.7 Hz), 4.00 (1H, d, J = 13.9 Hz), 3.93 (1H, d, J = 13.9 Hz), 3.05 (1H, dd, J = 13.8, 8.7 Hz), 2.84 (1H, dd, J = 13.8, 3.9 Hz), 2.74 (2H, t, J = 6.9 Hz), 2.21 (2H, t, J = 6.8 Hz), 1.67-1.44 (4H, m). | 606 | −26.4 (c = 0.31, MeOH) |
| 53 | | (CD$_3$OD) δ: 7.92 (2H, d, J = 8.4 Hz), 7.38-7.28 (5H, m), 7.21 (1H, dt, J = 6.7, 1.7 Hz), 6.73 (1H, d, J = 3.5 Hz), 6.69 (1H, d, J = 3.5 Hz), 4.64 (1H, dd, J = 8.1, 4.6 Hz), 4.54 (1H, d, J = 12.3 Hz), 4.39 (1H, d, J = 12.3 Hz), 3.92 (1H, d, J = 13.7 Hz), 3.83 (1H, d, J = 13.7 Hz), 2.96 (1H, dd, J = 13.8, 8.1 Hz), 2.78 (1H, dd, J = 13.8, 4.6 Hz), 2.65 (2H, t, J = 6.4 Hz), 2.20 (2H, t, J = 6.6 Hz), 1.55-1.50 (4H, m), 1.34 (9H, s). | 559 | −49.1 (c = 0.10, MeOH) |

TABLE 55

| Example | Structural formula | ¹H-NMR | ESI-MS (M + H)+ | Angle of rotation $[\alpha]_D$ |
|---|---|---|---|---|
| 54 | (structure) | (CD$_3$OD) δ: 7.86 (2H, d, J = 8.1 Hz), 7.60 (1H, d, J = 8.3 Hz), 7.54 (1H, s), 7.37-7.18 (6H, m), 7.11 (1H, s), 7.06 (1H, dd, J = 8.2, 1.3 Hz), 4.67 (1H, d, J = 12.6 Hz), 4.65 (1H, dd, J = 7.6, 4.9 Hz), 4.52 (1H, d, J = 12.6 Hz), 3.86 (1H, d, J = 13.9 Hz), 3.77 (1H, d, J = 13.9 Hz), 2.96 (1H, dd, J = 13.7, 7.6 Hz), 2.76 (1H, dd, J = 13.7, 4.9 Hz), 2.61 (2H, t, J = 6.7 Hz), 2.15 (2H, t, J = 6.7 Hz), 2.05-1.96 (1H, m), 1.52-1.45 (4H, m), 1.01-0.95 (2H, m), 0.77-0.70 (2H, m). | 593 | −62.6 (c = 0.51, MeOH) |
| 55 | (structure) | (CD$_3$OD) δ: 7.89-7.84 (3H, m), 7.69 (1H, d, J = 8.6 Hz), 7.34-7.28 (6H, m), 7.25-7.20 (1H, m), 7.18 (1H, s), 4.66 (1H, d, J = 12.8 Hz), 4.62 (1H, dd, J = 7.5, 5.0 Hz), 4.57 (1H, d, J = 12.8 Hz), 3.85 (1H, d, J = 13.9 Hz), 3.76 (1H, d, J = 13.9 Hz), 2.94 (1H, dd, J = 13.8, 7.5 Hz), 2.75 (1H, dd, J = 13.8, 5.0 Hz), 2.61 (2H, t, J = 6.7 Hz), 2.17 (2H, t, J = 6.8 Hz), 1.53-1.46 (4H, m). | 587 | −49.0 (c = 0.51, MeOH) |

TABLE 56

| Example | Structural formula | ¹H-NMR | ESI-MS (M + H)+ | Angle of rotation $[\alpha]_D$ |
|---|---|---|---|---|
| 56 | (structure) | (CD$_3$OD) δ: 7.91 (2H, d, J = 8.2 Hz), 7.36-7.27 (5H, m), 7.21 (1H, dt, J = 6.5, 1.8 Hz), 7.12 (2H, d, J = 8.2 Hz), 6.94 (2H, d, J = 8.8 Hz), 6.66 (1H, d, J = 3.8 Hz), 6.34 (1H, d, J = 3.8 Hz), 4.63 (1H, dd, J = 7.7, 4.8 Hz), 4.50 (1H, d, J = 12.5 Hz), 4.35 (1H, d, J = 12.5 Hz), 3.89 (1H, d, J = 14.1 Hz), 3.79 (1H, d, J = 14.1 Hz), 2.93 (1H, dd, J = 13.8, 4.8 Hz), 2.62 (2H, t, J = 6.7 Hz), 2.29 (3H, s), 2.19 (2H, t, J = 6.3 Hz), 1.55-1.47 (4H, m). | 609 | −41.0 (c = 0.96, MeOH) |

Example 57

4-{[N-(4-Carboxy-3,3-dimethylbutyl)-N-[2-(3-chlorophenyl)-2-[4-(2-phenylethyl)benzyloxy]ethyl]amino]methyl}benzoic acid Reference Example 115 (206 mg) was dissolved in THF (2.0 mL), acetic acid (57 μL) was added, and the reaction solution was stirred at room temperature for 10 minutes. Then, sodium triacetoxyborohydride (254 mg) was added, and then the reaction solution was stirred at the same temperature for 19 hours. A saturated aqueous solution of sodium hydrogen carbonate was added and the reaction solution was stirred, and then extracted with ethyl acetate. The solvent was evaporated under reduced pressure, and the residue was purified by silica gel column chromatography (10 to 40% ethyl acetate/hexane) to yield the product (292 mg) as a colorless oil. The product (285 mg) was dissolved in a mixed solution of methanol and THF (3:1, 4.0 mL), a 2.5 mol/L aqueous solution of sodium hydroxide (0.9 mL) was added, and the reaction solution was stirred at 60° C. for 3 hours. The reaction solution was cooled to room temperature, adjusted to pH 4 with 1 mol/L hydrochloric acid, and then extracted with chloroform. The solvent was evaporated under reduced pressure, and the residue was purified by silica gel column chromatography (5% to 15% methanol/chloroform) to yield the title compound (199 mg) as a white amorphous.

$^1$H-NMR (DMSO-D$_6$) δ: 7.80 (2H, d, J=8.1 Hz), 7.41-7.14 (15H, m), 4.55 (1H, dd, J=6.5, 5.3 Hz), 4.34 (1H, d, J=11.7 Hz), 4.27 (1H, d, J=11.7 Hz), 3.70 (1H, d, J=14.5 Hz), 3.63 (1H, d, J=14.5 Hz), 2.85 (4H, s), 2.78 (1H, dd, J=13.3, 6.5 Hz), 2.56 (1H, dd, J=13.3, 5.3 Hz), 2.48-2.42 (2H, m), 2.01 (2H, s), 1.45-1.38 (2H, m), 0.85 (6H, s).
ESI-MS Found: m/z 629 (M+H)$^+$ The compounds of Examples 58 and 59 manufactured with a similar method to that of Example 57 using the compounds of corresponding Reference Examples are shown in Table 57.

TABLE 57

| Example | Structural formula | $^1$H-NMR | ESI-MS (M + H)+ |
|---|---|---|---|
| 58 | 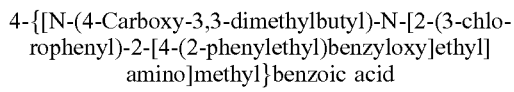 | (DMSO-D$_6$) δ: 7.81 (2H, d, J = 8.2 Hz), 7.41-7.15 (11H, m), 6.76 (1H, d, J = 3.5 Hz), 6.67 (1H, d, J = 3.5 Hz), 4.58 (1H, dd, J = 6.9, 5.5 Hz), 4.45 (1H, d, J = 12.3 Hz), 4.38 (1H, d, J = 12.3 Hz), 3.70 (1H, d, J = 12.3 Hz), 3.70 (1H, d, J = 14.8 Hz), 3.62 (1H, d, J = 14.8 Hz), 3.09-3.01 (2H, m), 2.93-2.85 (2H, m), 2.75 (1H, dd, J = 13.7, 5.5 Hz), 2.48-2.43 (2H, m), 2.02 (2H, s), 1.45-1.36 (2H, m), 0.86 (6H, s). | 635 |
| 59 | 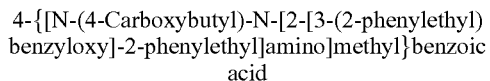 | (DMSO-D$_6$) δ: 7.82 (2H, d, J = 7.7 Hz), 7.36-7.15 (12H, m), 6.74 (1H, d, J = 3.2 Hz), 6.68 (1H, d, J = 3.2 Hz), 4.58 (1H, dd, J = 6.8, 5.3 Hz), 4.43 (1H, d, J = 12.3 Hz), 4.35 (1H, d, J = 12.3 Hz), 3.72 (1H, d, J = 14.8 Hz), 3.65 (1H, d, J = 14.8 Hz), 3.09-3.02 (2H, m), 2.92-2.85 (2H, m), 2.76 (1H, dd, J = 13.7, 6.8 Hz), 2.55 (1H, dd, J = 13.7, 5.3 Hz), 2.02 (2H, s), 1.47-1.40 (2H, m), 0.90-0.83 (8H, m). | 600 |

Example 60

4-{[N-(4-Carboxybutyl)-N-[2-[3-(2-phenylethyl)benzyloxy]-2-phenylethyl]amino]methyl}benzoic acid Reference Example 105 (230 mg) was dissolved in acetonitrile (6.0 mL), and potassium carbonate (199 mg), methyl 5-bromovalerate (167 μL) and sodium iodide (22 mg) were added, and the reaction solution was stirred and heated under reflux for 23 hours. The reaction solution was cooled to room temperature, and the solvent was evaporated under reduced pressure. Then, the residue was suspended in water, and the suspension was extracted with ethyl acetate. The combined organic layer was dried over anhydrous sodium sulfate, and then the solvent was evaporated under reduced pressure. The residue was purified by silica gel column chromatography (10 to 50% ethyl acetate/hexane) to yield the product (258 mg) as a colorless oil. The product (250 mg) was dissolved in a mixed solution of methanol and THF (3:1, 5.0 mL), a 1 mol/L aqueous solution of sodium hydroxide (2.5 mL) was added, and the reaction solution was stirred at room temperature for 18 hours. The solvent was evaporated under reduced pressure, and the residue was adjusted to pH 4 with 1 mol/L hydrochloric acid, and then extracted with a mixed solution of methanol and chloroform (1:9). The combined organic layer was dried over anhydrous sodium sulfate, and then the solvent was evaporated under reduced pressure, and the residue was purified by silica gel column chromatography (5% to 15% methanol/chloroform) to yield the title compound (208 mg) as a white amorphous.

$^1$H-NMR (DMSO-D$_6$) δ: 7.80 (2H, d, J=8.1 Hz), 7.35-7.08 (16H, m), 4.55 (1H, dd, J=7.1, 5.5 Hz), 4.32 (1H, d, J=11.9 Hz), 4.26 (1H, d, J=11.9 Hz), 3.73 (1H, d, J=14.6 Hz), 3.65 (1H, d, J=14.6 Hz), 2.83 (4H, s), 2.80 (1H, dd, J=13.0, 7.1 Hz), 2.57 (1H, dd, J=13.0, 5.5 Hz), 2.46-2.40 (2H, m), 2.10-2.06 (2H, m), 1.40-1.34 (4H, m). ESI-MS Found: m/z 566 (M+H)$^+$ The compounds of Examples 61 and 62 manufactured with a similar method to that of Example 60 using the compounds of corresponding Reference Examples are shown in Tables 58 and 59.

TABLE 58

| Example | Structural formula | $^1$H-NMR | ESI-MS (M + H)+ |
|---|---|---|---|
| 61 | | (DMSO-D$_6$) δ: 7.80 (2H, d, J = 8.1 Hz), 7.33-7.12 (15H, m), 4.55 (1H, dd, J = 7.0, 5.8 Hz), 4.29 (1H, d, J = 11.7 Hz), 4.23 (1H, d, J = 11.7 Hz), 3.69 (1H, d, J = 14.6 Hz), 3.61 (1H, d, J = 14.6 Hz), 2.84 (4H, s ) 2.76 (1H, dd, J = 13.7, 7.0 Hz), 2.53 (1H dd, J = 13.7, 5.8 Hz), 2.44- 2.37 (2H, m), 2.11-2.04 (2H, m), 1.39-1.28 (4H, m). | 584 |

TABLE 59

| Example | Structural formula | $^1$H-NMR | ESI-MS (M + H)+ | Angle of rotation [α]$_D$ |
|---|---|---|---|---|
| 62 | | (CD$_3$OD) δ: 7.95 (2H, d, J = 8.2 Hz), 7.41-7.07 (16H, m), 4.62 (1H, dd, J = 8.9, 3.8 Hz), 4.40 (1H, d, J = 11.4 Hz), 4.22 (1H, d, J = 11.4 Hz), 4.06 (1H, d, J = 13.5 Hz), 4.03 (1H, d, J = 13.5 Hz), 3.11 (1H, dd, J = 13.8, 8.9 Hz), 2.90 (1H, dd, J = 13.8, 3.8 Hz), 2.87 (4H, s), 2.77 (2H, t, J = 7.4 Hz), 2.20 (2H, t, J = 6.9 Hz), 1.65-1.45 (4H, m). | 566 | +26.4 (c = 0.25, CHCl$_3$) |

The compound of the present invention was tested for the sGC activation effect in accordance with the Test Examples described below.

Test Example 1

Maximum Effect of sGC sGC Activation Effect

For the assay, chinese hamster ovary cells (CHO-K1 cells) stably expressing both α and β subunits of human sGC and mouse cyclic nucleotide-gated channel (CNGA2) were used.

The CHO-K1 cells stably expressing human sGC and mouse CNGA2 was cultured at 37° C. on F-12 medium containing 10% (v/v) fetal bovine serum (FBS), penicillin (100 U/mL), streptomycin (100 μg/mL), G418 (250 μg/mL) and Zeocin (250 μg/mL). The cells were suspended in a culture medium, seeded on a 96 well plate, and then cultured at 37° C. for 24 hours. The cells were washed with Assay buffer 1 (140 mmol/L sodium chloride, 5 mmol/L potassium chloride, 0.5 mmol/L magnesium chloride, 0.01 mmol/L calcium chloride, 10 mmol/L glucose, 0.4 mmol/L magnesium sulfate, 10 mmol/L 4-(2-hydroxyethyl)piperazin-1-ylethanesulfonic acid and 125 μmol/L sulfinpyrazone, pH 7.4), and then added a solution containing Fura2-AM, a fluorescent $Ca^{2+}$ indicator, in Assay buffer 1 at 5 mol/L concentration thereto as an indicator solution, and cultured at 37° C. for 60 minutes. The culture medium was removed, and the cells were washed with Assay buffer 1, and then added a solution containing the test compound thereto, and cultured at room temperature for 10 minutes. A plate was placed onto a fluorometer (FlexStation II, Molecular Devices), and the intracellular calcium concentration was determined as the ratio of fluorescent intensity, obtained from measurement using 340 nm and 380 nm as excitation wavelength and 510 nm as detection wavelength.

The solution of the test compound was prepared by dissolving each test compound in DMSO at 10 mmol/L, and then diluting the solution for the test concentration at 10 μmol/L with Assay buffer (140 mmol/L sodium chloride, 5 mmol/L potassium chloride, 0.5 mmol/L magnesium chloride, 1 mmol/L calcium chloride, 10 mmol/L glucose, 0.4 mmol/L magnesium sulfate, 10 mmol/L 4-(2-hydroxyethyl)piperazin-1-ylethanesulfonic acid, 125 mol/L sulfinpyrazone, 100 μmol/L isobutyl methyl xanthine, and 10 μmol/L 1H-[1,2,4]-oxadiazol[4,3-a]quinoxaline-1-one (hereinafter, ODQ), pH 7.4). The evaluation in the absence of ODQ was performed similarly, except that ODQ was not added to Assay buffer 2. As a control solution, a DMSO solution was used instead of the test compound solution.

The activity of the test compound defined as the increase rate of the sGC activity (%) at the time of adding the solution of the test compound with respect to the sGC activity at the time of adding the control solution, was calculated by dividing the fluorescent intensity ratio at the time of adding the test compound by the fluorescent intensity ratio of the control solution, and subtracting the sGC activity at the time of adding the control solution (100%).

The assay results are shown in Table 60.

TABLE 60

| Test compound (Example No.) | Emax (%) ODQ− (Heme-dependent) | Emax (%) ODQ+ (Heme-independent) |
|---|---|---|
| 2 | 130.0 | 102.0 |
| 10 | 102.6 | 141.0 |
| 15 | 89.1 | 87.7 |

TABLE 60-continued

| Test compound (Example No.) | Emax (%) ODQ− (Heme-dependent) | Emax (%) ODQ+ (Heme-independent) |
|---|---|---|
| 16 | 92.4 | 132.0 |
| 18 | 96.2 | 129.0 |
| 19 | 114.3 | 122.0 |
| 22 | 105.5 | 115.0 |
| 23 | 131.6 | 113.0 |
| 24 | 150.4 | 132.0 |
| 25 | 129.7 | 114.0 |
| 26 | 92.6 | 110.0 |
| 27 | 186.8 | 118.0 |
| 28 | 98.0 | 114.0 |
| 29 | 98.2 | 110.0 |
| 30 | 83.4 | 129.0 |
| 32 | 127.5 | 87.7 |
| 34 | 82.3 | 125.0 |
| 39 | 148.4 | 142.0 |
| 40 | 127.4 | 120.0 |
| 42 | 142.6 | 127.0 |
| 43 | 108.3 | 124.0 |
| 45 | 109.1 | 123.0 |
| 46 | 160.6 | 108.0 |
| 60 | 110.1 | 88.9 |
| Cinaciguat | 53.0 | 86.0 |

If sGC is activated in this assay, intracellular cGMP concentration increases and accordingly intracellular $Ca^{2+}$ concentration is increased by opening of CNGA2. Accordingly, sGC activation can be measured as the change of $Ca^{2+}$ concentration in the cell. ODQ is a specific oxidant for a heme-binding iron atom, and the iron atom of heme is oxidated in the presence of ODQ, and thus heme-dependent sGC activation does not occur. Accordingly, it is possible to evaluate maximum sGC activation effect including heme-dependent activation in the absence of ODQ, and also possible to evaluate heme independent sGC activation effect in the presence of ODQ. Meanwhile, in any case using any test compound (including using Cinaciguat as Comparative Example), the sGC activity showed the constant maximum value at 10 μmol/L or higher concentration in the presence and absence of ODQ. According to this result, the activity value at 10 μmol/L was defined as the ability for maximizing sGC activity (Emax) of each test compound.

As shown in Table 60, it was revealed that any compound of the present invention remarkably increases the sGC activity in the presence of ODQ, and is a heme-independent, direct sGC activator. In addition, it was revealed that the compound of the present invention shows higher Emax in comparison to Cinaciguat in either presence or absence of ODQ, and shows more excellent sGC activation effect in comparison to Cinaciguat.

Test Example 2

Evaluation for Blood Vessel Relaxation Activity

A representative compound of the present invention was assayed for blood vessel relaxation activity according to the Test Example described below. In the assay, a rat (male, SD) was phlebotomized from the upper part of the heart under pentobarbital (30 mg/kg) anesthesia, and the ventral aorta was extracted. The connective tissue adhering around the blood vessel in the ventral aorta was removed in an ice-cooled Krebs-Henseleit solution (KH solution) (118 mmol/L sodium chloride, 4.7 mmol/L potassium chloride, 1.2 mmol/L magnesium sulfate, 1.2 mmol/L potassium dihydrogenphosphate, 25 mmol/L sodium hydrogen carbonate, 2.5 mmol/L calcium chloride and 10 mmol/L glucose, pH 7.4). Then, a ring specimen of 2 mm length was prepared, and fixed in 5 mL organ bath filled with the KH solution. The KH solution was maintained at 37° C., and a mixed gas of 95% $O_2$ and 5% $CO_2$ was ventilated. The specimen was stabilized with 1 g of the resting tension for 1 hour. In the meantime, the KH solution was exchanged twice. The tension of the specimen was recorded with a multichannel recorder through a pickup and an amplifier. After stabilization of the specimen, contraction was induced with 1 μmol/L phenylephrine (Phe), and cumulative administration of each compound (0.001, 0.01, 0.03, 0.1, 0.3, 1, 3, 10, 30, 100, 1000, 10000 nmol/L) was carried out. In the case of evaluation at the time of containing ODQ, 10 μmol/L ODQ was added 10 minutes before administration of Phe, and similar evaluation was performed.

$EC_{50}$ value was calculated by Four-parameter Logistic Model with Assay Explorer (Accelrys, Inc.). Meanwhile, the solution of the test compound was prepared by dissolving the compound in DMSO to prepare solutions having the concentration of each test compound 1000 times higher than the final concentration.

The assay results are shown in Table 61.

TABLE 61

| Test compound (Example No.) | $EC_{50}$ Ratio (ODQ−/ODQ+) |
|---|---|
| 2 | 3.26 |
| 16 | 8.31 |
| 19 | 6.20 |
| 23 | 6.88 |
| 25 | 2.61 |
| 26 | 7.72 |
| 27 | 2.66 |
| 28 | 2.99 |
| 29 | 9.66 |
| 32 | 7.31 |
| 42 | 8.40 |
| 45 | 4.26 |
| Cinaciguat | 12.4 |

As shown in Table 61, it was revealed that any compound of the present invention shows lower $EC_{50}$ ratio than Cinaciguat, and is heme-independent in comparison to Cinaciguat.

INDUSTRIAL APPLICABILITY

A 4-aminomethylbenzoic acid derivative, a pharmaceutically acceptable salt thereof or a solvate thereof of the present invention has heme-independent excellent sGC activation effect, and thus is useful as an agent for treating or preventing various diseases involving soluble guanylate cyclase such as, for example, heart failure, hypertension, pulmonary hypertension or an ischemic heart disease.

The invention claimed is:
1. A compound represented by formula (1):

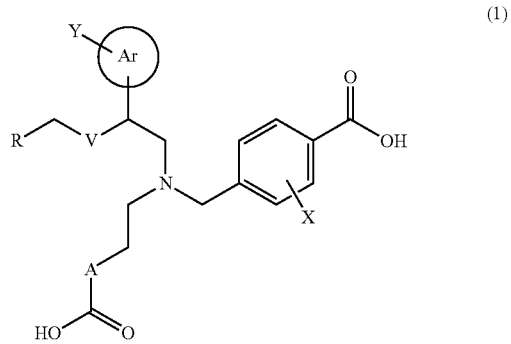

a pharmaceutically acceptable salt thereof or a solvate thereof,
wherein Ar represents an aryl group, or a 5- or 6-membered heteroaryl group containing a nitrogen atom, an oxygen atom or a sulfur atom;
Y represents a hydrogen atom, a $C_1$-$C_6$ alkyl group, a halo $C_1$-$C_4$ alkyl group, a cyano group, or a halogen atom;
A represents a $C_1$-$C_3$ alkylene chain which may be substituted with two $C_1$-$C_2$ alkyl groups, wherein the two $C_1$-$C_2$ alkyl groups may be substituted on the same carbon atom of the $C_1$-$C_3$ alkylene chain, and further the two $C_1$-$C_2$ alkyl groups may together form a $C_3$-$C_5$ saturated hydrocarbon ring containing one carbon atom of the $C_1$-$C_3$ alkylene chain;
X represents a hydrogen atom or a halogen atom;
V represents an oxygen atom or a methylene chain;
R represents a group selected from the formulae below

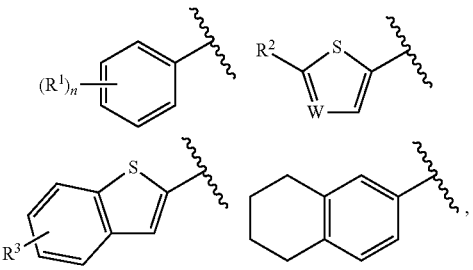

wherein $R^2$ and $R^3$ each independently represent a hydrogen atom, a halogen atom, a $C_1$-$C_6$ alkyl group which may have a substituent group, a $C_1$-$C_6$ alkoxy group, a $C_3$-$C_6$ cycloalkyl group, a $C_3$-$C_6$ cycloalkoxy group, a halo $C_1$-$C_4$ alkyl group, an aryl group which may have a substituent group on the aromatic ring, an aryloxy group which may have a substituent group on the aromatic ring, a benzyl group which may have a substituent group on the benzene ring, a phenethyl group which may have a substituent group on the benzene ring, or a benzyloxy group which may have a substituent group on the benzene ring,
W represents =CH— or a nitrogen atom,
n represents an integer of 1 to 3, and when n is 2 or more, the n instances of $R^1$ may be different from each other.

2. The compound, pharmaceutically acceptable salt, or solvate according to claim 1, wherein Ar is a $C_{6-10}$ monocyclic or polycyclic aromatic hydrocarbon group, or a 5 to 6-membered heteroaryl group containing a nitrogen atom, an oxygen atom or a sulfur atom;

the group that may be substituted on the alkyl group, the aryl group, the aryloxy group, the benzyl group, the phenethyl group or the benzyloxy group represented by $R^1$, $R^2$ and $R^3$ is a group selected from a halogen atom, a $C_1$-$C_6$ alkyl group, a $C_1$-$C_6$ alkoxy group, a $C_3$-$C_6$ cycloalkyl group, a $C_3$-$C_6$ cycloalkoxy group, a $C_6$-$C_{10}$ aryl group, a $C_6$-$C_{10}$ aryloxy group, a benzyl group, a phenethyl group and a benzyloxy group.

3. The compound, pharmaceutically acceptable salt, or solvate according to claim 1, wherein Ar is a $C_{6-10}$ monocyclic or polycyclic aromatic hydrocarbon group, or a 5 to 6-membered heteroaryl group containing a nitrogen atom, an oxygen atom or a sulfur atom;

$R^1$, $R^2$ and $R^3$ are each independently a hydrogen atom; a halogen atom; a $C_{1-6}$ alkyl group which may be substituted with a $C_1$-$C_6$ alkoxy group, a $C_3$-$C_6$ cycloalkyl group or a $C_3$-$C_6$ cycloalkoxy group; a $C_1$-$C_6$ alkoxy group; a $C_3$-$C_6$ cycloalkyl group; a $C_3$-$C_6$ cycloalkoxy group; a halo $C_1$-$C_4$ alkyl group; a $C_6$-$C_{10}$ aryl group which may be substituted with a halogen atom, a $C_1$-$C_6$ alkyl group or a cyano group in the aromatic ring; a $C_6$-$C_{10}$ aryloxy group which may be substituted with a halogen atom, a $C_1$-$C_6$ alkyl group or a cyano group in the aromatic ring; a benzyl group which may be substituted with a halogen atom or a halo $C_1$-$C_4$ alkyl group in the benzene ring; a phenethyl group which may be substituted with a halogen atom or halo $C_1$-$C_4$ alkyl group in the benzene ring; or a benzyloxy group which may be substituted with a halogen atom or a halo $C_1$-$C_4$ alkyl group in the benzene ring.

4. The compound, pharmaceutically acceptable salt, or solvate according to claim 1, wherein A is —$CH_2$—, —$(CH_2)_2$—, —$(CH_2)_3$— or a structure described below

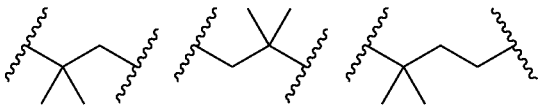

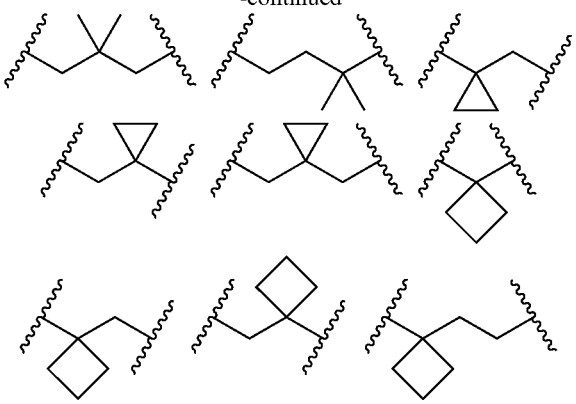

wherein the left end in each structure represents the binding site to the carboxyl group.

5. A pharmaceutical composition comprising the compound, pharmaceutically acceptable salt, or solvate according to claim 1, and a pharmaceutically acceptable carrier.

6. A method of treating heart failure or pulmonary hypertension, the method comprising administering an effective amount of the compound, pharmaceutically acceptable salt, or solvate according to claim 1 to a subject in need thereof.

7. The compound, pharmaceutically acceptable salt, or solvate according to claim 1, which is the compound.

8. The compound, pharmaceutically acceptable salt, or solvate according to claim 1, which is the pharmaceutically acceptable salt.

9. The compound, pharmaceutically acceptable salt, or solvate according to claim 1, which is the solvate.

* * * * *